US006951923B2

(12) United States Patent
Fisher et al.

(10) Patent No.: US 6,951,923 B2
(45) Date of Patent: Oct. 4, 2005

(54) GENES DISPLAYING ENHANCED EXPRESSION DURING CELLULAR SENESCENCE AND TERMINAL CELL DIFFERENTIATION AND USES THEREOF

(75) Inventors: Paul B. Fisher, Scarsdale, NY (US); Leszczyniecka Magdalena, Clifton, NJ (US)

(73) Assignee: Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/907,907

(22) Filed: Jul. 16, 2001

(65) Prior Publication Data

US 2003/0099660 A1 May 29, 2003

Related U.S. Application Data

(63) Continuation of application No. PCT/US00/02920, filed on Feb. 2, 2000, which is a continuation-in-part of application No. 09/243,277, filed on Feb. 2, 1999, now abandoned.

(51) Int. Cl.[7] ....................... C07K 16/00; A61K 39/395
(52) U.S. Cl. ............................ 530/387.9; 530/387.1; 530/388.1; 530/388.26; 424/139.1; 424/141.1; 424/146.1
(58) Field of Search ..................... 530/387.1, 387.9, 530/388.1, 388.26, 388.8; 424/130.1, 141.1, 146.1; 435/7.1

(56) References Cited

U.S. PATENT DOCUMENTS

| | | | |
|---|---|---|---|
| 5,194,596 A | * | 3/1993 | Tischer et al. |
| 5,200,313 A | | 4/1993 | Carrico |
| 5,350,836 A | * | 9/1994 | Kopchick et al. |
| 5,710,137 A | | 1/1998 | Fisher |
| 6,020,172 A | * | 2/2000 | Both |

FOREIGN PATENT DOCUMENTS

| | | |
|---|---|---|
| WO | WO 99/25878 | 5/1999 |
| WO | PCT/US00/02920 | 2/2000 |

OTHER PUBLICATIONS

Benjamin L. E. et al. 1998, Development 125:1591–1598.*
Vukicevic S. et al. 1996, PNAS USA 93:9021–9026.*
Massague J. 1987, Cell 49:437–438.*
Pilbeam C. C. et al. 1993, Bone 14:717–720.*
Skolnick J. et al. 2000, Trends in Biotech. 18:34–39.*
Smith et al. 1997, Nature Biotechnology 15:1222–1223.*
Brenner. 1999, Trends in Genetics 15:132–133.*
Fu et al. EMBO Journal, 1996, vol. 15, pp. 4392–4401.*
Powell et al. Pharmacogenetics, 1998, vol. 8, pp. 411–421.*
Vallejo et al. Biochimie, 2000, vol. 82, pp. 1129–1133.*
Jang et al. Clinical and Experimental Metastasis, 1997, vol. 15, pp. 469–483.*

Yehudai–resheff et al. 2001, Mol. Cell. Biol. 21(6):5408–5416.*
Accorsi A. et al. 1991, Biochem. Int. 24(1):23–31.*
Lewin B. Genes VI, 1997, CH. 29, pp. 847–848.*
Leszczyniecka M, Su Z, Kang D, Sarkar D, Fisher PB (2003). Expression regulation and genomic organization of human polynucleotide phosphorylase, hPNPase(old–35), a Type I interferon inducible early response gene. *Gene* 316:143–156.
Sarkar D, Leszczyniecka M, Kang DC, Lebedeva IV, Valerie K, Dhar S, Pandita TK, Fisher PB (2003). Down–regulation of Myc as a potential target for growth arrest induced by human polynucleotide phosphorylase (hPNPaseold–35) in human melanoma cells. *J Biol Chem.* 278(27):24542–24551.
Strausberg R (2003). Homo sapiens polyribonucleotide nucleotidyltransferase 1, mRNA (cDNA clone MGC:61565 Image:6062060), complete cds. GenBank Acc. No. BC053660.
Takahashi H, Furukawa T, Yano T (2003). Homo sapiens PNPase mRNA, partial cds. GenBank Acc. No. AY290863.
Leszczyniecka M, Kang DC, Sarkar D, Su ZZ, Holmes M, Valerie K, Fisher PB (2002). Identification and cloning of human polynucleotide phosphorylase, hPNPase old–35, in the context of terminal differentiation and cellular senescence. *Proc Natl Acad Sci USA* 99(26):16636–16641.
Leszczyniecka et al.(2002), GenBank Acc. No. AY027528.
Raijmakers R (2002). Homo sapiens mRNA for polynucleotide phosphorylase–like protein (PNPase gene). GenBank Acc. No. AJ458465.
(Oct. 16, 2001), GenBank Acc. No. P50849.
Madireddi MT, Dent P, Fisher PB (2000. Regulation of mda–7 gene expression during human melanoma differentiation. *Oncogene* Mar. 2, 2000;19(10):1362–1368.
Rosenberg LE, Schechter AN (2000). Gene therapist, heal thyself. *Science* 287:1751.
Strausberg R (2000). Homo sapiens polyribonucleotide nucleotidyltransferase 1 mRNA. GenBank Acc. No. BC000862.
Antic D, Lu N, Keene JD (1999). ELAV tumor antigen, Hel–N1, increases translation of neurofilament M mRNA and induces formation of neurties in human teratocarcinoma cells. *Genes Dev* 13:449–461.

(Continued)

*Primary Examiner*—Larry R. Helms
*Assistant Examiner*—David J. Blanchard
(74) *Attorney, Agent, or Firm*—Baker Botts LLP

(57) ABSTRACT

This invention provides for antibodies directed to OLD-35 protein, the product of the OLD-35 gene, which displays enhanced expression during cellular senescence and terminal cell differentiation.

2 Claims, 19 Drawing Sheets

OTHER PUBLICATIONS

Huang F, Adelman J, Jiang H, Goldstein NI, Fisher PB (1999). Identification and temporal expression pattern of genes modulated during irreversible growth arrest and terminal differentiation in human melanoma cells. *Oncogene* 18(23):3546–3552.

Leszczyniecka M. (Feb. 2, 1999), Keystone Symposium "Aging and Environmental Influences on Life Span," Feb. 2–7, 1999 (submitted abstract).

Roberts PJ, Mollapour E, Watts MJ, Linch DC (1999). Primitive myeloid cells express high levels of phospholipase A2 activity in the absence of leukotriene release:selective regulation by stem cell factor involving the MAP kinase pathway. *Blood* 94:1261–1272.

Wynford–Thomas (Jan. 1999). Cellular sensescence and cancer. *J. Pathol.* 187():100–111.

Branch A (1998). A good antisense is hard to find. *TIBS* 23:45–50.

Der SD, Zhou A, Williams BR, Silverman RH (1998). Identification of genes differentially regulated by interferon alpha, beta, or gamma using oligonucleotide arrays. *Proc Natl Acad Sci USA* 95:15623–15628.

Gire V, Wynford–Thomas D (1998). Reinitiation of DNA synthesis and cell division in senescent human fibroblasts by microinjection of anti–p53 antibodies. *Mol Cell Biol* 18(3):1611–1621.

Gonos et al. (Apr. 1998). Cloning and identification of genes that associate with mammalian replicative senescence. *Exp. Cell Res.* 240(1):66–74.

Lin JJ, Jiang H, Fisher PB (1998). Melanoma differentiation associated gene–9, mda–9, is a human gamma interferon responsive gene. *Gene* 207(2):105–110.

Niculescu AB 3rd, Chen X, Smetts M, Hengst L, Prives C, Reed SI (1998). Effects of p21 (Cip1/Waf1) at both the G1/S and the G2/M cell cycle transitions: pRb is a critical determinant in blocking DNA replication and in preventing endoreduplication. *Mol Cell Biol* 18(1):629–643.

Spicher A, Guicherit OM, Duret L, Aslanian A, Sanjines EM, Denko NC, Giaccia AJ, Blau HM (1998). Highly conserved RNA sequences that are sensors of environmental stress. *Mol Cell Biol* 18:7371–7382.

Stark GR, Kerr IM, Williams BR, Silverman RH, Schreiber RD (1998). How cells respond to interferons. *Ann Rev. Biochem* 67:227–264.

Zhang P, Vigne JL, Mellon SH (1998). Polyribonucleotide phosphorylase is a double–stranded DNA–binding protein. *DNA Cell Biol* 17(2):169–175.

Antic D, Keene JD (1997). Embryonic lethal abnormal visual RNA–binding proteins involved in growth, differentiation, and posttranscriptional gene expression. Am J Hum Genet. 61:273–278.

Blum, E, Py B, Carpousis AJ, Higgins CF (1997). Polyphosphate kinase is a component of the *Escherichia coli* RNA degradosome. *Mol Microbiol* 26(2):387–398.

Gura T (1997). Systems for identifying drugs are often faulty. *Science* 278(5340):1041–1042.

Stark GR, Kerr IM, Williams BR, Silverman RH, Schreiber RD (1998). How cells respond to interferons. *Ann Rev. Biochem* 67:227–264.

Strausberg (Jun. 1998), EST ov80.eo5.sl, GenBank Acc. No. AI023627.

Zhang P, Vigne JL, Mellon SH (1998). Polyribonucleotide phosphorylase is a double–stranded DNA–binding protein. *DNA Cell Biol.* 17(2):169–175.

Myer VE, Fan XC, Steitz JA (1997). Identification of HuR as a protein implicated in AUUUA–mediated mRNA decay. *EMBO J* 16(8):2130–2139.

Strausberg R (1997). EST nf94c12.sl. GenBank Acc. No. AA535914.

Strausberg R (1997). EST zs13d08.rl. Gen Bank Acc. No. AA252572.

Wilson RK (1997). EST zq51b10.rl. Gen Bank Acc. No. AA206675.

Verman IM, Somia N (1997). Gene therapy—promises, problems and prospects. *Nature* 389(6648):239–242.

Agrawal S (1996). Antisense oligonucleotides:towards clinical trials. *TIBTECH* 14:376–387.

Campisi J (1996). Replicative senescence: an old lives' tale? *Cell* 84(4):497–500.

Hayes R, Kudla J. Schuster G, Gabay L, Maliga P, Gruissem W (1996). chloroplast mRNA 3'–end processing by a high molecular weight protein complex is regulated by nuclear encoded RNA binding proteins. *EMBO J* 15:1132–1141.

Holt SE, Wright WE, Shay JW (1996). Regulation of telomerase activity in immortal cell lines. *Mol Cell Biol* 16(6):2932–2939.

Hudson (Jun. 1996), human STS EST127457, GenBank Acc. No. G26100.

Hudson (Jun. 1996), human STS EST324915, GenBank Acc. No. G25452.

Lacombe L, Orlow I, Silver D, Gerald WL, Fair WR, Reuter VE, Cordon–Cardo C (1996). Analysis of p21 WAF1/CIP1 in primary bladder tumors. *Oncol Res* 8(10–11):409–414.

Ledley FD (1996). Pharmaceutical Approach to somatic gene therapy. *Pharmaceutical Research* 13:1595–1614.

Lin JJ, Jiang H, Fisher PB (1996). Characterization of a novel melanoma differentiation associated gene, mda–9, that is down–regulated during terminal cell differentiation. *Mol Cell Different* 4(4):317–333.

Linke SP, Clarkin KC, Di Leonardo A, Tsou A, Wahl GM (1996). A reversible, p53–dependent G0/G1 cell cycle arrest induced by ribonucleotide depletion in the absence of detectable DNA damage. *Genes Dev* 10(8):934–947.

Luttinger A, Hahn J, Dubnau D. Polynucleotide phosphorylase is necessary for competence development in *Bacillus subtilis*. *Mol Microbiol* 19(2):343–356.

Luttinger et al. (Feb. 1996), GenBank Acc. No. U29668.

Ma WJ, Cheng S, Campbell C. Wright A, Furneaux (1996). Cloning and characterization of HuR, a ubiquitously expressed Elav–like protein. *J Biol Chem* 271(14):8144–8151.

Seydoux G, Mello CC, Pettitt J, Wood WB, Priess JR, Fire A (1996). Repression of gene expression in the embryonic germ lineage of C. elegans. *Nature* 382:713–716.

Smith JR, Pereira–Smith OM (1996). Replicative senescence: implications for in vivo aging and tumor suppression. *Science* 273(5271):63–67.

Wilson RK (1996). EST zl75a08.sl. GenBank Acc. No. AA055633.

Wilson RK (1996). EST yz92g09.sl. GenBank Acc. No. N62372.

Chen CY, Shyu AB (1995). AU–rich elements: characterization and importanace in mRNA degradation. *Trends Biochem Sci* 20(11):465–470.

Dimri GP, Lee X, Basile G, Acosta M, Scott G, Roskelley C, Medrano EE, Linskens M, Rubelj I, Pereira–Smith O, et al. (1995). A biomarker that identifies senescent human cells in culture and in aging skin in vivo. *Proc Natl Acad Sci USA* 92(20):9363–9367.

Good PJ (1995). A conserved family of elav–like genes in vertebrates. *Proc Natl Acad Sci USA* 92:4557–4561.

Hillier (Jul. 1995), EST y114a01.rl, Gen Bank Acc. No. H26598.

Jiang H, Lin JJ, Su ZZ. Goldstein NI, Fisher PB (1995). Subtraction hybridization identifies a novel melanoma differentiation associated gene, mda–7, modulated during human melanoma differentiation, growth and progression. *Oncogene* 11(12:2477–2486.

Jiang H, Lin J, Su ZZ, Herlyn M, Kerbel RS, Weissman BE, Welch DR, Fisher PB (1995). The melanoma differentiation– associated gene mda–6, which encodes the cyclin–dependent kinase inhibitor p21, is differentially expressed during growth, differentiation and progresssion in human melanoma cells. *Oncogene* 10(9):1855–1864.

Darnell JE, Jr., Kerr IM, Stark GR (1994). Jak–STAT Pathways and transcriptional activation in response to IFNs and other extracellular signaling proteins. *Science* 264(5164):1415–1421.

Gutterman JU (1994). Cytokine therapeutics: lessons from interferon alpha. *Proc Natl Acad Sci USA* 91(4):1198–1205.

Jiang H, Lin J, Fisher PB (1994). A molecular definition of terminal cell differentiation in human melanoma cells. *Mol Cell Different* 2:221–239.

Jiang H, Lin J. Su ZZ, Collart FR, Huberman E, Fisher PB (1994). Induction of differentiation in human promyelocytic HL–60 leukemia cells activates p21, WAF1/CIP1, expression in the absence of p53. *Oncogene* 9(11):3397–3406.

Medrano EE, Yang F, Boissy R, Farooqui J, Shah V, Matsumoto K, Nordlund JJ, Park HY (1994). Terminal differentiation and sensescence in the human melanocyte: repression of tyrosine–phosphorylation of the extracellular signal–regulated kinase 2 selectively defines the two phenotypes. *Mol Biol Cell* 5(4):497–509.

Py B, Causton H, Mudd EA, Higgins CF (1994). A protein complex mediating mRNA degradation in *Escherichia coli. Mol Microbiol* 14:717–729.

Sierra JM, Zapata JM (1994). Translational regulation of the heat shock response. *Mol Biol Rep* 19:211–220.

Steinman RA, Hoffman B, Iro A, Guillouf C, Liebermann DA, el–Houseini ME (1994). Induction of p21 (WAF–1/CIP1) during differentiation. *Oncogene* 9(11):3389–3396.

Jiang H, Fisher PB (1993). Use of a sensitive and efficient subtraction hybridization protocol for the identification of genes differentially regulated during the induction of differentiation in human melanoma cells, *Mol Cell Different* 1:285–299.

Jiang H, Su ZZ, Boyd J, Fisher PB (1993). Gene expression changes associated with reversible growth suppression and the induction of terminal differentiation in human melanoma cells. *Mol Cell Different* 1:41–66.

Jiang H, Waxman S, Fisher PB (1993). Regulatoin of c–fos, c–jun and jun–B gene expression in human melanoma cells induced to terminally differentiate. *Mol Cell Different* 1:197–214.

Blau HM (1992). How cells know their place. *Nature* 358:284–285.

Blau HM (1992). Differentiation requires continuous active control. *Annu Rev Biochem* 61:1213–1230.

Campisi J (1992). Gene expression in quiescent and senescent fibroblasts. *Ann N Y Acad Sci* 663:195–201.

Irving J, Feng J, Wistrom C. Pikaart M, Villeponteau B (1992). An altered repertoire of fos/jun (AP–1) at the onset of replicative senescence. *Exp. Cell Res* 202(1):161–166.

Cawthon RM, Anderson LB, Buchberg AM, Xu GF, O'Connell P, Viskochil D, Weiss RB, Wallace MR, Marchuk DA, Culver M et al. (1991). cDNA sequence and genomic structure of EV12B, a gene lying within an intron of the neurofibromatosis gene. *Genomics* 9(3):446–460.

Deutscher MP, Reuven NB (1991). Enzymatic basis for hydrolytic versus phosphorolytic mRNA degradation in *Escherichia coli* and *Bacillus subtilis. Proc Natl Acad Sci USA* 88:3277–3280.

Dubnau D (1991). The regulation of genetic competence in *Bacillus subtilis. Mol Microbiol* Jan. 1991;5(1):11–18.

Murano S, Thweatt R, Schmookler Reis RJ, Jones RA, Moerman EJ, Goldstein S (1991). Diverse gene sequences are overexpressed in werner syndrome fibroblasts undergoing premature replicative senescence. *Mol Cell Biol* 11(8):3905–3914.

Robinow S, White K (1991). Characterization and spatial distribution of the ELAV protein during *Drosophila melanogaster* development. *J Neurobiol* 22:443–461.

Szabo A, Dalmau, J, Manley G, Rosenfeld M, Wong E, Henson J, Posner JB, Furneaux HM (1991). HuD, a paraneoplastic encephalomyelitis antigen, contains RNA–binding domains and is homologous to Elav and Sex–lethal. *Cell* 67:325–333.

Goldstein S (1990). Replicative senescence: the human fibroblast comes of age. *Science* 249(4973):1129–1133.

June CH, Fletcher MC, Ledbetter JA, Schieven GL, Siegel JN, Phillips AF, Samelson LE (1990) Inhibition of tyrosine phosphorylation prevents T–cell receptor–mediated signal transduction. *Proc Natl Acad Sci U S A* 87:7722–7726.

Sorge J, Gross E, West C, Beutler E (1990). High level transcription of the glucocerebrosidase pseudogene normal subjects and patients with Gaucher disease. *J Clin Invest* 86(4):1137–1141.

Mackie GA (1989). Stabilization of the 3' one–third of *Escherichia coli* ribosomal protein S20 mRNA in mutants lacking polynucleotide phosphorylase. *J Bacteriol* 171:4112–4120.

Wright WE, Pereira–Smith OM, Shay JW (1989). Reversible cellular senescence: implications for immortalization of normal human diploid fibroblasts. *Mol Cell Biol* 9(7):3088–3092.

Lee WM, Lin C. Curran T (1988). Activation of the transforming potential of the human fos proto–oncogene requires message stabilization and results in increase amounts of partially modified fos protein. *Mol Cell Biol* 8(12):5521–5527.

Manley JL (1988). Polyadenylation of mRNA precursors. *Biochim Biophys Acta* 950:1–12.

Chomczynski P, Sacchi N (1987). Single–step method of RNA isolation by acid guanidinium thiocyante–phenol–chloroform extraction. *Anal Biochem* 162(1):156–159.

Deng XW, Gruissem W (1987). Control of plastid gene expression during development: the limited role of transcriptional regulation. *Cell* 49:379–387.

Caput D, Beutler B, Hartog K, Thayer R, Brown–Shimer S, Cerami A (1986). Identification of a common nucleotide sequence in the 3'–untranslated region of mRNA molecules specifying inflammatory mediators. *Proc Natl Acad Sci USA* 83(6):1670–1674.

Donovan WP, Kushner SR (1986). Polynucleotide phosphorylase and ribonuclease II are required for cell viability and mRNA turnover in *Escherichia coli* K–12. *Proc Natl Acad Sci U S A* 83:120–124.

Shaw G, Kamen R (1986). A conserved Au sequence from the 3' untranslated region of GM–CSF mRNA mediates selective mRNA degradation. *Cell* 46(5):659–667.

Blau HM, Pavlath GK, Hardeman EC, Chiu CP, Silberstein L, Webster SG, Miller SC, Webster C (1985). Plasticity of the differentiated state. *Science* 230:758–766.

Fisher PB, Grant S (1985). Effects of interferon on differentiation of normal and tumor cells. *Pharmacol Ther* 27(2):143–166.

Fisher PB, Prignoli DR, Hermo H, Jr., Weinstein IB, Pestka S (1985). Effeects of combined treatment with interferon and mezerein on melanogenesis and growth in human melanoma cells. *J Interferon Res* 5(1):11–22.

Kashima N, Nishi–Takaoka C, Fujita T, Taki S, Yamada G, Hamuro J, Taniguchi T (1985). Unique structure of murine interleukin–2 as deduced from cloned cDNAs. *Nature* 313(6001):402–404.

Nedwin GE, Maylor SL, Sakaguchi AY, Smith D, Jarrett–Nedwin J, Pennica D, Goeddel DV, Gray PW (1985). Human lymphotoxin and tumor necrosis factor genes: structure, homology and chromosomal localization. *Nucleic Acids Res* 13(17):6361–6373.

Wong GG, Witek JS, Temple PA, Wilkens KM, Leary AC, Luxenberg DP, Jones SS, Brown EL, Kay RM, Orr EC, et al. (1985). Human GM–CSF: molecular cloning of the complementary DNA and purification of the natural and recombination proteins. *Science* 228(4701):810–815.

Miller AD, Curran T, Verma IM (1984). Deletion of the gag region from FBR murine osteosarcoma virus does not affect its enhanced transforming activity. *Cell* 36:51–60.

Tseng SC, Savion N, Gospodaroicz D, Stern R (1983). Modulation of collagen synthesis by a growth factor and by the extracellular matrix: comparison of cellular response to two different stimuli, *J Cell Biol* 97:803–809.

van Straaten F, Muller R, Curran T, Van Beveren C, Verma IM (1983). Complete nucleotide sequence of a human c–onc gene: deduced amino acid sequence of the human c–fos protein. *Proc Natl Acad Sci USA* 80(11):3183–3187.

Goeddel DV, Leung DW, Dull TJ, Gross M, Lawn RM, McCandliss R, Seeburg PH, Ullrich A, Yelverton E, Gray PW (1981). The structure of eight distinct cloned human leukocyte interferon cDNAs. *Nature* 290(5801):20–26.

Hayflick L, Moorehead PS (1961). The serial cultivation of human diploid cell strains. *Exp Cell Res* 25:585–621.

* cited by examiner

FIG. 1
1 2 3 4 5 6
 1 day exposure
 4 hours
 1 hour
 EtBr

FIG. 2A
A  IFN-β
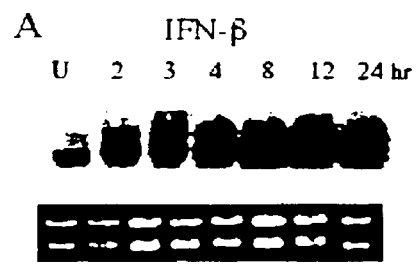
FIG. 2B
B  Dose response to IFN-β
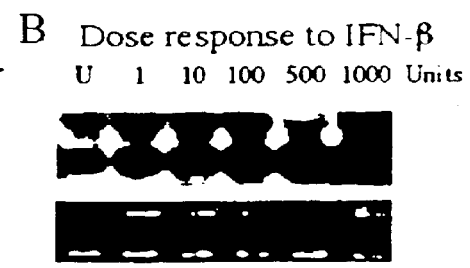
C  IFN-αβγ and TNF-α
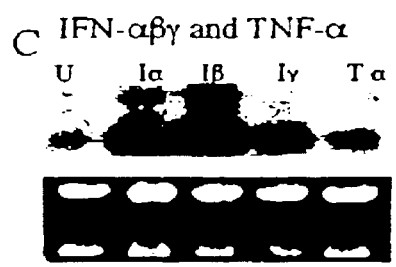
D  IFN-β + MEZ
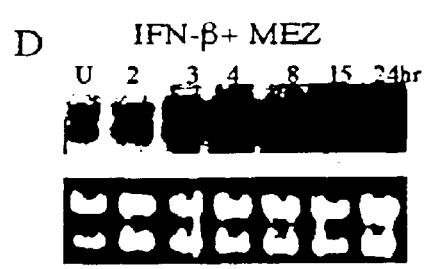
EtBr
FIG. 2C          FIG. 2D

FIG. 3A Human Multiple Tissue Northern Blot
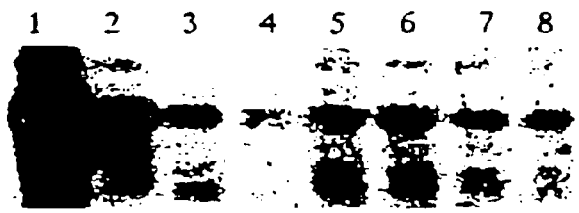
FIG. 3B Mouse Development
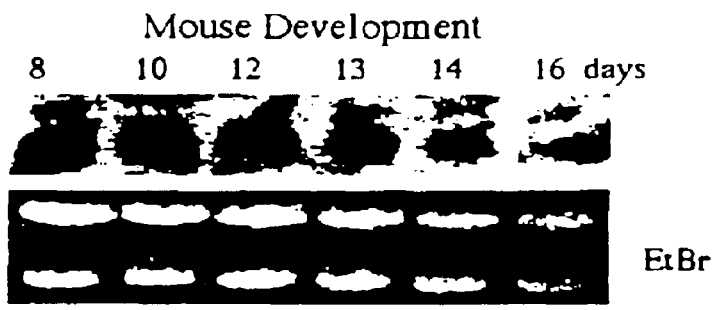

FIG. 4A

```
human      TTGAAGATTACAATGGTGACATGGACTTCAAAATAGCTGG        40
mouse      ..........AATGGTGACATGGATTTCAAAATAGCCGG        29
Consensus            aatggtgacatgga ttcaaaatagc gg human      CACTAATAAAGGAATAACTGCATTACAGGCTGATATTAAA        80
mouse      TACAAATAAAGGAATAACTGCATTACAGGCTGATATTAAG        69
Consensus   ac aataaaggaataactgcattacaggctgatattaa human      TTACCTGGAATACCAATAAAAATTGTGATGGACGCTATTC       120
mouse      TTACCTGGAGTACCAATTAAAATTATAATGGAAGCCATCC       109
Consensus  ttacctgga  taccaat aaaatt t atgga gc at c human      AACAAGCTTCAGTGGCAAAAAAGGAGATATTACAGATCAT       160
mouse      AACAAGCGTCAGTGGCAAAGAAGGAGATACTGCAGATAAT       149
Consensus  aacaagc tcagtggcaaa aaggagata t cagat at human      GAACAAAACTATTTCAAAACCTCGAGCATCTAGAAAAGAA       200
mouse      GAACAAAACGATTTCAAAACCTCGAGCATCAAGAAAAGAA       189
Consensus  gaacaaaac atttcaaaacctcgagcatc agaaaagaa human      AATGGACCTGTTGTAGAAACTGTTCAGGTTCCATTATCAA       240
mouse      AATGGACCAGTTGTAGAAACASTAAGGTTCCATTATCAA       229
Consensus  aatggacc gttgtagaaac gt  aggttccattatcaa human      AACGAGCAAAATTTGTTGGACCTGGTGGCTATAACTTAAA       280
mouse      AACGAGCAAAATTCGTTGGCCCTGGTGGATATCACTTAAA       269
Consensus  aacgagcaaaatt gttgg cctggtgg tat acttaaa human      AAAACTTCAGGCTGAAACAGGTGTAACTATTAGTCAGGTG       320
mouse      AAAACTCCAGGCTGAGACAGGTGTAACAATTAGTCAGGTT       309
Consensus  aaaact caggctga acaggtgtaac attagtcaggt human      GATGAAGAAACGTTTTCTGTATTTGCACCAACACCCAGTG       360
mouse      GATGAAGAAACCTTCTCCATATTTGCACCAACACCTACTG       349
Consensus  gatgaagaaac tt tc  tatttgcaccaacacc a tg human      TTATGCATGAGGCAAGAGACTTCATTACTGAAATCTGCAA       400
mouse      CAATGCATGAAGCAAGAGATTTCATTACAGAAATTTGCAG       389
Consensus    atgcatga gcaagaga ttcattac gaaat tgca human      GGATGATCAGGAGCAGCAATTAGAATTTGGAGCAGTATAT       440
mouse      AGATGATCAAGAGCAACAATTAGAATTTGGAGCAGTTTAT       429
Consensus   gatgatca gagca caattagaatttggagcagt tat human      ACCGCCACAATAACTGAAATCAGAGATACTGGTGTAATGG       480
mouse      ACCGCGACAATAACTGAAATCAGAGACACTGGAGTGATGG       469
Consensus  accgc acaataactgaaatcagaga actgg gt atgg
```

FIG. 4B

```
human      TAAAATTATATCCAAATATGACTGCGGTACTGCTTCATAA   520
mouse      TAAAACTGTATCCAAACATGACTGCAGTGCTGCTTCATAA   509
Consensus   taaaa t tatccaaa atgactgc gt ctgcttcataa human      CACACAACTTGAT.AACGAAAGATTAAACATCCTACTGCC   559
mouse      TTCACAACTTGACCAACGAAAGATTAAACATCCCACTGCC   549
Consensus    cacaacttga  aacgaaagattaaacatcc actgcc human      CTAGGATTAGAAGTTGGCCAAGAAATTCAGGTGAAATACT   599
mouse      CTAGGACTAGAGGTTGGCCAAGAAATTCAGGTCAAATACT   589
Consensus  ctagga taga gttggccaagaaattcaggt aaatact human      TTGGACGTGACCCAGCCGATGGAAGAATGAGGCTTTCTCG   639
mouse      TTGGCCGTGATCCAGCTGATGGAAGAATGAGGCTTTCTCG   629
Consensus  ttgg cgtga ccagc gatggaagaatgaggctttctcg human      AAAAGTGCTTC                                650
mouse      TAAAGTACTTC                                640
Consensus   aaagt cttc
```

FIG. 7

Hu GM-CSF  UAAUAUUUAUAUAUUUAUAUUUUAAAAUAUUUAUUUAUUUAUUUAA

Hu IFN-α  UAUUUAUUUAA

Hu Il 2  UAUUUAUUUAAAUAUUUAAAUUUUAUAUUUAAU

Hu TNF  AAUUAAUUUAUUAUUUUAUUUAUUAUUUUAUUUAUU

C-fos  GUUUUUAAUUUAUUUAUUAAGAUGGAUUCUCAGAUAUUUAUAUUUUU
AUUUUAUUUUUUU

Old-35  AUUUACAUGUGCCAUUUUUUUAAUUCGAGUAACCCAUAUUUGUUUAAUU
GUAUUUACAUUAUAAAUCAAGAAAUAUUUAUUAUUAAAAGUAAGUC
AUUUAUACAUCUUAGA

Response of Old-35
To IFN-β Treatment
In the Presence of Cyclohexamide

Half-life of Old-35 in IFN-β+MEZ
Treated HO-1

FIG. 9A

```
GATGGTCCTT TCCTTCTGCC ACGGCGGGAT CGGGCACTCA CCCAGTTGCA
AGTGCGAGCA CTATGGAGTA GCGCAGGGTC TCGAGCTGTG GCCGTGGACT
TAGGCAACAG GAAATTAGAA ATATCTTCTG GAAAGCTGGC CAGATTTGCA
GATGGCTCTG CTGTAGTACA GTCAGGTGAC ACTGCAGTAA TGGTCACAGC
GGTCAGTAAA ACAAAACCTT CCCCTTCCCA GTTTATGCCT TTGGTGGTTG
ACTACAGACA AAAAGCTGCT GCAGCAGGTA GAATTCCCAC AAACTATCTG
AGAAGAGAGG TTGGTACTTC TGATAAAGAA ATTCTAACAA GTCGAATAAT
AGATCGTTCA ATTAGACCGC TCTTTCCAGC TGGCTACTTC TATGATACAC
AGGTTCTGTG TAATCTGTTA GCAGTAGATG GTGTAAATGA GCCTGATGTC
CTAGCAATTA ATGGCGCTTC CGTAGCCCTC TCATTATCAG ATATTCCTTG
GAATGGACCT GTTGGGGCAG TACGAATAGG AATAATTGAT GGAGAATATG
TTGTTAACCC AACAAGAAAA GAAATGTCTT CTAGTACTTT AAATTTAGTG
GTTGCTGGAG CACCTAAAAG TCAGATTGTC ATGTTGGAAG CCTCTGCAGA
GAACATTTTA CAGCAGGACT TTTGCCATGC TATCAAAGTG GGAGTGAAAT
ATACCCAACA AATAATTCAG GGCATTCAGC AGTTGGTAAA AGAAACTGGT
GTTACCAAGA GGACACCTCA GAAGTTATTT ACCCCTTCGC CAGAGATTGT
GAAATATACT CATAAACTTG CTATGGAGAG ACTCTATGCA GTTTTTACAG
ATTACGAGCA TGACAAAGTT TCCAGAGATG AAGCTGTTAA CAAAATAAGA
TTAGATACGG AGGAACAACT AAAAGAAAAA TTTCCAGAAG CCGATCCATA
TGAAATAATA GAATCCTTCA ATGTTGTTGC AAAGGAAGTT TTTAGAAGTA
TTGTTTTGAA TGAATACAAA AGGTGCGATG GTCGGGATTT GACTTCACTT
AGGAATGTAA GTTGTGAGGT AGATATGTTT AAAACCCTTC ATGGATCAGC
ATTATTTCAA AGAGGACAAA CACAGGTGCT TTGTACCGTT ACATTTGATT
CATTAGAATC TGGTATTAAG TCAGATCAAG TTATAACAGC TATAAATGGG
ATAAAGATA AAAATTTCAT GCTGCACTAC GAGTTTCCTC CTTATGCAAC
TAATGAAATT GGCAAAGTCA CTGGTTTAAA TAGAAGAGAA CTTGGGCATG
GTGCTCTTGC TGAGAAAGCT TTGTATCCTG TTATTCCCAG AGATTTCCT
TTCACCATAA GAGTTACATC TGAAGTCCTA GAGTCAAATG GGTCATCTTC
TATGGCATCT GCATGTGGCG GAAGTTTAGC ATTAATGGAT TCAGGGGTTC
CAATTTCATC TGCTGTTGCA GGCGTAGCAA TAGGATTGGT CACCAAAACC
GATCCTGAGA AGGGTGAAAT AGAAGATTAT CGTTTGCTGA CAGATATTTT
GGGAATTGAA GATTACAATG GTGACATGGA CTTCAAAATA GCTGGCACTA
ATAAAGGAAT AACTGCATTA CAGGCTGATA TTAAATTACC TGGAATACCA
ATAAAATTG TGATGGAGGC TATTCAACAA GCTTCAGTGG CAAAAAGGA
GATATTACAG ATCATGAACA AAACTATTTC AAAACCTCGA GCATCTAGAA
AAGAAAATGG ACCTGTTGTA GAAACTGTTC AGGTTCCATT ATCAAAACGA
GCAAAATTTG TTGGACCTGG TGGCTATAAC TTAAAAAAAC TTCAGGCTGA
AACAGGTGTA ACTATTAGTC AGGTGGATGA AGAAACGTTT TCTGTATTTG
CACCAACACC CAGTGTTATG CATGAGGCAA GAGACTTCAT TACTGAAATC
TGCAAGGATG ATCAGGAGCA GCAATTAGAA TTTGGAGCAG TATATACCGC
CACAATAACT GAAATCAGAG ATACTGGTGT AATGGTAAAA TTATATCCAA
ATATGACTGC GGTACTGCTT CATAACACAC AACTTGATAA CGAAAGATTA
AACATCCTAC TGCCCTAGGA TTAGAAGTTG GCCAAGAAAT TCAGGTGAAA
TACTTTGGAC GTGACCCAGC CGATGGAAGA ATGAGGCTTT CTCGAAAAGT
GCTTCAGTCG CCAGCTACAA CCGTGGTCAG AACTTTGAAT GACAGAAGTA
GTATTGTAAT GGGAGAACCT ATTTCACAGT CATCATCTAA TTCTCAGTGA
TTTTTTTTTT TTAAAGAGAA TTCTAGAATT CTATTTTGTC TAGGGTGATG
TGCTGTAGAG CAACATTTTA GTAGATCTTC CATTGTGTAG ATTTCTATAT
AATATAAATA CATTTTAATT ATTTGTACTA AAATGCTCAT TTACATGTGC
CATTTTTTA ATTCGAGTAA CCCATATTTG TTTAATTGTA TTTACATTAT
AAATCAAGAA ATATTTATTA TTAAAAGTAA GTCATTTATA CATCTTAGA
```

FIG. 9B

```
DGPFLLPRRD RALTQLQVRA LWSSAGSRAV AVDLGNRKLE ISSGKLARFA
DGSAVVQSGD TAVMVTAVSK TKPSPSQFMP LVVDYRQKAA AAGRIPTNYL
RREVGTSDKE ILTSRIIDRS IRPLFPAGYF YDTQVLCNLL AVDGVNEPDV
LAINGASVAL SLSDIPWNGP VGAVRIGIID GEYVVNPTRK EMSSSTLNLV
VAGAPKSQIV MLEASAENIL QQDFCHAIKV GVKYTQQIIQ GIQQLVKETG
VTKRTPQKLF TPSPEIVKYT HKLAMERLYA VFTDYEHDKV SRDEAVNKIR
LDTEEQLKEK FPEADPYEII ESFNVVAKEV FRSIVLNEYK RCDGRDLTSL
RNVSCEVDMF KTLHGSALFQ RGQTQVLCTV TFDSLESGIK SDQVITAING
IKDKNFMLHY EFPPYATNEI GKVTGLNRRE LGHGALAEKA LYPVIPRDFP
FTIRVTSEVL ESNGSSSMAS ACGGSLALMD SGVPISSAVA GVAIGLVTKT
DPEKGEIEDY RLLTDILGIE DYNGDMDFKI AGTNKGITAL QADIKLPGIP
IKIVMEAIQQ ASVAKKEILQ IMNKTISKPR ASRKENGPVV ETVQVPLSKR
AKFVGPGGYN LKKLQAETGV TISQVDEETF SVFAPTPSVM HEARDFITEI
CKDDQEQQLE FGAVYTATIT EIRDTGVMVK LYPNMTAVLL HNTQLDNERL
NILLP·
```

FIG. 10A

```
B subtilis   ....................MGQEKHVFTIDWAGRTLT          18
human        DGPFLLPRRDRALTQLQVRALWSSAGSRAVAVDLGNRKLE         40
Consensus                                 d      r l B subtilis   VETGQLAKCANGAVMIRYGDTAVLSTATASKEPKPLDFFP         58
human        ISSGKLARFADGSAVVQSGDTAVMVTAVSKTKPSPSQFMP         80
Consensus        g la  a g     gdtav  ta       p p  f p B subtilis   LTVNYEERLYAVGKIPGGFIKREGRPSEKAVLASRLIDRP         98
human        LVVDYRQKAAAAGRIPTNYLRREVGTSDKEILTSRIIDRS        120
Consensus    l v y      a g ip    re  g  s k  l sr idr B subtilis   IRPLFADGFRNEVQVISIVMSVDQNCSSEMAAMFGSSLAL        138
human        IRPLFPAGYFYDTQVLCNLLAVDGVNEPDVLAINGASVAL        160
Consensus    irplf  g       qv      vd           a g s al B subtilis   SVSDIPFEGFIAGVTVGRIDDQFIINPTVDQLEKSDINLV        178
human        SLSDIPWNGPVGAVRIGILDGEYVVNPTRKEMSSSTINLV        200
Consensus    s sdip   gp  v g id       npt         s  nlv B subtilis   VAGT.KDAINVVEAGADEVPEEIMLEAIMFGHEEIKRLIA        217
human        VAGAPRSQIVLLEASAENILQQDFCHAIKVGVKYTQQIIQ        240
Consensus    vag   k    i  ea a           ai  g          i B subtilis   FQEEIVAAVGKER.SEIKLFEIDEELNEKVKALAEEDLLK        256
human        GIQQLVKETGVTKRTPQKLFTPSPEIVKYTHKLAMERLYA        280
Consensus        v   g  k      klf    e            la e l B subtilis   AIQVHEKHAREDAINEVRNAVVAKFEDERDEDTIKQVKQ         296
human        VFTDYEHDKVSRDEAVNKIRLDTEEQLKEKFPEADPYEII        320
Consensus         e              k                   e B subtilis   ILSKLVKNEVRRLITE.EKVRPDGRGVDQIRPLSSEVGLL        335
human        ESFNVVAKEVFRSIVLNEYKRCDGRDLTSLRNVSCEVDMF        360
Consensus        v   ev r  i    e     r dgr      r     s ev B subtilis   PRTHGSGLFTRGQTQALSVCTLGALGDVQILDGLGVEES.        374
human        KTLHGSALFQRGQTQVLCTVTFDSLESGIKSDQVITAING        400
Consensus       hgs lf rgqtq l    t     l                d B subtilis   ...KRFHHYNFPQFSVGETGPMRGPGRREIGHGALGERA         411
human        IKDKNFHIHYEPPYATNDIGKVTGLNRRELGHGALAERA         440
Consensus       k fm hy fp       e g       g   rre ghgal  e a B subtilis   LEPVIPSEKDFPYTVRLVSEVLESNGSTSQASICASTLAM        451
human        LYPVIPR..DFPFTIRVTSEVLESNGSSSMASACGGSLAL        478
Consensus    l pvip    dfp t r  sevlesngs s as c    la
```

FIG. 10B

```
B subtilis   MDAGVPIKAPVAGIAMGLVKSG.......EHYTVLTDIQG    484
human        MDSGVPISSAVAGVAIGLVTKTDPEKGEIEDYRLLTDILG    518
Consensus    md gvpi   vag a glv          e y  ltdi g B subtilis   MEDALGDMDFRVAGTEKGVTALQMDIKIEELSREILEEAL    524
human        IEDYNGDMDFKIAGTNKGITALQADIKLPGIPIKIVMEAI    558
Consensus     ed  gdmdfk agt kg talq dik g    i  ea B subtilis   CQAKKGRMEILNSLATLSESRKELSRYAPKILTMTINPD    564
human        CQASVAKKEILQINNKTISKPRASRKENGVVETVQVPLS    598
Consensus    qqa      eil  m t s r        p  t B subtilis   KIRDVIGPSGKQINRIIEETGVKIDIEQDGTIFISSTDES   604
human        KRAKFVGPGSYNLKRLQAETGVTISQVDEETFSVPAPTPS   638
Consensus    k     gp g    k   etgv i        t       s B subtilis   GNQKSKKIIEDLVREVEVGQLYLSKVKRIEKFGAFVEIFS   644
human        VMHEARDFITEICKDDQEQLEFCAVYTATITEIRDTGVM   678
Consensus         a   i           ql  g v B subtilis   GKDGLVHISELALERVGKVEDVVKIGDEILVKVTEIDKQG   684
human        VKLYPNMTAVLLHNTQLDNERLNILLP.............   705
Consensus    k         l         e B subtilis   RVNLSRKAVLREEKEKEEQQS                      705
human        .....................                      705
Consensus
```

FIGURE 14
The effect of subtypes of IFN-α on Old-35 expression
U αA αB2 αC αD αF αG αH αI αJ αA/D PBL001 TAU β

Old-35 is expressed in the spinal column and the genital area

Localization of Old-35 In HeLa cells

GFP
100X

GFP-hPNPase
40X

GENES DISPLAYING ENHANCED EXPRESSION DURING CELLULAR SENESCENCE AND TERMINAL CELL DIFFERENTIATION AND USES THEREOF

This application claims priority and is a continuation of PCT/US00/02920, filed Feb. 2, 2000, which is a continuation-in-part of U.S. Serial No. 09/243,277, filed Feb. 2, 1999 now Abandoned, the contents of U.S. Ser. No. 09/243,277 are hereby incorporated by reference.

Throughout this application, various publications are referred to by arabic numeral within parentheses. Full citations for these publications are presented immediately before the claims. Disclosures of these publications in their entireties are hereby incorporated by reference into this application in order to more fully describe the state of the art to which this invention pertains.

BACKGROUND OF THE INVENTION

Normal cells cultured in vitro lose their proliferative potential after a finite number of doublings in a process described as cellular senescence (Hayflick and Moorehead, 1976). This phenomenon is not only well-established in human diploid fibroblasts based on the studies of Hayflick and Moorehead (1976), but it has also been validated by investigations using many additional cell types (Goldstein et al., 1990; Murano et al., 1991). These investigations document an inverse correlation between replicative senescence and donor age and a direct relationship between replicative senescence and donor species lifespan (Hayflick and Moorehead, 1976; Goldstein et al., 1990; Murano et al., 1991). In agreement with this association, cells from patients with premature aging syndromes, such as Werner's syndrome and Progeria, achieve a quiescent state much more rapidly than normal human fibroblasts. In this context, if similar senescence related changes occur in normal fibroblasts, albeit with delayed kinetics, these cell systems represent excellent models for studying senescence in vitro and identifying genes relevant to the aging process.

Senescence is characterized by changes in cell morphology, lack of responsiveness to mitogenic stimulation and irreversible growth arrest. However, cells can withdraw from the cell cycle and become non-dividing not only during senescence but also during the processes of DNA damage, apoptosis or terminal differentiation. While senescence is a time-dependent process (Campisi et al., 1995), terminal differentiation can be induced in a variety of cell types by appropriate treatment (Roberts et al., 1999). For example, terminal differentiation can be induced by cAMP treatment in melanocytes (Medrano et al., 1994). Gene expression analysis in terminally differentiated versus senescent melanocytes indicates both similarities and differences (Medrano et al., 1994). Although both pathways result in an elevation in p21 and an inability to phosphorylate ERK2, only the differentiated cells display elevated levels of p27 and the melanocyte-specific transcription factor (MITF) (Medrano et al., 1994; Smith and Pereira-Smith, 1996).

Human melanoma represents an excellent model for studying irreversible growth arrest and terminal differentiation, since these physiological changes can be chemically induced by IFN-β plus mezerein (MEZ) (Fisher et al., 1985; Jiang et al., 1994a). The induction of terminal differentiation in HO-1 human melanoma cells correlates with up-regulation of c-jun, jun-B, $\alpha_5$ Integrin, $\beta_1$ Integrin, fibronectin, HLA Class I, ISG-54, ISG-15 and gro/MSGA as well as down-regulation of c-myc (Jiang et al., 1993a). To define the repertoire of genes differentially expressed during induction of irreversible growth arrest and terminal differentiation in human melanoma cells we have used a rapid and efficient differentiation induction subtraction hybridization (DISH) approach (Jiang and Fisher, 1993). Using this approach alone and in combination with high throughput screening strategies, microchip DNA arrays, a large number of novel genes of potential relevance to growth control and terminal differentiation have been identified and cloned (Jiang et al., 1995a, 1995b; Lin et al., 1996, 1998; Huang et al., 1999).

On the basis of the considerations described above, it is probable that specific differentially expressed genes may be present within a terminally differentiated cDNA library that also display modified expression during cellular senescence. To begin to identify these overlapping genes, a temporally spaced subtracted differentiation inducer treated HO-1 human melanoma library was screened with RNA isolated from senescent human fibroblasts. Such a screening protocol yielded twenty-eight known and ten novel cDNAs. Subsequent Northern and reverse Northern blotting analyses revealed differential expression of specific cDNAs. Expression of one of these cDNAs, Old-35 was restricted to terminal differentiation and senescence. In this context, this gene may contribute to pathways leading to growth arrest, a defining component of senescence and terminal differentiation.

Interferons (IFNs) comprise a family of related cytokines with diverse including antiviral, antiproliferative, antitumor and immunomodulatory activities (Stark et al., 1998; *Roberts et al., 1999). IFN studies have focused on two main areas; one involving the clinical use of IFN for therapeutic purposes (Gutterman, 1994), the other employing the IFN system as a paradigm to study the mammalian JAK/STAT signaling cascade (Darnell et al., 1994) that leads to IFN-stimulated gene (ISG) activation. To date, the most extensively studied ISGs include RNA-activated protein kinase (PKR), the 2'–5' oligoadenylate synthetase and the MX proteins (Stark et al., 1998, *Der et al., 1998).

Post-transcriptional regulation of mRNA levels is a pivotal control point in gene expression. Early response genes, such as cytokines, lymphokines and proto-oncogenes are regulated by a cis-acting adenylate-uridylate-rich element (ARE) found in the 3' untranslated region (UTR) of the mRNA (Caput et al., 1986; Shaw and Kamen, 1988; Chen and Shyu, 1995; Myer et al., 1997). Currently, three classes of destabilizing elements have been identified: AUUUA-lacking elements and AUUUA-containing elements grouped into those with scattered AUUUA motifs (such as proto-oncogenes) and those with overlapping AUUUA motifs (such as growth factors) (Chen et al., 1995; Myer et al., 1997). A transfer of 3'UTR containing ARE to 3'UTR of a stable message, such as β-globin, targets this very stable mRNA for rapid degradation (Shaw and Kamen, 1988). In contrast, the removal of an ARE stabilizes an otherwise labile message (*Miller et al., 1984; *Lee et al., 1988).

The present studies describe the cloning and initial characterization of a novel gene, Old-35, from a terminally differentiated human melanoma cDNA library. mRNA stability studies document that Old-35 mRNA, which contains ARE elements, may be stabilized in H0-1 cells by treatment with IFN-β and IFN-b+MEZ. Based on the growth suppressive effect of IFN-β on HO-1 cells, as well as the increased stability of Old-35 during confluence and senescence, it is possible that this gene plays a prominent role in growth suppression induced by this cytokine. Further experimentation is required to define the precise role of Old-35 in IFN signaling, terminal differentiation and cellular senescence. Full-length cloning and subsequent protein analyses should provide insights into the function of this potentially important gene in the processes of aging and differentiation.

Since the processes of terminal differentiation and senescence exhibit strikingly similar characteristics, it is possible that related and overlapping genes and gene expression changes associate with and mediate both of these phenomena. Old-35 was isolated by screening a subtracted human melanoma cDNA library enriched for genes related to growth arrest and terminal differentiation with RNA from senescent human fibroblasts. This cDNA encodes an IFN-β inducible gene expressed during different types of growth arrest including confluence, senescence and terminal differentiation. Old-35 RNA exhibits increased stability in IFN-β and INF-β+MEZ treated H0-1 human melanoma cells. Steady-state mRNA for Old-35 is also highly expressed in heart and brain, human tissues without active regenerative properties. Judging from the pattern of Old-35 expression, it is possible that this gene may play a prominent role during growth arrest and in this context contributes to the important processes of senescence and terminal differentiation.

SUMMARY OF THE INVENTION

This invention provides isolated nucleic acid molecule encoding an old 35 protein, 64 protein, 137 protein, 139 protein, 142 protein and a 175 protein. The isolated nucleic acid may be a DNA, genomic DNA, cDNA, synthetic DNA or RNA. The isolated nucleic acid has a sequence substantially the same as SEQ ID. Nos. 39, 19, 31, 32, 34 and 38 which are respectively Old 35, old 64, old 137, old 139, old 142 and old 175.

This invention also provides a nucleic acid molecule of at least 15 nucleotides capable of specifically hybridizing with a sequence included within the sequence of a nucleic acid molecule encoding an old 35 protein, 64 protein, 137 protein, 139 protein, 142 protein and a 175 protein. The nucleic acid probe may be DNA, genomic DNA, cDNA, synthetic DNA or RNA.

This invention further provides a host vector system for the production of a protein having the biological activity of old 35, 64, 137, 139, 142 and 175. The isolated old 35, 64, 137, 139, 142 and 175 nucleic acid molecule is linked to a promoter of RNA transcription and then to a plasmid. The suitable host is a bacterial cell, insect cell, or animal cell, depending on the type of promoter and plasmid used. This invention also provides a method of producing a protein having the biological activity of old 35, 64, 137, 139, 142 and 175, which comprises growing the selected host vector system under suitable conditions permitting production of the protein and recovering the protein so produced.

This invention further provides purified protein of old 35, 64, 137, 139, 142 and 175. Such purified old 35, 64, 137, 139, 142 and 175 will be useful for inhibiting growth of cancer cells. This invention provides a method of contacting the cancer cells with an amount of old 35, 64, 137, 139, 142 and 175 at a concentration effective to inhibit growth of cancer cells. This invention further provides a method of determining whether a cell is senescent by (a) isolating the nucleic acids in the cell (b) hybridizing the isolated nucleic acids with the nucleic acid of old 35 or 64 under conditions permitting hybrids formation and (c) detecting the expression of old 35 or old 64 in the cell. This invention further provides a method of determining whether a cell has growth arrest by (a) isolating the nucleic acids in the cell; (b) hybridizing the isolated nucleic acids with the nucleic acid of old 35 or 64 under conditions permitting hybrids formation; and (c) detecting the expression of old 35 or old 64 in the cell. This invention further provides a method of determining whether a cell has terminal differentiation by (a) isolating the nucleic acids in the cell; (b) hybridizing the isolated nucleic acids with the nucleic acid of old 35 or 64 under conditions permitting hybrids formation; and (c) detecting the expression of old 35 or old 64 in the cell. Further, this invention provides that the detector used is a DNA, RNA or protein. This invention also provides a method of regenerating tissue with an inhibitor of old 35 protein at a concentration effective to regenerate said tissues. This invention provides a method of anti-aging in a cell comprising contacting the cell with an agent for inhibiting expression of old 35 at a concentration effective to reverse growth arrest in the cell. Finally, this invention provides a pharmaceutical composition for stimulating cell growth comprising a pharmaceutically acceptable carrier and purified old 35 or old 64 at a concentration effective to stimulate cell growth.

BRIEF DESCRIPTION OF FIGURES

FIG. 1 Expression of Old-35 in H0-1 human melanoma cells treated with IFN-β or FN-β+MEZ, young human fibroblasts and two different types of senescent Progeria human fibroblasts. Northern blot contains 10 µg of total RNA from control untreated HO-1 (lane 1), IFN-β treated (2,000 U/ml) H0-1 (lane 2), IFN-β+MEZ treated (2,00 U/ml+10 ng/ml) H0-1 (lane 3), young fibroblasts (GM01379) (lane 4), and two senescent Progeria cell lines (AG01976) (lane 5) (AG0989B) (lane 6). Blots were exposed for autoradiography for 1, 4 or 24 hr. EtBr staining for quantification of gel loading and determining RNA quality.

FIG. 2 Effect of IFN-α, IFN-β, IFN-γ, TNF-α and IFN-β+MEZ on Old-35 expression in H0-1 cells. All Northern blots contain 10 mg of total RNA. (A) Time course induction of Old-35 by IFN-β in H0-1 cells. Cells were seeded at ~60% confluence and treated with IFN-β (2,000 units/ml) and RNA was isolated at the indicated time. U=RNA from control, untreated cells. (B) Dose response expression of Old-35 in H0-1 cells treated with IFN-β (2,000 units/ml). RNAs were isolated after 24 hr treatment. (C) Effect of IFN-α (Iα), IFN-β (Iβ), IFN-γ (Iγ) and TNF-α (Tα) on Old-35 expression in H0-1 cells. RNAs were isolated after 15 hr treatment with 1,000 units/ml of the different agents. U=RNA from control, untreated cells. (D) Time course induction of Old-35 by IFN-β+MEZ in H0-1 cells. RNAs were isolated from cells treated with 2,000 units/ml of IFN-β+10 ng/ml of MEZ.

FIG. 3 Expression of Old-35 in various human tissues and during mouse development. (A) Northern blot contains 2 µg of poly A$^+$ RNA per lane from eight different human tissues. Lanes 1–8 contain, in order, RNA from human heart, brain, placenta, lung, liver, skeletal muscle, kidney, and pancreas (Clontech). (B) Northern blot contains 10 µg of total RNA from mouse embryos. The number of days signifies days post-gestation.

FIG. 4 (A–B) Sequence comparison between human and the mouse homologue of Old-35. Upper panel sequence of human Old-35 (h-Old-35; SEQ ID NO.: 40); Middle Panel: sequence of mouse Old-35 (m-Old-35SEQ ID NO.: 41); and Lower panel: shared consensus sequences between human and mouse Old-35.

FIG. 7 AU rich sequences found in the 3' untranslated region (UTR) of several lymphokine and protooncogene mRNAs. Abbreviations: Hu=human, GM-CSF= granulocyte-monocyte colony stimulating factor; IFN-α= interferon α; IL 2=Interleukin 2; TNF=tumor necrosis factor; c-fos=fos proto-oncogene. The underlined/overlined AUUUA motif if the largest sequence common to all mRNAs is shown. References: HuGM-CSF (SEQ ID NO.: 46) (Wong et al., 1985), Hu IFN-α (SEQ ID NO.: 47) (Goeddel et al., 1983), Hu IL 2 (SEQ ID NO.: 48) (Kashima et al., 1985), Hu TNF (SEQ ID NO.:51) (Nedwin et al., 1985), Hu c-fos (SEQ ID NO.:49) (van Straaten et al., 1983), Old 35 (SEQ ID NO.:50).

FIG. 9 DNA sequence and predicted encoded protein of Old-35. (A) cDNA sequence of Old-35 (SEQ ID NO.:39). Alternate polyadenylation site is underlined. This site is present in 10% of all cDNAs (Manley et al., 1988). (B) Predicted protein encoded by the Old-35 cDNA (SEQ ID NO.:42).

FIG. 10A and B: Sequence similarity between the bacterial protein PNPase and the predicted protein sequence of Old-35. Upper sequence *Bacillus subtilis* PNPase sequence (SEQ ID NO:43). Middle sequence: predicted human Old-35 sequence (SEQ ID NO:44). Lower sequence: regions of consensus amino acids between the bacterial PNPase protein sequence and the predicted Old-35 protein sequence (SEQ ID NO:45). Black boxed areas indicate amino acid identity and gray boxed areas indicate amino acid similarities between the bacterial PNPase and the predicted Old-35 encoded protein. Panel A: N-terminal portions of *Bacillus subtilis* PNPase (amino acid residues 1–451) and the human protein predicted from the human Old-35 cDNA sequence (amino acids 1–478). Panel B. C-terminal portions of *Bacillus subtilis* PNPase (amino acid resudues 452–705) and the human protein predicted from the human Old-35 cDNA sequence (amino acids 479–705).

FIG. 14 Localization of GFP-Old-35, and GFP alone in HeLa cells.

DETAILED DESCRIPTION OF THE INVENTION

Figure 5:
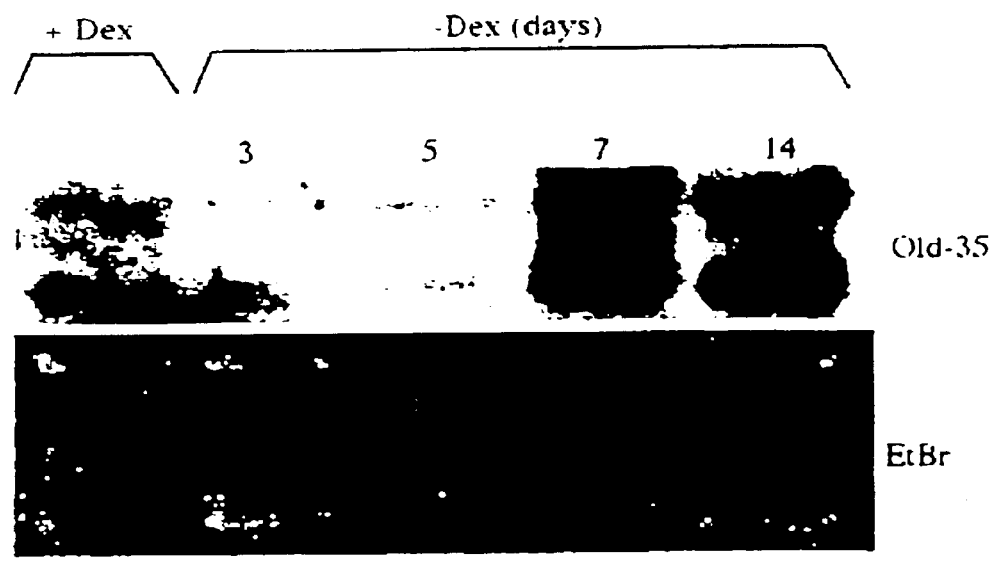
FIG. 5 Expression of Old-35 in IDH4 cells grown in the presence or absence of Dex. Northern blot contains 10 µg of total RNA per lane from IDH-4 cells. +Dex=cells grown continuously in the presence of $10^{-6}$ M Dex; −Dex=cells grown for the indicated days in the absence of Dex. For the latter experiment, cells were grown in the presence of Dex and then shifted to charcoal stripped media and grown for 3, 5, 7 and 14 days without Dex.

In order to facilitate an understanding of the Experimental Details section which follows, certain frequently occurring methods and/or terms are described in Sambrook, et al. (1989).

Throughout this application, the following standard abbreviations are used throughout the specification to indicate specific nucleotides:

C = cytosine
T = thymidine
A = adenosine
G = guanosine

This invention provides an isolated nucleic acid molecule encoding an OLD-35 or OLD-64 protein. In an embodiment, the above nucleic acid molecule comprises a nucleic acid having a sequence substantially the same as set forth in SEQ. ID. No.39 or 19.

This invention also provides isolated nucleic acid molecules encoding an OLD-137, OLD-139, OLD-142, or OLD-175 protein. In an embodiment, the nucleic acid comprises a nucleic acid having a sequence substantially the same as set forth in SEQ. ID. Nos.31, 32, 34 or 38. The above-described nucleic acid may be DNA, genomic DNA, cDNA, synthetic DNA, or RNA.

This invention also encompasses nucleic acid which encode amino acid sequences which differ from those of OLD-35, OLD-64, OLD-137, OLD-139, OLD-142 or OLD-175, but which should not produce phenotypic changes. Alternatively, this invention also encompasses DNAs and cDNAs which hybridize to the DNA and cDNA of the subject invention. Hybridization methods are well known to those of skill in the art.

The DNA molecules of the subject invention also include DNA molecules coding for protein analogs, fragments or derivatives of antigenic proteins which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the proteins) and which share some or all properties of naturally-occurring forms. These sequences include: the incorporation of codons "preferred" for expression by selected non-mammalian host; the provision of sites for cleavage by restriction endonuclease enzymes; and the provision of additional initial, terminal or intermediate DNA sequences that facilitate construction of readily expressed vectors.

The nucleic acid molecule described and claimed herein are useful for the information which they provide concerning the amino acid sequence of the protein and as products for the large scale synthesis of the protein by a variety of recombinant techniques. The molecule is useful for generating new cloning and expression vectors, transformed and transfected procaryotic and eukaryotic host cells, and new and useful methods for cultured growth of such host cells capable of expression of the protein and related products.

The invention also provides fragments or portion of the Old gene or protein wherein the biological activity of said gene product is maintained. Such fragment or portion may join to other amino acid sequence to create a multi-functional molecule. It is within the ordinary skill to determine such biologically active fragment or portion. A trimming experiment may be performed to define said fragment of portion.

Old-35, Old-64, Old-137, Old-139, Old-142 or Old-175 may be isolated in a variety of vertebrates. In an embodiment, a human Old-35, Old-64, Old-137, Old-139, Old-142 and Old-175 are isolated.

The isolated nucleic molecule of Old-35, Old-64, Old-137, Old-139, Old-142 and Old-175 are represented respectively by SEQ. ID. Nos. 39, 19, 31, 32, 34 and 38.

This invention provides a nucleic acid molecule of at least 15 nucleotides capable of specifically hybridizing with a sequence included within the sequence of a nucleic acid molecule encoding a Old-35, Old-64, Old-137, Old-139, Old-142 or Old-175. In an embodiment, the nucleic acid is DNA, genomic DNA, cDNA, synthetic DNA or RNA.

As used herein, the phrase "specifically hybridizing" means the ability of a nucleic acid molecule to recognize a nucleic acid sequence complementary to its own and to form double-helical segments through hydrogen bonding between complementary base pairs. The nucleic acid molecule will be specific to said Old genes i.e. under appropriate conditions, the molecule will only hybridize with said old gene and no other genes. Said molecule may contain an unique sequence of said Old gene.

Nucleic acid probe technology is well known to those skilled in the art who will readily appreciate that such probes may vary greatly in length and may be labeled with a detectable label, such as a radioisotope or fluorescent dye, to facilitate detection of the probe.

Probe molecules may be produced by insertion of a nucleic acid molecule which encodes OLD-35, OLD-64, OLD-137, OLD-139, OLD-142 or OLD-175 protein or a fragment thereof into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

The probes are useful for 'in situ' hybridization to locate tissues which express this gene, or for other hybridization assays for the presence of this gene or its mRNA in various biological tissues.

The invention also provides an antisense nucleic acid molecule comprising a sequence complementary to the nucleic acid which encodes OLD-35, OLD-64, OLD-137, OLD-139, OLD-142 or OLD-175 protein or a fragment thereof. In an embodiment, the antisense nucleic acid molecule is capable of inhibiting the expression of the hybridized gene.

This invention also provides the above-described isolated nucleic acid molecule operatively linked to a promoter of RNA transcription. This invention further provides a vector which comprises the above-described isolated nucleic acid molecule.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a protein having the biological activity of OLD-35, OLD-64, OLD-137, OLD-139, OLD-142 or OLD-175 protein or a fragment thereof.

This invention further provides an isolated DNA, genomic DNA, cDNA, synthetic DNA or RNA molecule described hereinabove wherein the host cell is selected from the group consisting of bacterial cells (such as *E.coli*), yeast cells, fungal cells, insect cells and animal cells. Suitable animal cells include, but are not limited to Vero cells, HeLa cells, Cos cells, CV1 cells and various primary mammalian cells.

This invention provides a purified, OLD-35 protein, a purified, OLD-64 protein, a purified, OLD-137 protein, a purified, OLD-139 protein, a purified, OLD-142 protein, and a purified, OLD-175 protein.

This invention also provides a protein encoded by the above-described isolated nucleic acid molecule.

This invention also provides an antibody or antigen-binding fragment thereof that specifically binds to OLD-35, OLD-64, OLD-137, OLD-139, OLD-142 or OLD-175 protein. In an embodiment, the antibody is a monoclonal antibody.

Polyclonal antibodies against these proteins may be produced by immunizing animals using selected peptides determined from the decoded amino acid sequences. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of the OLD proteins in living animals, in humans, or in biological tissues or fluids isolated from animals or humans.

This invention provides a method of inhibiting growth of cancer cells comprising contacting the cancer cells with an amount of purified OLD-35, OLD-64 protein or a portion thereof effective to inhibit growth of cancer cells.

This invention also provides a method for reversing the cancerous phenotype of a cancer cell which comprises introducing a nucleic acid comprising an Old-35 or Old-64 gene or a portion thereof into the cell under conditions permitting the expression of the gene so as to thereby reverse the cancerous phenotype of the cell.

This invention provides a method for reversing the cancerous phenotype of a cancer cell in a subject which comprises introducing a nucleic acid molecule comprising an Old-35 or Old-64 gene or a portion thereof into the subject's cancerous cell under conditions permitting expression of the gene in the subject's cell so as to thereby reverse the cancerous phenotype of the cell.

In an embodiment of the method, the nucleic acid molecule comprises a vector. In a further embodiment, the Old-35 or Old-64 gene is linked to a regulatory element such that its expression is under the control of the regulatory element. In a still further embodiment, the regulatory element is a tissue specific regulatory element. In a still further embodiment, the regulatory element is inducible or constitutive. Inducible regulatory element like an inducible promoter is known in the art. Regulatory element such as promoter which can direct constitutive expression is also known in the art.

In a separate embodiment, the regulatory element is a tissue specific regulatory element. The expression of the inserted gene will then be tissue-specific.

Methods to introduce a nucleic acid molecule into cells have been well known in the art. Naked nucleic acid molecule may be introduced into the cell by direct transformation. Alternatively, the nucleic acid molecule may be embedded in liposomes. Accordingly, this invention provides the above methods wherein the nucleic acid is introduced into the cells by naked DNA technology, adenovirus vector, adeno-associated virus vector, Epstein-Barr virus vector, Herpes virus vector, attenuated HIV vector, retroviral vectors, vaccinia virus vector, liposomes, antibody-coated liposomes, mechanical or electrical means. The above recited methods are merely served as examples for feasible means of introduction of the nucleic acid into cells. Other methods known may be also be used in this invention.

This invention provides a method for reversing the cancerous phenotype of a cancer cell which comprises introducing OLD-35 or OLD-64 protein or a portion thereof into the cancerous cell so as to thereby reverse the cancerous phenotype of the cell.

This invention provides a method for reversing the cancerous phenotype of a cancer cell in a subject which comprises introducing OLD-35 or OLD-64 protein into the subject's cancerous cell so as to thereby reverse the cancerous phenotype of the cell. In an embodiment, the cancer cell is a breast, cervical, colon, pancreatic, thyroid, skin, brain, prostate, nasopharyngeal, lung, glioblastoma multiforme, lymphoma, leukemia, connective tissue, nervous system cell or basal cell.

This invention further provides a pharmaceutical composition which comprises an amount of a nucleic acid molecule comprising Old-35, Old-64 gene or portion thereof effective to reverse the cancerous phenotype of a cancer cell and a pharmaceutically acceptable carrier. In an embodiment, the nucleic acid molecule comprises a vector. In a further embodiment, the vector is an adenovirus vector, adeno-associated virus vector, Epstein-Barr virus vector, Herpes virus vector, attenuated HIV vector, retrovirus vector or vaccinia virus vector.

This invention also provides a pharmaceutical composition comprising an amount of OLD-35 or OLD-64 protein effective to reverse the cancerous phenotype of a cancer cell and a pharmaceutically acceptable carrier. In an embodiment, the cancer cell is a breast, cervical, colon, pancreatic, thyroid, skin, brain, prostate, nasopharyngeal, lung, glioblastoma multiforme, lymphoma, leukemia, connective tissue, nervous system or basal cell.

In an embodiment of the above methods, the nucleic acid comprises a vector. The vector includes, but is not limited to, an adenovirus vector, adeno-associated virus vector, Epstein-Barr virus vector, Herpes virus vector, attenuated HIV vector, retrovirus vector and vaccinia virus vector.

As used herein, the term "pharmaceutically acceptable carrier" encompasses any of the standard pharmaceutical carriers. The pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In the practice of the method administration may comprise daily, weekly, monthly, hourly or by peak and trough, the precise frequency being subject to various variables such as age and condition of the subject, amount to be administered, half-life of the agent in the subject, area of the subject to which administration is desired and the like.

In connection with the method of this invention, a therapeutically effective amount may include dosages which take into account the size and weight of the subject, the age of the subject, the severity of the symptom, the efficacy of the agent and the method of delivery of the agent. One of ordinary skill in the art would be readily able to determine the exact dosages and exact times of administration based upon such factors.

This invention provides a method of determining whether a cell is senescent comprising measurement of the expression of Old-35 gene, wherein the expression of the Old-35 gene indicates that the cell is senescent. In an embodiment, the expression of the Old-35 gene is measured by the expression of Old-35 specific RNA. In another embodiment, the expression of the Old-35 gene is measured by the expression of the OLD-35 protein.

This invention also provides a method of determining whether a cell is terminally differentiated comprising measurement of the expression of Old-35 gene, wherein the expression of the old-35 gene indicates that the cell is terminally differentiated. In an embodiment, the expression of Old-35 gene is measured by the expression of old-35 specific RNA. In another embodiment, the expression of the Old-35 is measured by the expression of OLD-35 protein.

This invention provides a method of determining whether a cell has growth arrest comprising measurement of the expression of Old-35 gene, wherein the expression of Old-35 gene indicates that the cell has growth arrest. In an embodiment, the expression of the Old-35 gene is measured by the expression of old 35 specific RNA. In another embodiment, the expression of the Old-35 gene is measured by the expression of OLD-35 protein.

This invention provides a-method of inhibiting growth of cancer cells comprising contacting the cancer cells with an amount of purified OLD-64 protein effective to inhibit growth of cancer cells.

This invention also provides a method of inhibiting growth of cancer cells comprising contacting the cancer cells with an amount of purified OLD-64 protein effective to inhibit growth of cancer cells.

This invention provides a method of determining whether a cell is senescent comprising measurement of the expression of old-64 gene, wherein the expression of the Old-64 gene indicates that the cell is senescent. In an embodiment, the expression of old-64 gene is measured by the expression of old-64 specific RNA. In another embodiment, the expression of Old-64 gene is measured by the expression of the OLD-64 protein.

The expression of specific OLD RNA may be measured by the below method: (a) isolating the nucleic acids from a sample; (b) hybridizing the isolated nucleic acids with the appropriate Old gene under conditions permitting hybrids formation; and (c) detecting the hybrid formed.

The invention provides a pharmaceutical composition for inhibiting cell growth comprising a pharmaceutically acceptable carrier and purified old 35 or old 64 at a concentration effective to inhibit cell growth.

This invention provides a method of determining whether a cell is terminally differentiated comprising measurement of the expression of old-64 gene, wherein the expression of the Old-64 gene indicates that the cell is terminally differentiated. In an embodiment, the expression of Old-64 gene is measured by the expression of Old-64 specific RNA. In another embodiment, the expression of Old-64 gene is measured by the expression of the OLD-64 protein.

This invention provides a method of determining whether a cell is growth arrested comprising measurement of the expression of old-64 gene, wherein the expression of Old-64 gene indicates that the cell is growth arrested. In an embodiment, the expression of old-64 gene is measured by the expression of Old-64 specific RNA. In another embodiment, the expression of Old-64 gene is measured by the expression of the OLD-64 protein.

This invention provides a method of regenerating tissues comprising contacting the tissue with an inhibitor of OLD-35 or OLD-64 protein at a concentration effective to regenerate said tissues.

Methods to determine such a concentration are well-known in the art. The effective concentration of said inhibitor of OLD-35 or OLD-64 protein may be determined by using different concentrations of said inhibitor and examine the effect produced.

This invention provides a method of anti-aging in a cell comprising contacting the cell with an agent for inhibiting expression of old-35 or Old-64 gene at a concentration effective to reverse the aging process in the cell.

This invention provides a pharmaceutical composition for stimulating or resuming cell growth comprising a pharmaceutically acceptable carrier and purified Old-35 or Old-64 suppressant at a concentration effective to stimulate or resuming cell growth. A purified suppressant is compound capable of suppressing the activity of OLD-35 or OLD-64. For example, the suppressant can act on the gene level such that no Old-35 or Old-64 gene will be switched on. Alternatively, the suppressant may be a samll molecule capable of binding to the active sites on the OLD-35 or -64 protein such that the protein will not be functional or the activity of the protein will decrease. A specific antibody or its binding fragment, which is capable of binding to the OLD-35 or -64, may be a suppressant.

This invention provides a method for screening the presence of interferon alpha or beta of a sample comprising steps of: (a) contacting the sample with cells under conditions permitting expression of Old-35 or Old-64 gene in the presence of interferon alpha or beta; and (b) determining the expression of Old-35 or Old-64 gene, an increase of expression indicates the presence of interferon alpha or beta.

This invention provides a method for detection of the secretion of interferon alpha or beta comprising steps of: (a) obtaining an appropriate sample from the subject; and (b) detecting expression of Old-35 or Old-64 gene, the expression of Old-35 or Old-64 gene indicating the secretion of interferon in a subject.

This invention provides a method for monitoring chemotherapy of a subject comprising steps of: (a) obtaining an appropriate sample from the subject; and (b) detecting expression of Old-35 or Old-64 gene, the expression of Old-35 or Old-64 gene indicating that the chemotherapy is effective.

This invention provides a method for diagnosis of the proliferating stage of a tumor from a subject comprising steps of:(a) obtaining an appropriate sample from the subject; and (b) detecting expression of Old-35 or Old-64 gene, the expression of Old-35 or Old-64 gene indicating that the tumor is not at a proliferating stage.

This invention also provides a kit for diagnosis of the proliferating stage of a tumor, comprising a nucleic acid molecule capable of specifically hybridizing to the nucleic acid molecule of Old-35 or Old-64.

This invention also provides a kit for diagnosis of the proliferating stage of a tumor, comprising antibody capable of specifically recognizing OLD-35 or OLD-64 protein.

This invention provides different kits containing appropriate reagents to perform the above-described methods.

This invention also provides a method for identifying an agent that modulates the expression of Old-35 or Old-64 gene, comprising: (a)contacting a candidate agent with a cell transformed or transfected with a reporter gene under the control of a Old-35 or Old-64 promoter or a regulatory element thereof under conditions and for a time sufficient to allow the candidate agent to directly or indirectly alter expression of the promoter or regulatory element thereof; and (b) determining the effect of the candidate agent on the level of reporter protein produced by the cell, thereby identifying an agent that modulates expression of Old-35 or 64 gene.

This invention provides a method of identifying compounds that induce proliferation or cancerous phenotype, comprising: exposing cell comprising the promoter of Old-35 or Old-64 to the compound and identifying compounds that suppress the Old-35 or 64 promoter.

This invention provides a method of identifying compounds that induces senescence, or terminal differentiation, comprising: exposing the cell comprising the promoter of Old-35 or Old-64 to the compound and identifying compounds that activate the Old-35 or 64 promoter.

This invention provides a method of identifying genes which are common to the pathway of senescence and terminal differentiation comprising steps of: (a) obtaining a subtracted library which is enriched for genes expressed in terminal differentiation; (b) screening the library with senescent probe to identify novel genes which are expressed during senescence and terminal differentiation; and (c) examining the biological activity of the identified gene to determined whether it is expressed during senescence and terminal differentiation.

This invention provides a method of identifying genes which are common to the pathway of senescence and terminal differentiation comprising steps of: (a) obtaining a subtracted library which is enriched for genes expressed in senescence; (b) screening the library with terminal differentiation probe to identify novel genes which are expressed during senescence and terminal differentiation; and (c) examining the biological activity of the identified gene to determined whether it is expressed during senescence and terminal differentiation.

This invention also provides the gene identified by the above methods.

This invention provides a method of degrading specific RNAs in a cell comprising induction of the expression of Old-35. This invention further provides a method of degrading specific RNAs in a cell comprising introducing a vector into the cell comprising the Old-35 gene.

In one embodiment of the invention, expression of Old-35 can be used as diagnostic indicator of cellular senescence, terminal differentiation and/or growth suppression. Specifically, Old-35 can be used to determine if a cell has lost proliferative ability and thus has become senescent.

In addition, expression of Old-35 can be used as a marker to identify drugs or small molecules that will induce senescence, e.g., to inhibit cancer cell growth or abnormal proliferative states such as psoriasis, hemangioblastoma, etc.

Further, expression of Old-35 can be used to identify drugs or small molecules that will inhibit senescence, and thus stimulate tissue regrowth, repair and/or regeneration.

Still further, expression of Old-35 can be used as a marker to identify drugs or small molecules that will induce terminal cell differentiation, e.g., to inhibit cancer cell growth or abnormal proliferative states such as psoriasis, hemangioblastoma, etc.

Expression of Old-35 can also be used to identify drugs or small molecules that will inhibit terminal differentiation, and thus stimulate tissue regrowth, repair and/or regeneration.

Furthermore, expression of Old-35 can be used as marker for detecting cytokines, specifically type I interferons, in biological samples. Since type I interferons, including leukocyte and fibroblast interferons, which activate gene expression through the well characterized Jak and Stat kinase pathways, this gene (Old-35) can be used to detect or monitor drugs and other small molecules that activate these important pathways.

The combination of Old-35 with other interacting proteins can be used to target the differentiation of specific target cells, and thus result in the reprogramming of pluripotent stem cells to terminally differentiated end cells.

Additionally, old-35 can be used to selectively stabilize specific mRNAs possibly containing AU rich 3' UTRs (untranslated regions). This effect can result in the sustained expression of genes potentiating or inhibiting cell growth. It could also result in the stabilizing of cytokine genes resulting in increased biological and immunological activity.

Old-35 can also be used as part of a methodology to polymerize random NTPs into nucleic acids and/or to induce the degradation of specific mRNAs.

This invention will be better understood from the Experimental Details which follow. However, one skilled in the art will readily appreciate that the specific methods and results discussed are merely illustrative of the invention as described more fully in the claims which follow thereafter.

Experimental Details

Library Screening

A subtracted cDNA library enriched in genes modified during terminal differentiation in human melanoma cells (Jiang and Fisher, 1993) was plated at 200 pfu/plate. Colonies were transferred to Nylon filters, denatured for 2 min (1.5M NaCl, 0.5M NaOH), neutralized for 5 min (1.5M NaCl, 0.5M Tris-HCl, pH 8.0), and washed for 30 sec (0.2M Tris-HCl, pH 7.5, 2×SSC). Filters were cross-linked (120,000 µJ of UV energy) for 30 sec in a Strata linker (Stratagene) and prehybridized at 65° C. for 2 hr in ExpressHyb (ClonTech). The probe was denatured at 95° C. for 5 min, cooled at 0° C. for 5 min and then applied to the filters at $3 \times 10^6$ cpm/ml. The filters were hybridized overnight at 65° C. The next day, the filters were washed (2×SSC, 0.1% SDS) 3× for 20 min and exposed for autoradiography.

Preparation of the Progeria CDNA Probe

Ten µg of total RNA derived from AG0989B cells (Progeria) (p 22) (Corriel Repository, Camden) was reverse transcribed using SuperScript II (manufacturer's protocol, GibcoBRL) except that 900 µCi of [α-$^{32}$P]-dCTP (3000 Ci/mmole) (Amersham) and 0.4 mM of non-radioactive dCTP was used in place of 10 mM dCTP. The probe was purified using Quick Spin Columns (Boehringer Mannheim).

Phage Isolation

The exposed film from autoradiography was aligned with the phage containing plates and hybridizing clones were isolated and re-suspended in SM buffer (1 ml).

PCR

PCR was performed for each phage stock using the manufacturer's protocol (GibcoBRL) with 3 µl of SM stock. Since T3 and T7 primers flank the insert, these primers were used to selectively amplify the insert from the phage vector (Stratagene). PCR conditions were 30 cycles at 94° C. for 1 min, 55° C. for 1 min, 72° C. for 2 min and 72° C. for 10 min to allow complete extension. The PCR products were resolved on 1% agarose gels to determine the size of the product. All clones were sequenced and the novel cDNAs were selected for Northern blotting analysis.

Northern Blotting

Total RNA was extracted using the guanidinium isothiocyanate method followed by phenol/chloroform/isoamyl extraction and precipitation in isopropanol as described in Chomczynski and Sacchi (1987). The probes were labeled with [α-$^{32}$P]dCTP by random priming (Amersham). Ten µg of total RNA were electrophoresed in a 1% agarose/2.2M formaldehyde gel and transferred to Hybond-NX filters (Amersham). Hybridization was performed in ExpressHyb solution (Manufacturer's protocol, Clontech). Briefly, filters were prehybridized at 67° C. for 0.5 hr, hybridized with a denatured probe for 1.5 hr, and washed (0.2×SSC, 0.1% SDS) 1× at 24° C. for 5 min, and 2× at 55° C. for 20 min.

Cells and Culture Conditions

H0-1 human melanoma cells were grown in Dulbecco's modified Eagle's medium (DMEM) supplemented with 5% fetal bovine serum at 37° C. in a 5% $CO_2$/95% air humidified incubator. Cell lines used for the senescence study were obtained from Corriel Repository (Camden, N.J.). Fibroblast cell lines from patients with Progeria-Hutchinson-Gilford Syndrome (AG01972B, AG0989B, AG01178B) and normal fetal fibroblasts (GM01379A) were grown in DMEM supplemented with 15% fetal bovine serum (Gibco BRL) and 2× essential and non-essential amino acids (Sigma). IDH4 cells (Wright et al., 1989) were grown in DMEM supplemented with 10% fetal bovine serum or 10% charcoal stripped fetal bovine serum. HO-1 cells were treated with IFN-β (2,000 U/ml) and MEZ (10 ng/ml) to induce terminal differentiation (Fisher et al., 1985). To inhibit RNA and protein synthesis, HO-1 cells were treated with actinomycin D (5 µg/ml) and cycloheximide (50 µg/ml), respectively, as previously described (Jiang et al., 1993b).

Staining for Senescence-Associated (SA) B-GAL Activity

Cells were washed 2× with PBS, fixed in 3% formaldehyde, and stained as previously described (Dimri et al., 1995). Briefly, following fixation, cells were incubated overnight at 37° C. in a reaction buffer containing X-gal (1 mg/ml), 40 mM citric acid/sodium phosphate (pH 6.0), potassium ferrocyanide/ferricyanide (5 mM), NaCl (150 mM) and 2 mM $MgCl_2$. IDH4 cells grown in the presence of dexamethasone ($10^{-6}$ M) were used as a negative control.

Experimental Results

Preliminary screening of cDNA libraries screening the temporally spaced subtracted differentiation inducer treated H0-1 cDNA (DISH) library enriched for genes regulated during terminal differentiation in melanoma cells, with the RNA from senescent fibroblasts, resulted in the identification of 10 novel and 28 known cDNAs, referred to as Old cDNAs (Table 1). Northern and reverse Northern blotting was used to determine the expression patterns of these Old cDNAs. The goal of our screening was to identify and clone differentially expressed genes common to senescence and terminal differentiation. To achieve this aim, RNAs from H0-1 (untreated or treated with IFN-β, 2,000 U/ml or IFN-β (2,000 U/ml)+MEZ (10 ng/ml)), young fibroblast cultures (GM01379) and two senescent cell cultures (AG01976, AG0989B) were isolated and expression of specific Old genes was determined (FIG. 1). Since the subtracted library that was screened should be enriched for H0-1 genes regulated by IFN-β and IFN-β+MEZ, it was anticipated that the level of expression of many of the Old cDNAs would be reduced or absent in actively proliferating, untreated H0-1 cells. However, since this library was screened with an un-subtracted senescent probe (containing senescent specific, housekeeping and other genes) some of the cDNAs should also be expressed in non-senescent fibroblasts.

Figure 6:
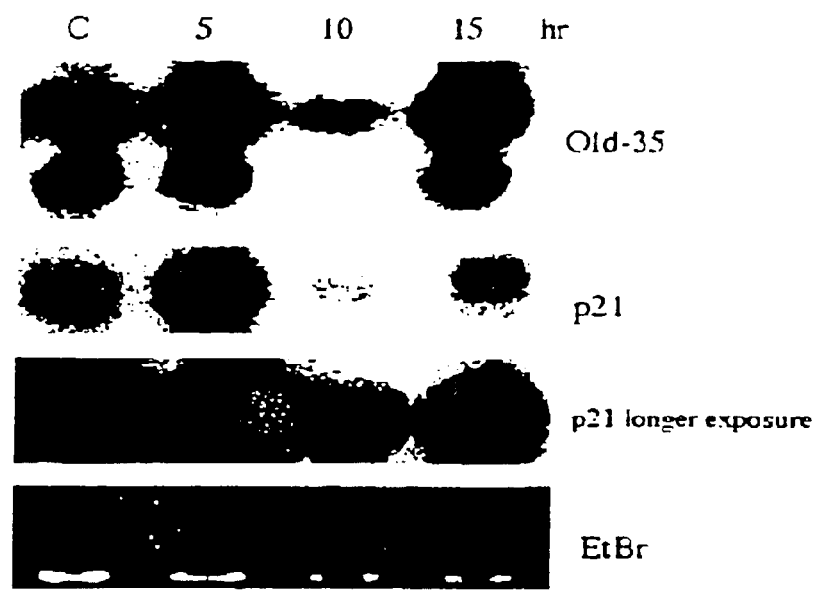
FIG. 6 Expression of Old-35 and p21 during cell cycle progression in human skin fibroblasts. Northern blot contains 10 μg of total RNA per lane from normal human fibroblasts. Confluent normal fibroblasts (C) were trypsinized and reseeded (1:2). Total RNA was collected at 5, 15 and 20 hr after reseeding. At 20 hr following subculture, the cells were 90% confluent.

Four of the six novel cDNAs, Old-137, Old-139, Old-142 and Old-175, were expressed in both proliferating and senescent fibroblasts. Expression of two novel Old genes, Old-35 and Old-64, were restricted to the senescent fibroblasts and IFN-b and IFN-β+MEZ treated H0-1 cells. Different exposure times revealed that the expression level of Old-35 is higher in senescent fibroblasts than in H0-1 cells treated with IFN-β or IFN-β+MEZ (FIG. 1). Response of Old-35 to Interferons Time-course and dose-response experiments were performed in H0-1 cells to determine the temporal kinetics of Old-35 induction by IFN-β and the concentration of IFN-β capable of inducing Old-35 expression, respectively. Additionally, the effect of IFN-α, IFN-γ and TNF-α on Old-35 expression in H0-1 cells was examined. Old-35 was up-regulated by IFN-β (2,000 units/ml) and IFN-β+MEZ (2,000 units/ml+10 ng/ml) within 3 hr of treatment (FIGS. 2A and D). Since IFN-β induces growth suppression in H0-1 cells at 2,000 units/ml, it was considered important to determine whether up-regulation of Old-35 could occur in the absence of growth suppression. Old-35 expression was induced in H0-1 cells with as little as 1 U/ml of IFN-α, a dose of IFN that is not growth inhibitory, suggesting a direct effect of IFN on expression of this gene in the absence of growth suppression (FIG. 2B). Treatment of H0-1 cells with IFN-α resulted in significant up-regulation of Old-35 in H0-1 cells, whereas this expression was marginally stimulated by IFN-γ and no detectable or consistent induction occurred with TNF-α (FIG. 2C). These experiments document differential regulation of Old-35 expression by different cytokines, with type I Interferons (IFN-α/IFN-β) being the most active cytokines tested in inducing Old-35 expression in H0-1 cells. Expression of Old-35 in various human tissues and during mouse development to determine the tissue-specific expression pattern of Old-35 we examined the expression of this gene using Human Multiple Tissue Northern (MTN) Blots (Clontech) (FIG. 3A). Old-35 was expressed in all of the tissues tested, including heart, brain, placenta, lung, liver, skeletal muscle, kidney and pancreas. The highest levels of Old-35 expression were detected in the heart and brain. Since the heart and brain contain a high proportion of non-regenerating, terminally differentiated cells, it is possible that Old-35 may be important in maintaining end stage differentiation in these target organs. Since terminal differentiation of specific tissue cell types occurs during normal development of the embryo, the expression pattern of old-35 was determined during mouse development. The highest level of Old-35 expression was apparent during the earliest stage of development (8 days) and it steadily declined with time (10 to 16 days) (FIG. 3B). This dilution effect is frequently observed when mRNA expression is localized in a specific organ as the embryo develops, because the ratio of the region of expression to the whole body decreases over time. Since the mouse developmental Northern Blot was probed with human cDNA and the resulting signal was very strong, the homology between human and mouse OLD-35 transcripts must be very high. The EST database search showed very close homology between the mouse and the human cDNA, ~90% (FIG. 4). Expression of Old-35 during growth arrest and senescence in IDH4 cell IDH4 cells were produced by transfecting IMR-90, normal human fibroblasts, with a dexamethasone (DEX) inducible mouse mammary tumor virus-driven simian virus 40 T-antigen (Wright et al., 1989). In this model system, prolonged proliferation and the absence of markers of senescence are dependent upon the continued presence of DEX and thus the SV40 T-antigen. (Wright et al., 1989). In DEX-free medium, DNA synthesis declines by ~80% within the first 3 days and reaches a minimum level at day 7. This decline corresponds with a decrease in telomerase activity and T-antigen expression (Holt et al., 1996). Since T-antigen has a long half-life (~3 days) and remains in the cells for about 5–7 days after the removal of DEX, it is possible that the up-regulation of Old-35 by day 7 corresponds with the depletion of T-antigen in these cells (FIG. 5). Further experiments to define relationship between T-antigen expression and Old-35 expression in IDH4 cells are in progress. Old-35 and p21 are coordinately expressed in quiescent cells since many of the genes involved in terminal differentiation and senescence are predominantly active during the $G_1$ phase of the cell cycle, we determined whether Old-35 was expressed at this point of the cell cycle. To achieve this objective, human diploid fibroblasts were grown to confluence (a classic way to arrest and synchronize these cells) (*Tseng et al., 1983). After release of the cells from confluence, following a short lag cells re-entered $G_1$ phase and then the cells traversed though S, $G_2$, M and back to $G_1$. In these cells, Old-35 was highly expressed during the confluence period and at $G_1$ (FIG. 6). Additionally, as more of the cells entered $G_1$ Old-35 expression increased. After 15 hr, Old-35 expression was significantly reduced, but expression increased again when the cells became confluent (20 hr). The expression of p21 ($G_1$ specific cyclin-dependent kinase inhibitor) coincided with the expression of Old-35 (FIG. 6).

Stability of Old-35 in IFN-B Treated Cells

Figure 8A:
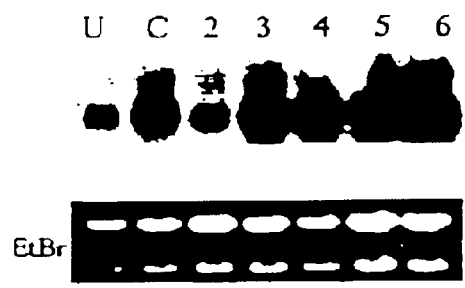
FIG. 8 Effect of cycloheximide treatment on Old-35 expression in H0-1 cells and the half-life of Old-35 mRNA in IFN-β+MEZ treated H0-1 cells. Each lane in the Northern blots contains 10 μg of total RNA. (A) HO-1 cells were pre-treated with cyclohexamide 50 mg/ml for 30 min and then treated with IFN-β for 2, 3 or 4 hr (lanes 2, 3, and 4, respectively). HO-1 cells were pre-treated with IFN-β for 5 hr (lane 5) and then treated with cycloheximide for 15 hr (lane 6). U=RNA from control untreated HO-1 cells. (B) Half-life of Old-35 mRNA in IFN-β+MEZ (IM) (2,000 units/ml+10 ng/ml) treated H0-1 cells. Cells were incubated with IM for 15 hr and then exposed to ActD (50 mg/ml) for 2, 6, 8, 10 and 12 hr. U=RNA from control untreated H0-1 cells. AD=RNA from control H0-1 cells treated with ActD (5 μg/ml).
Figure 8B:
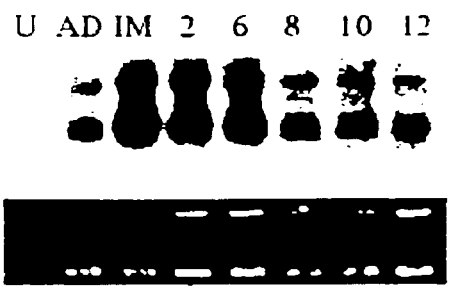

The 3' UTR of particular lymphokines, cytokines and proto-oncogenes contain ARE elements that are implicated in regulating mRNA stability (FIG. 7). The presence of four such ARE elements in the 3' UTR of Old-35 suggests that mRNA stability may contribute to differential expression of this gene under varied treatment and growth conditions. Recently, HuR a protein involved in the destabilization of mRNAs containing ARE elements has been purified and identified as a member of the Elav-line gene family (Myer et al., 1997). If the HuR protein can regulate the stability of Old-35 in HO-1 cells, then treatment of cells with cycloheximide, which inhibits protein synthesis, should decrease or eliminate the HuR protein thereby resulting in stabilization of Old-35 mRNA. Cycloheximide treatment of H0-1 cells (FIG. 8A, lane 2) and IFN-b pre-treated H0-1 cells (FIG. 8A, lane 6 and 7) increases the level of Old-35 mRNA indicating that factors responsible for its degradation might have been inhibited. The cycloheximide studies also indicate that induction of Old-35 expression can occur in the absence of new protein synthesis (FIG. 8A, lanes 3, 4 and 5). However, since Old-35 RNA production in H0-1 cells occurs within 3 hr of treatment, and cycloheximide is present for the entire treatment period, it is possible that modifications of existing proteins may occur prior to changes in Old-35 transcription. Control of mRNA levels in a cell are regulated predominantly at two points: transcription and mRNA stability. To determine if IFN-β+MEZ or IFN-β effect Old-35 mRNA stability in H0-1 cells, the half-life of the Old-35 mRNA was determined as previously described (Jiang et al., 1993b) (FIG. 8B). Untreated and IFN-β+MEZ or IFN-β treated HO-1 cells were incubated with the RNA polymerase II inhibitor Actinomycin D (Act D) and the stability of pre-existing mRNA was determined by Northern blotting. This experiment revealed that the half-life of Old-35 mRNA in H0-1 cells treated with IFN-β+MEZ or IFN-β is ~6–8 hr, suggesting that stabilization of this mRNA may contribute to the elevation of Old-35 levels in treated cells (FIG. 8B and data not shown). However, because of the low level of Old-35 expression in untreated H0-1 cells, it was not possible to accurately determine the half-life of this message in these cells. Whether the observed low levels of Old-35 mRNA in untreated actively proliferating HO-1 cells are the result of a lack of transcriptional activation or mRNA stability still remain to be determined. Nuclear run-on assays, that measure rate of RNA transcription, should reveal whether the promoter is active in HO-1 cells in the absence of IFN-β treatment and the potential contribution of transcriptional activation to elevated Old-35 mRNA following IFN-β and IFN-β+MEZ treatment.

Cloning and Sequence Analysis of Old-35

An initial 600 bp fragment of Old-35 was identified and cloned from a differentiation inducer treated subtracted (DISH) HO-1 cDNA library as described in the library screening protocol. This cDNA was cloned in a pBlueScript vector in the opposite orientation 3'–5' (EcoRI-XhoI) as a result of subtraction hybridization. During the subtraction procedure, cDNAs are excised from the vector by double-digestion with EcoRI and XhoI. Since many cDNA also contain internal EcoRI-XhoI sites, many cDNAs will be cut internally and after the subtraction procedure they will re-ligate in the incorrect direction. Thus the original 600 bp fragment of Old-35 contained an internal region of Old-35 cDNA and lacked 3' and 5' flanking sequences. The 5' region of Old-35 was cloned from IFN-β treated HO-1 cells using a recently developed cDNA extension procedure, complete open reading frame cloning (C-ORF), yielding in a single-reaction an ~2 kb fragment (Kang and Fisher, unpublished). The 3' region of Old-35 was cloned using the 3' RACE procedure with 3' gene specific nested primers and dT, yielding an ~400 bp product. The final sequence of Old-35 is shown in FIG. 9. Although a portion of the 5' may still be missing, the Old-35 cDNA obtained using C-ORF and 3' RACE represents a near full-length clone judging from the Northern blotting data (FIG. 1), in which Old-35 hybridizes with an ~2.4–2.7 kb RNA species. Sequence analysis revealed that the Old-35 cDNA (~2.6 kb) contains a less frequently observed polyadenylation site (AUUAAA) (found in only ~10% of cDNAs) (Manley et al., 1988). The putative protein sequence does not exhibit homology to any known genes except to the *Escherichia coli* PNPase (polyribonucleotide phosphorylase) gene of which 30% of the sequence is homologous and 50% displays sequence similarity (FIG. 10).

Experimental Discussion

Controlled cellular proliferation is paramount for sustaining homeostasis in multicellular organisms. The regulation of this dynamic process is of particular relevance in maintaining a balance between cell loss and cell renewal, important factors in development, differentiation and aging. Moreover, abnormalities in cell division are hallmarks of many disease states, including developmental and congenital birth defects, premature aging syndromes and abnormal proliferative states such as cancer. Several genes involved in cell proliferation control, including the tumor suppressor p53 and the cyclin dependent kinase (cdk) inhibitor p21, display elevated expression in growth suppressive conditions, such as quiescence (Niculescu et al., 1998, Lacombe et al., 1996, Linke et al., 1996), senescence (Irving et al., 1992; Gire and Wynford-Thomas, 1998) and terminal cell differentiation (Jiang et al., 1994b, 1995b; Steinman et al., 1994). Since both terminal differentiation and senescence are characterized by growth arrest, it is possible that similar and overlapping genes and gene expression changes may mediate these processes. To test this hypothesis we have screened a subtracted differentiation inducer treated human H0-1 melanoma library with mRNA derived from senescent human fibroblasts. This approach has resulted in the isolation of a large number of cDNAs, consisting of both known and novel sequences (Table 1), displaying elevated expression in senescent human fibroblasts. Several of the same cDNAs, have also been independently identified from the same subtracted HO-1 library after screening with mRNA isolated from H0-1 cells treated with IFN-b+MEZ that induce irreversible growth arrest and terminal differentiation (Huang et al., 1999). This observation validates our hypothesis and suggests that this novel approach may prove useful in identifying and cloning genes displaying coordinated expression as a function of induction of growth arrest during terminal differentiation and cellular senescence. One such cDNA is the novel gene, Old-35.

Induction of terminal differentiation in human melanoma cells by IFN-β+MEZ frequently results in the induction and up-regulation of genes that also display elevated expression following exposure to IFN-β, referred to as Type I melanoma differentiation associated (mda) genes (Jiang and Fisher, 1993). Old-35 represents such a gene, since its expression is elevated in H0-1 cells after treatment with IFN-β and IFN-β+MEZ. Old-35 is also up-regulated during growth arrest and senescence in human fibroblasts, indicating that its expression is not restricted to only programs of differentiation or to human melanoma cells. Since IFN-β has well-established antiproliferative properties, in both normal and cancer cells (Fisher and Grant, 1985), it is possible that Old-35 may function as a down-stream gene in the IFN-signaling pathway culminating in growth arrest. A number of experiments indicate that old-35 expression is related to cellular senescence and proliferative quiescence. Analysis of Northern blots from young versus senescent human fibroblasts indicates restricted expression of Old-35 to senescent cells. IDH4 cells, conditionally immortalized by a DEX-inducible SV40 T-antigen, represent an excellent in vitro model to study senescence (Wright et al., 1989). The presence of DEX in the growth media allows the IDH4 cells to actively proliferate, while the absence of it causes them to senesce. In these cells, old-35 expression is only detected after 7 days of growth in media devoid of DEX. This expression also corresponds with the SA- (-GAL staining of IDH4 cells, a well-established senescence marker (Dimri et al., 1995). Old-35 expression also increases when fibroblasts become arrested in $G_0$ by growth and maintenance at confluence. In these contexts, Old-35 could prove useful as a diagnostic marker for cellular senescence, terminal differentiation and growth arrest. High levels of Old-35 expression are also found in the brain and heart, the only human tissues that do not possess active regenerative properties. Judging from the localized expression of Old-35 during development, this gene may contribute to heart and brain development by assisting in the maintenance of terminal differentiation of cells in these organs. Due to the high sequence homology of Old-35 to bacterial polyribonucleotide phosphorylase (PNPase), it is possible that Old-35 protein may exhibit a PNPase enzymatic activity. PNPase is one of the critical components of the *Escherichia coli* RNA degradosome (Blum et al., 1997), which consists of both PNPase and endoribonuclease RNase E. The function of this complex is to control the rate of mRNA degradation. The PNPase possesses two enzymatic activities, 3'–5'processive exoribonuclease activity and 5'–3' RNA polymerase activity (Blum et al., 1997). Recently, it has been shown that PNPase also has the capacity to bind to a specific double-stranded DNA sequence in a sequence-specific manner (Zhang et al., 1998). Since Old-35 is differentially expressed in cells that undergo growth arrest, it is possible that this gene may play a role in RNA degradation in growth arrested cells. Additionally, since genes containing AUUUA elements (Myer et al., 1997) have been shown to be involved in the global regulation of gene expression it is possible that Old-35 by binding sequence-specific targets, controls growth related gene expression. In this context, Old-35 might display tumor suppressor properties and could be useful for the gene therapy of cancer.

TABLE 1

| CLONE DESIGNATION | CLONE IDENTITY |
| --- | --- |
| Old-1 (SEQ ID NO.:1) | Vimentin |
| Old-2 (SEQ ID NO.:2) | Human ribosommal protein S3a, v-fos |
| Old-5 (SEQ ID NO.:3) | mRNA M phase phosphoprotein |
| Old-7 (SEQ ID NO.:4) | RIG-G, Cig49 |
| Old-11 (SEQ ID NO.:5) | MHC class I lymphocyte antigen |
| Old-14 (SEQ ID NO.:6) | Human non-muscle myosin alkaline light chain |
| Old-18 (SEQ ID NO.:7) | Human ADP-ribosylation factor 4 |
| Old-19 (SEQ ID NO.:8) | Human mitochondrial cytochrome oxidation |
| Old-24 (SEQ ID NO.:9) | 56 kDa IFN inducible |
| Old-30 (SEQ ID NO.:10) | Ribosommal protein L5 |
| Old-32* (SEQ ID NO.:11) | Novel* |
| Old-34 (SEQ ID NO.:12) | IFN-inducible protein |
| Old-35* (SEQ ID NO.:40) | Novel* |
| Old-38 (SEQ ID NO.:13) | H.s. small acidic protein |
| Old-39 (SEQ ID NO.:14) | Human acidic ribosomal phosphatase |
| Old-42 (SEQ ID NO.:15) | Neurofibromatosis type 1 |
| Old-59 (SEQ ID NO.:16) | Human nuclear receptor hTAK1 |
| Old-60 (SEQ ID NO.:17) | Mitochondrial DNA |
| Old-61 (SEQ ID NO.:18) | Transcription factor I (99%) |
| Old-64* (SEQ ID NO.:19) | Novel* |
| Old-65 (SEQ ID NO.:20) | CDC16HS cell 81, 261–68 |
| Old-74 (SEQ ID NO.:21) | Human ISG 54K gene (IFN-gamma)-cig42 |
| Old-79 (SEQ ID NO.:22) | Human T-complex polypeptide I gene |
| Old-80 (SEQ ID NO.:23) | Vitamin D induced |
| Old-83* (SEQ ID NO.:24) | Novel* |
| Old-87* (SEQ ID NO.:25) | Novel*, Possibly similar to Old-83 |
| Old-107* (SEQ ID NO.:26) | Novel*-Human homologue of Cow G-Protein |
| Old-113 (SEQ ID NO.:27) | DNA binding protein |
| Old-115 (SEQ ID NO.:28) | U1 small nuclear RNP |
| Old-119 (SEQ ID NO.:29) | Human HS1 protein |
| Old-121* (SEQ ID NO.:30) | Novel* |
| Old-137* (SEQ ID NO.:31) | Novel* |
| Old-139 (SEQ ID NO.:32) | Novel* |
| Old-140 (SEQ ID NO.:33) | Human putative trans. CA150 |
| Old-142* (SEQ ID NO.:34) | Novel* |
| Old-144 (SEQ ID NO.:35) | MLN70 calcium-binding |
| Old-165 (SEQ ID NO.:36) | T-cell cyclophilin |
| Old-170 (SEQ ID NO.:37) | Human homologue of rat zinc transporter |
| Old-175(5-3)* (SEQ ID NO.:38) | Novel* |

REFERENCES

Blum E., Py B., Carpousis A. J., and Higgins C. F. (1997). Polyphosphate kinase is a component of the *Escherichia coli* RNA degradosome. *Mol. Microbiol.*, 26: 387–398.

Campisi, J., (1996). Replicative Senescence An Old Lives Tale Cell. *Cell* 84(4):497–500.

Caput D., Beutler B., Hartog K., Thayer R., Brown-Shimer S., and Cerami A. (1986). Identification of a common nucleotide sequence in the 3'-untranslated region of mRNA molecules specifying inflammatory mediators. *Proc Natl Acad Sci USA*, 83: 1670–1674.

Chen C. Y., and Shyu A. B. (1995). AU-rich elements: characterization and importance in mRNA degradation. *Trends Biochem Sci.*, 20: 465–470. Chomczynski P., and Sacchi N. (1987). Single step method of RNA isolation by acid guanidinium thiocyanate-phenol-chlorophorm extraction. *Anal. Biochem.*, 162: 156–159.

Darnell J. E. Jr., Kerr I. M., and Stark G. R. (1994). Jak-STAT pathways and transcriptional activation in response to IFNs and other extracellular signaling proteins. *Science*, 264: 1415–1421.

Dimri G. P., Lee X., Basile G., Acosta M., Scott G., Roskelley C., Medrano E. E., Linskens M., Rubelj I., Pereira-Smith O., Peacocke M., and Campisi, J. (1995). A biomarker that identifies senescent human cells in culture and in aging skin in vivo. *Proc. Natl. Acad. Sci. USA,* 92: 9363–9367.

Fisher P. B., and Grant S. (1985). Effects of interferon on differentiation in normal and tumor cells. Pharmacology and Therapeutics, 27: 143–166. Fisher P. B., Prignoli D. R., Hermo H. Jr., Weinstein I. B., and Pestka S. (1985). Effects of combined treatment with interferon and mezerein on melanogenesis and growth in human melanoma cells. *J. Interferon Res.,* 5: 11–22.

Gire V., and Wynford-Thomas D. (1998). Reinitiation of DNA synthesis and cell division in senescent human fibroblasts by microinjection of anti-p53 antibodies. *Mol. Cell. Biol.,* 18: 1611–1621.

Goeddel D. V., Leung D. W., Dull T. J., Gross M., Lawn R. M., McCandliss R., Seeburg P. H., Goldstein, S., (1990) Replicative Senescence The Human Fibroblast Comes Of Age. *Science* 249:1129–1133.

Gutterman J. U. (1994). Cytokine therapeutics: lessons from interferon alpha. *Proc. Natl. Acad. Sci. USA,* 91: 1198–1205.

Hayflick L., and Moorehead P. S. (1961). The serial cultivation of human diploid cell strains. *Exp. Cell Res.,* 25: 585–621.

Holt S. E., Wright W. E., and Shay J. W. (1996). Regulation of telomerase activity in immortal cell lines. *Mol. Cell. Biol.,* 16: 2932–2939.

Huang F., Adelman J., Jiang H., Goldstein N. I., and Fisher P. B. (1999). Identification and temporal expression pattern of genes modulated during irreversible growth arrest and terminal differentiation in human melanoma cells. *Oncogene,* in press.

Irving J., Feng J., Wistrom C., Pikaart M., and Villeponteau B. (1992). An altered repertoire of fos/jun (AP-1) at the onset of replicative senescence. *Exp Cell Res.,* 202: 161–166.

Jiang H., and Fisher P. B. (1993). Use of a sensitive and efficient subtraction hybridization protocol for the identification of genes differentially regulated during the induction of differentiation in human melanoma cells. *Mol. Cell. Different.,* 1: 285–299.

Jiang H., Lin J., and Fisher, P. B. (1994a). A molecular definition of terminal cell differentiation in human melanoma cells. *Mol. Cell. Different.,* 2: 221–239.

Jiang H., Lin J., Su Z. -z., Collart F. R., Huberman E., and Fisher P. B. (1994b). Induction of differentiation in human promyelocytic HL-60 leukemia cells activates p21, WAF1/CIP1, expression in the absence of p53. *Oncogene,* 9: 3397–3406.

Jiang H., Lin J. J., Su Z. -z., Goldstein N. I., and Fisher P. B. (1995a). Subtraction hybridization identifies a novel melanoma differentiation associated gene, mda-7, modulated during human melanoma differentiation, growth and progression. *Oncogene,* 11: 2477–2486.

Jiang H., Lin J., Su Z. -z., Kerbel R. S., Herlyn M., Weissman R. B., Welch D., and Fisher P. B. (1995b). The melanoma differentiation associated gene mda-6, which encodes the cyclin-dependent kinase inhibitor p21, is differentially expressed during growth, differentiation and progression in human melanoma cells. *Oncogene,* 10: 1855–1864.

Jiang H., Su Z. -z., Boyd J., and Fisher P. B. (1993a). Gene expression changes associated with reversible growth suppression and the induction of terminal differentiation in human melanoma cells. *Mol. Cell. Different.,* 1: 41–66.

Jiang H., Waxman S., and Fisher P. B. (1993b). Regulation of c-fos, c-jun and jun-B gene expression in human melanoma cells induced to terminally differentiate. *Mol. Cell. Different.,* 1: 197–214.

Kashima N., Nishi-Takaoka C., Fujita T., Taki S., Yamada G., Hamuro J., and Taniguchi T. (1985). Unique structure of murine interleukin-2 as deduced from cloned cDNAs. *Nature,* 313: 402–404.

Lacombe L., Orlow I., Silver D., Gerald W. L., Fair W. R., Reuter V. E., and Cordon-Cardo C. (1996). Analysis of p21WAF1/CIP1 in primary bladder tumors. *Oncol. Res.,* 8: 409–414.

Lee, W. M. (1988) Linc, Currant Activation Of The Transforming Potential Of The Human Fos Proto-Oncogene Requires Message Stabilization And Results In Increased Amounts Of Partially Modified Fos Protein. *Mol. Cell. Biol.* 8(12)5521–5527.

Lin J. J., Jiang H., and Fisher P. B. (1996). Characterization of a novel melanoma differentiation associated gene, mda-9, that is down-regulated during terminal cell differentiation. *Mol. Cell. Different.,* 4 (4): 317–333.

Lin J. J., Jiang H. and Fisher P. B. (1998). Melanoma differentiation associated gene-9 is a human gamma interferon responsive gene. *Gene,* 207: 105–110.

Linke S. P., Clarkin K. C., Di Leonardo A., Tsou A., and Wahl G. M. (1996). A reversible, p53-dependent $G_0/G_1$ cell cycle arrest induced by ribonucleotide depletion in the absence of detectable DNA damage. *Genes & Devel.,* 10(8): 934–947.

Murano S., Thweatt R., et al., (1991) Diverse Gene Sequences Are Overexpres. In Werner Syndrome Fibroblasts Undergoing Premature Replicative Senescence. *Mol. Cell. Biol.* 11(8):39005–39014.

Myer V. E., Fan X. C., and Steitz J. A. (1997). Identification of HuR as a protein implicated in AUUUA-mediated mRNA decay. *EMBO J.,* 16: 2130–2139.

Medrano E. E., Yang F., Boissy R., Farooqui J., Shah V., Matsumoto K., Nordlund J. J., and Park H. Y. (1994). Terminal differentiation and senescence in the human melanocyte: repression of tyrosine-phosphorylation of the extracellular signal-regulated kinase 2 selectively defines the two phenotypes. *Mol. Biol. Cell.,* 5: 497–509.

Nedwin G. E., Naylor S. L., Sakaguchi A. Y., Smith D., Jarrett-Nedwin J., Pennica D., Goeddel D. V., and Gray P. W. (1985). Human lymphotoxin and tumor necrosis factor genes: structure, homology and chromosomal localization. *Nucleic Acids Res.,* 13:6361–6373.

Niculescu A. B., Chen X., Smeets M., Hengst L., Prives C., and Reed S. I. (1998). Effects of p21(Cip1/Waf1) at both the $G_1/S$ and the $G_2/M$ cell cycle transitions: pRb is a critical determinant in blocking DNA replication and in preventing endoreduplication. *Mol. Cell. Biol.,* 18: 629–643.

Sambrook, J., et al. (1989) *Molecular Cloning: a laboratory manual. Second Edition.* Cold Spring Harbor Laboratory Press (1989).

Shaw G., and Kamen R. (1986). A conserved AU sequence from the 3' untranslated region of GM-CSF mRNA mediates selective mRNA degradation. *Cell,* 46: 659–667.

Smith J. R., and Pereira-Smith O. M. (1996) Replicative senescence:implications for in vivo aging and tumor suppression. *Science,* 273: 63–67.

Stark G. R., Kerr I. M, Williams B. R. G., Silverman R. H., and Schreiber, R. D. (1998). How cells respond to interferons. *Annu. Rev. Biochem.,* 67: 227–264

Steinman R. A., Hoffman B., Iro A., Guillouf C., Liebermann D. A., and el-Housein ME. (1994). Induction of p21 (WAF-1/CIP1) during differentiation. *Oncogene,* 9: 3389–3396.

Ullrich A., Yelverton E., and Gray P. W. (1981). The structure of eight distinct cloned human leukocyte interferon cDNAs. *Nature*, 290: 20–26.

Van Straaten F., Muller R., Curran T., Van Beveren C., and Verma I. M. (1983). Complete nucleotide sequence of a human c-onc gene: deduced amino acid sequence of the human c-fos protein. *Proc Natl Acad. Sci. USA*, 80: 3183–3187.

Wong G. G., Witek J. S., Temple P. A., Wilkens K. M., Leary A. C., Luxenberg D. P., Jones S. S., Brown E. L., Kay R. M., Orr E. C., Shemaker C., Golde D. W., Kaufman R. J., Hewick R. M., Wang E. A., and Clark S. C. (1985). Human GM-CSF: molecular cloning of the complementary DNA and purification of the natural and recombinant proteins. *Science*, 228: 810–815.

Wright W. E., Pereira-Smith O. M., and Shay, J. W. (1989). Reversible cellular senescence: implications for immortilization of normal human diploid fibroblasts. *Mol. Cell. Biol.*, 9: 3088–3092.

Zhang P., Vigne J. L., and Mellon S. H. (1998). Polyribonucleotide phosphorylase is a double-stranded DNA-binding protein. *DNA Cell Biol.*, 17: 169–175.

EXAMPLE #1

Background and Significance

During terminal differentiation and senescence many genes are differentially expressed. Two processes that control the overall mRNA levels are transcription and mRNA stability. Since both proliferation and differentiation are dynamic processes requiring continues regulation (Blau, H. M., 1992, Blau et al., 1992, Blau et al, 1985) a thorough knowledge of the molecular mechanisms that regulate gene expression will significantly contribute to our understanding of development, differentiation and malignancy. Gene expression is regulated by two mechanisms: transcriptional mechanisms which determine the rate of mRNA production and equally important but under-studied post-transcriptional mechanisms which determine the overall amount of protein being produced. The experimental data from *Xenopous laevis, Drosophila melanogaster, Caenorhabditis elegans* document the importance of post-transcriptional mechanisms in early patterning of the embryos which directs correct distribution, stability, and translation of inherited maternal transcripts (Seydoux, G., 1996) Additionally, in plants, it has been shown that it is the post-transcriptional regulation and not transcription that directs the differentiation of chloroplast from its protoplast precursor (Deng and Gruissem, 1987). In mammals, posttranscriptional regulation appears to be important in cells responding to environmental stress, proliferation and differentiation (June et al, 1990, Sierra et. al., 1994)

The sequences responsible for post-transcriptional regulation are found in the 3' untranslated regions (3'UTR) of the transcripts. When orthologous genes were compared, large regions were found to exhibit more than 70% conservation over 300–500 million years of evolution, from mammals, birds, amphibians, or fish (Spicher et al., 1998). Post-transcriptional regulation of mRNA levels is a pivotal control point in gene expression. Early response genes, such as cytokines, lymphokines and proto-oncogenes are regulated by a cis-acting adenylate-uridylate-rich element (ARE) found in the 3' untranslated region (UTR) of the mRNA (Caput et al., 1986; Shaw and Kamen, 1988; Chen and Shyu, 1995; Myer et al., 1997). Currently, three classes of destabilizing elements have been identified: AUUUA-lacking elements and AUUUA-containing elements grouped into those with scattered AUUUA motifs (such as proto-oncogenes) and those with overlapping AUUUA motifs (such as growth factors) (Chen et al., 1995; Myer et al., 1997). A replacement of 3'UTR containing ARE in place of a 3'UTR of a stable message, such as β-globin or luciferase targets this very stable mRNA for rapid degradation (Shaw and Kamen, 1988, Maddireddi et al., 2000). In contrast, the removal of an ARE stabilizes an otherwise labile message (Miller et al., 1984; Lee et al., 1988)

A pool of genes involved in mRNA stability remains very small. However, one of the best studied family of genes in this area is Elav. Elav, which stands for embryonic-lethal abnormal vision, was first identified in *Drosophila melanogaster*. Deletion mutants of the elav gene are embryonic lethal because of lack of neuronal differentiation (Robinow and White, 1991). In mammals and in *Xenopus,* the elav gene family consists of three members that are developmentally regulated and tissue specific (Hel-N1, HuC, HuD,) and one member that is ubiquitously expressed called HuR (Szabo et al, 1991, Good, 1995, Ma et al., 1996, Antic and Keene, 1997). The mechanism by which Elav genes promote the differentiation of neurons is not completely understood, however, it is known that Elav can bind AU rich elements in ther 3'UTRs of selected genes. By selectively stabilizing selected genes, the overall amount of gene expression changes observed during terminal differentiation of neurons is regulated.

To obtain further insights into 3' UTR stabilization, 3' end maturation has been studied in detail in plants and bacteria. It is worth noting that the protein complexes involved in this process in these two completely different organisms are highly conserved. They are composed of endonucleases, exonucleases, helicases and enolases. *E.coli*, which lives in an energy high environment, has two exonucleases involved in the processing of 3'UTRs: RNase II, which has hydrolytic activity and PNPase (polynucleotide phosphorylase) which has phosphorolytic activity (Higgins et al., 1993). Single mutant of either PNPase or RNase II is viable, whereas double mutants die (Donovan and Kushner, 1986). On the other hand, *B.Subtilis*, which lives in the soil-an energy poor environment-exclusively uses PNPase and lacks RNase II. There may be a few different explanations for the presence of two exonucleases in *E.coli*. Firstly, the two exonucleases may have different specificities. This is supported by the fact that a specific degradation of S20 mRNA accumulates in pnp mutants but it fails to accumulate in rnb (Rnase II) mutants (Mackie, 1989). Another explanation could be that PNPase is phosphorolytic and Rnase II is hydrolytic. As phosphorolysis releases nucleotide diphosphates (Gedefroy-Colburn and Grunberg-Manago, 1966), the energy of the phosphate bond is conserved. Differential use of these two enzymes may reflect an adaptation to changing energy conditions (Deutscher and Reuven, 1991). This model is supported by the fact that *B. subtilis*, which normally inhabits low energy environment, uses PNPase exclusively, while *E.coli* predominantly uses Rnase II. Another interesting point worth noting is that PNPase also functions during competence development of *B.subtilis*. Since compentence is a state during which specialization is acquired, competence has been used as a simple model for differentiation. Genetic competence may be defined as a physiological state enabling a bacterial culture to bind and take up high-molecular-weight exogenous DNA (transformation). The study of competence genes has permitted their classification into two broad categories. Late competence genes are expressed under competence control and specify products required for the binding, uptake, and processing of transforming DNA.

Regulatory genes specify products that are needed for the expression of the late genes (Dubnau, 1991). PNPase is necessary for the expression of late competence genes. Transformability of pnp mutant is 1–5% of that seen in wild type strains (Luttinger A, et al., 1996)

In plants, PNPase functions during chlororoplast differentiation where it is involved in processing of plastid 3' UTR (example:petD). It is interesting to note that plastid genes also possess AU rich regions in its 3' UTR. Identically to bacteria, plant PNPase has a 3'-5' processive exonuclease activity that exhibits increased specificity for poly(A) and poly(U). (Hayes et al., 1996) Human teratocarcinoma cells (NT2) can be differentiated into neurons with retinoic acid treatment and thus provides an excellent model to study neuronal differentiation. Recently it has been shown that a member of elav family, Hel-N1, when transfected into NT2 cells, forms neurites, an early sign of differentiation. However it does not cause terminal differentiation (Antic et al., 1999). Since Old-35 encodes PNPase, a 3'-5' exonuclease involved in degradation of mRNA sequences, it is possible that Old-35 can increase the effects of Hel-N1 in NT2 cells and cause them to differentiate.

Determining the Half-life of Old-35 mRNA in HO-1 Cells

Figure 11:
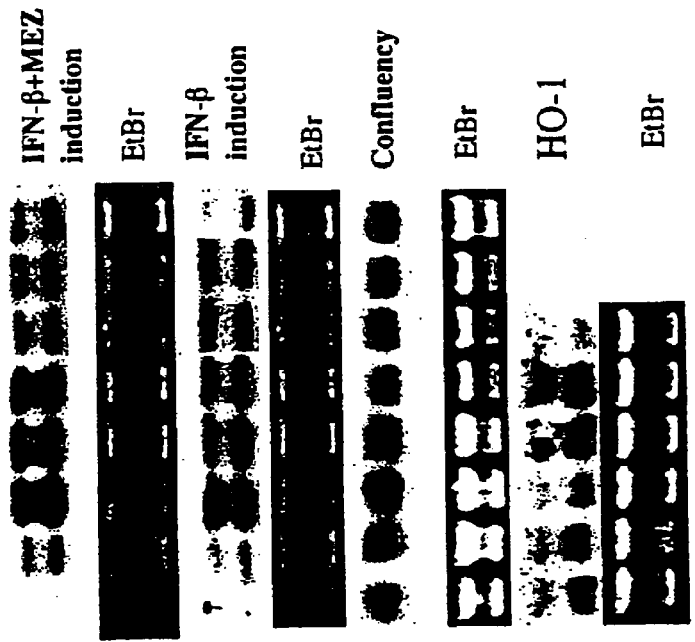
FIG. 11 Northern Blot of HO-1, confluent HO-1, IFN-β treated, IFN-β+MEZ treated HO-1 treated with Actinomycin D (50 mg/ml). Total RNAs were collected 2,4,6,8,10,12 after the AD treatment. Old-35 cDNA was used as a probe. Ethydium Bromide was shown for loading control FIG. 12 Northern Blot of IDH4 and AR5 cells. IDH4 cells contain dexamethasone (DEX) inducible mouse mammary tumor virus-driven simian virus 40 T-antigen. Total RNA was extracted from cells treated with DEX (indicated as +), and from cells growing without DEX for 3,5,7, and 14 days). AR5 cells contain temperature sensitive simian virus 40 T-antigen. Total RNA was collected from cells at 35C and 1,3,7,14 days after shift to 39 C. Old-35 and p21 were used as a probe.

Since Old-35 has an AU rich 3'UTR (FIG. 4) we have speculated that its expression may be regulated by post-transcriptional mechanisms. One way to study post-transcriptional processes is to investigate mRNA half-lives. In a mammalian cell culture system this can be achieved by treating cells with Actinomycin D (AD). Since AD inhibits RNA polymerase II activity, mRNA synthesis is terminated and the mRNA synthesized before AD treatment is allowed to decay. Total RNA is collected at different time points and quantified using Northern analyses. Using this protocol, we have examined the half-lives of Old-35 mRNA in HO-1, confluent HO-1, IFN-β treated, and IFN-β+MEZ treated HO-1. The half-life of Old-35 in all the treatments did not change and (FIG. 11) was estmated to be 6 hr. Since there was no difference in half-life between HO-1 and IFN-β treated HO-1 it is assumed that a post-transcriptional mechanism is not responsible for the upregulation of Old-35 mRNA level in IFN-β treated HO-1.

Expression of Old-35 During Growth Arrest and Senescence of IDH4 and AR5 Cells

Figure 12:
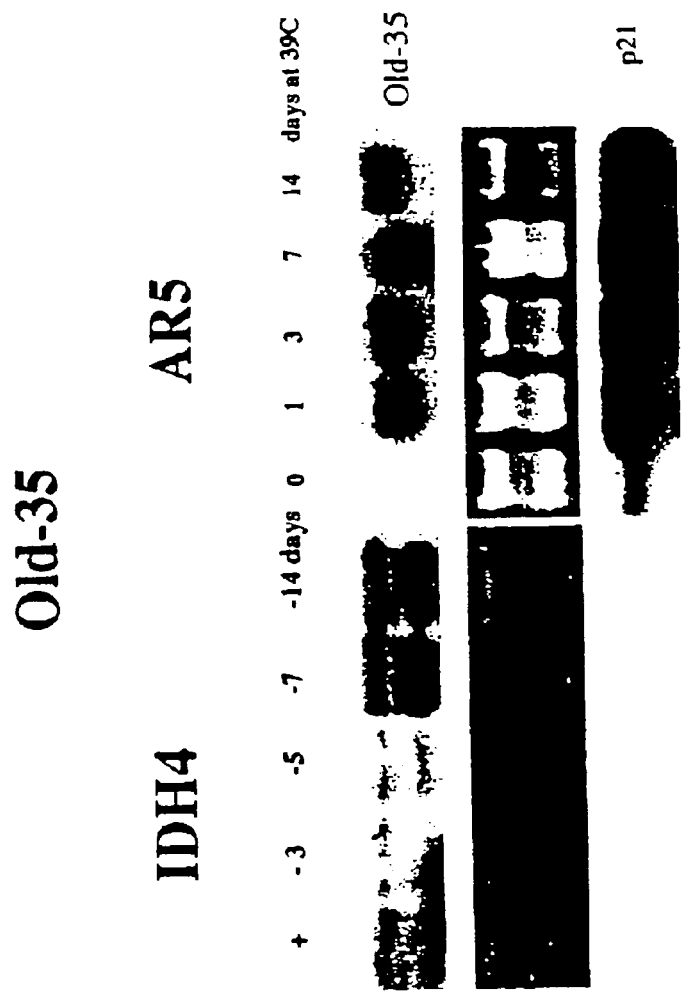

IDH4 cells were produced by transfecting IMR-90, normal human fibroblasts, with a dexamethasone (DEX) inducible mouse mammary tumor virus-driven simian virus 40 T-antigen (Wright et al., 1989). In this model system, prolonged proliferation and the absence of markers of senescence are dependent upon the continued presence of DEX and thus the SV40 T-antigen. (Wright et al., 1989). In DEX-free medium, DNA synthesis declines by ~80% within the first 3 days and reaches a minimum level at day 7. This decline corresponds with a decrease in telomerase activity and T-antigen expression (Holt et al., 1996). Since T-antigen has a long half-life (3 days) and remains in the cells for about 5–7 days after the removal of DEX, it is possible that the up-regulation of Old-35 by day 7 corresponds with the depletion of T-antigen in these cells (FIG. 12). However, there is one drawback associated with using IDH4 cells. Since the expression of T-antigen is dependent upon DEX, a shift of IDH4 cells towards senescence is dependent upon a complete depletion of DEX from the media and serum in which the cells are growing. This is normally achieved by charcoal stripping of the serum. However, since fetal serum contains vast amount of steroids, it becomes a challenge to do so in completion. Thus, the reproducibility of complete DEX depletion is a problem. To overcome this problem, we used another cell line, AR5. AR5 is very similar to IDH4, except the fact that T-antigen is not DEX inducible but it is rather temperature sensitive. AR5 cells are able to grow rapidly at 35° C. since they are expressing T-antigen. When shifted to 39° C., T-antigen is degraded and the cells become senescent. Total RNA was collected from AR5 cells grown at 35° C. and from AR5 cells shifted to 39° C. Old-35 was expressed one day after the shift and at the later time points as well (FIG. 12). To make sure that the cells had reached senescence when shifted to 35° C., we hybridized the Northern blot to the well characterized senescence marker, p21 (CDK inhibitor) (FIG. 12). p21 expression increased in AR5 cells shifted to 39° C. and showed a pattern similar to Old-35.

The difference between expression of Old-35 in IDH4 and AR5 cells can be accounted for by the differences in T-antigen depletion. Since T-antigen degrades much faster in AR5 cells (temperature sensitive) than in IDH4 cells (half-life 2–3 days), AR5 cells reach a senescent state at much faster rate than DEX depleted IDH4 cells.

Cloning of the Second Variant (3.8 kb)

Figure 13:
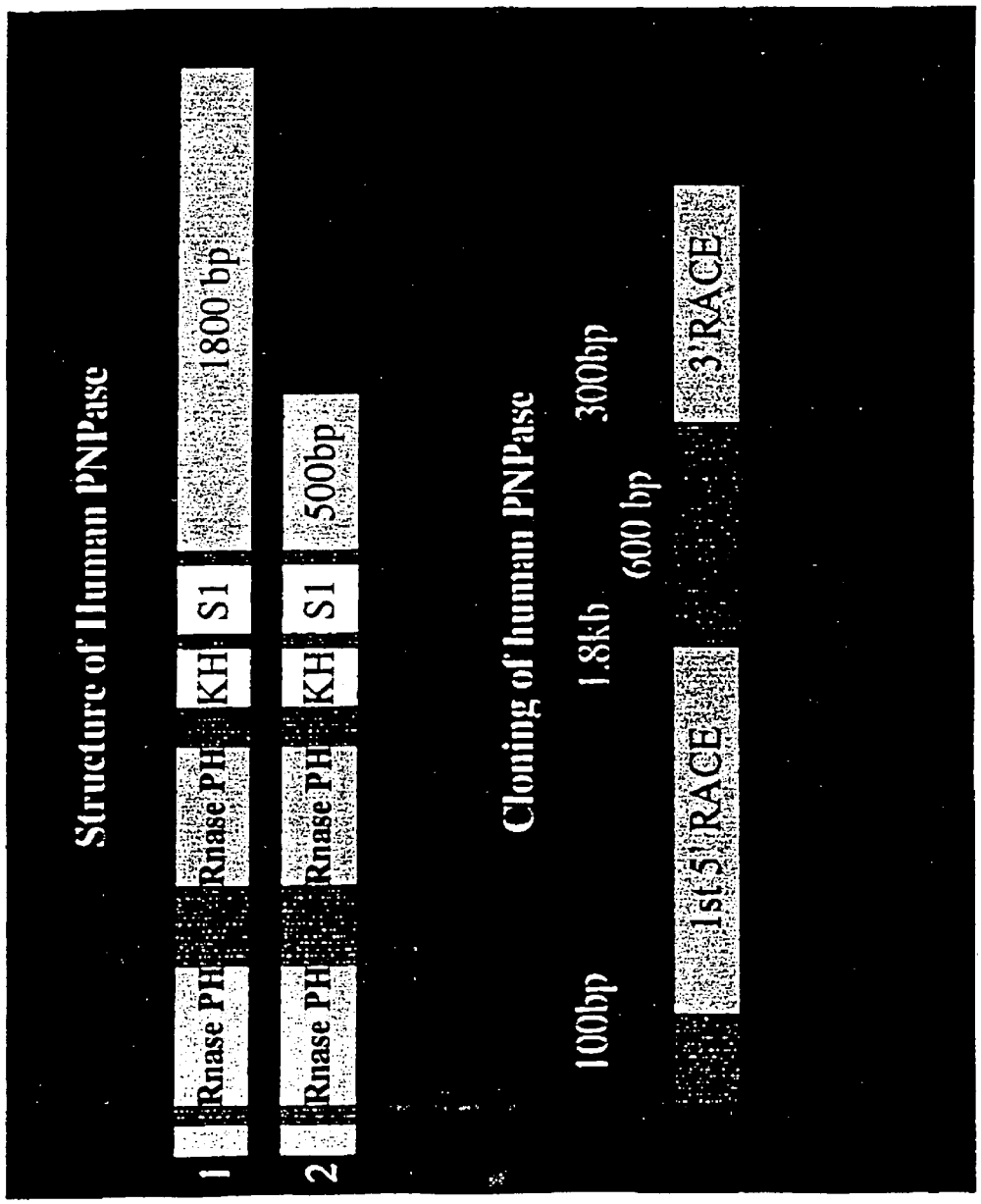
FIG. 13 Structure of Old-35 gene. RnasePH, KH, S1 signify domains found in Old-35 cDNA. Top picture shows two different versions of Old-35 which vary in the 3'UTR length The bottom picture shows cloning of the Old-35 cDNA using C-ORF technique.

Once most of the sequence was known, the cDNA was screened against the BLAST-EST database. In this search we have identified another version of Old-35 (3.8 kb) which is probably the upper band observed on Northern blots. The 3.8 kb EST was sequenced. The sequence analysis revealed differences in 3' UTRs of the 2.6 kb and 3.8 kb fragments. This may result from different polyadenylation patterns. To make sure that the upper band on the Old-35 Northern Blot represents the 3.8 kb fragment, we will use the 3' UTR of the ATCC clone as a probe (FIG. 13)

Old-35-GFP Localization

Since no antibody for Old-35 is currently available, we decided to test the localization of Old-35 by creating an N-terminal fusion of Old-35 and GFP (Clontech). Old-35 was cloned in frame with GFP without the first ATG and then transfected into HeLa and HO-1 cells with SuperFect reagent (Clontech). The protein was allowed to express for 24 hr. As expected for a degradative enzyme, Old-35 localized to the cytoplasm of Hela (FIG. 14) and HO-1 (data not shown).

Expression of Old-35 During Mouse Development

Figure 15:
FIG. 15 In situ hybridization to mouse embryo (9.5 days) using murine Old-35. The arrows indicate the expression in the spinal column.

Using Human Multiple Tissue Northern (MTN) Blots (Clontech) we determined that Old-35 was expressed in all of the tissues tested with the highest levels in the heart and brain. Since terminal differentiation of specific tissue cell types occurs during normal development of the embryo, the expression pattern of Old-35 was determined during mouse development. The highest level of Old-35 expression was apparent during the earliest stage of development (8 days) and it steadily declined with time (10 to 16 days). To determine spacial expression of Old-35, in situ hybridization expreriments were performed. Murine Old-35 was expressed in the spinal tube and in the arteries. However more expreriments have to performed to correctly determine the expression pattern (FIG. 15)

Effect of Different Interferon-α Subtypes on Old-35 Expression of Old-35

Figure 16:
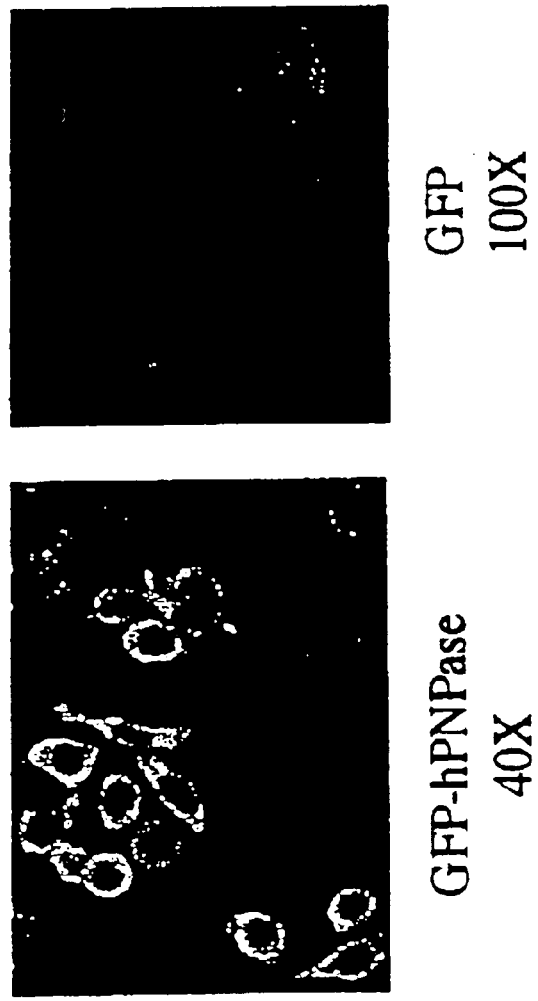
FIG. 16 Northern blot of Ho-1 cells treated with different subtypes of IFN-α using Old-35 as a probe. IFN-β was used as a control.

All subtypes of IFN-α stimulated Old-35 expression. IFN-α H and αI-stimulated Old-35 in the lowest extent. (FIG. 16). The above experiments document differential regulation of Old-35 expression by different cytokines, with type I interferons (IFN--α/IFN-β) being the most active cytokines tested in inducing Old-35 expression in H0-1 cells. Moreover, since IFN signaling cascades include Jak and Stat activation, they may prove to be important intermediates of Old-35 induction and expression.

Old-35 Genomic Structure

As described above, we have identified two BACs that were 100% homologous to specific regions of Old-35 cDNA. First BAC (RPCI-11, Plate=702, Col=8, Row=C) (Research Genetics) showed 100% homology to the 2207–2365 region of Old-35 cDNA. The sequenced regions flanking the Old-35 sequence were foreign thus it is highly possible that they are introns. The second BAC (CITBI-E1, clone 2505G20) (Research Genetics) showed 100% homology in 235 bp–313 bp region of Old-35 cDNA. After sequencing of the BACs, it became apparent that the Old-35 gene is distributed among 28 exons (Table 2). The spaces in the intron column signify no data for the intron size. The intron sizes are being determined.

Interestingly, there are at least three pseudogenes of Old-35 in the human genome. The first one is 92% homologous to the Old-35 cDNA and contains a portion of the cDNA (48 bp–1387 bp). 5' and 3' ends of the cDNA could not be found on this BAC. The second pseudogene is present on the $3^{rd}$ chromosome as determined by BLAST search at it contains a cDNA fragment from the $49^{th}$ nucleotide to the end of cDNA. This pseudogene exhibits 92% homology to the Old-35 cDNA. The third pseudogene also contains a cDNA fragment from 49 bp to 2517 bp. The second and third BACs are 90% homologous. In all cases, all of the BACs are highly mutated and intronless parts of the Old-35 cDNA.

TABLE 2

EXON-INTRON STRUCTURE OF OLD-35

| exons | exon size | introns | intron size |
|---|---|---|---|
| 1 | 174 | 1 | 6000 |
| 2 | 60 | 2 | 1100 |
| 3 | 74 | 3 | 1300 |
| 4 | 105 | 4 | 1100 |
| 5 | 49 | 5 | |
| 6 | 63 | 6 | |
| 7 | 47 | 7 | |
| 8 | 113 | 8 | 6600 |
| 9 | 186 | 9 | 800 |
| 10 | 51 | 10 | 600 |
| 11 | 57 | 11 | 3500 |
| 12 | 96 | 12 | 800 |
| 13 | 102 | 13 | |
| 14 | 70 | 14 | |
| 15 | 36 | 15 | |
| 16 | 66 | 16 | |
| 17 | 89 | 17 | |
| 18 | 53 | 18 | |
| 19 | 105 | 19 | |
| 20 | 72 | 20 | |
| 21 | 63 | 21 | |
| 22 | 83 | 22 | |
| 23 | 83 | 23 | |
| 24 | 106 | 24 | |
| 25 | 55 | 25 | |
| 26 | 77 | 26 | |
| 27 | 45 | 27 | |
| 28 | 406 | | |

What is claimed is:

1. An antibody or antigen-binding fragment thereof that specifically binds to a protein having an amino acid sequence as set forth in SEQ ID NO:42.

2. The antibody or antigen binding fragment thereof of claim 1 which is a monoclonal antibody.

* * * * *

SEQUENCE LISTING

<160> NUMBER OF SEQ ID NOS: 51

<210> SEQ ID NO 1
<211> LENGTH: 674
<212> TYPE: DNA
<213> ORGANISM: Homo sapiens
<220> FEATURE:
<221> NAME/KEY: unsure
<222> LOCATION: 534, 590
<223> OTHER INFORMATION: a or g or c or t

<400> SEQUENCE: 1

```
aattcggcac gagcacgtct tgaccttgaa cgcaaagtgg aatctttgca agaagagatt    60 gccttttga agaaactcca cgaagaggaa atccaggagc tgcaggctca gattcaggaa   120
cagcatgtcc aaatcgatgt ggatgtttcc aagcctgacc tcacggctgc cctgcgtgac   180
gtacgtcagc aatatgaaag tgtggctgcc aagaacctgc aggaggcaga agaatggtac   240
aaatccaagt ttgctgacct ctctgaggct gccaaccgga acaatgacgc cctgcgccag   300
gcaaagcagg agtccactga gtaccggaga caggtgcagt ccctcacctg tgaagtggat   360
gcccttaaag gaaccaatga gtccctgaaa cgccagatgc gtgaaatgga agagaacttt   420
gccgttgaag ctgctaacta ccaagacact attggcccgc tgcaggatg agattcagaa   480 tatgaaggag gaaatggctc gtcaccttcg tgaataccaa gacctgctca atgntaagat   540
```

```
ggcccttgac attgagattg ccacctacag gaagctgctg ggaaggcgan gagagcagga    600
tttctctgct cttccaaact tttcctcctt gaccttgagg gaaactaatc tggattcact    660
ccctcttggg tgaa                                                     674
```

<210> SEQ ID NO 2
<211> LENGTH: 678
<212> TYPE: DNA
<213> ORGANISM: Homo sapiens
<220> FEATURE:
<221> NAME/KEY: unsure
<222> LOCATION: 566, 669
<223> OTHER INFORMATION: a or g or c or t

<400> SEQUENCE: 2

```
aattcggcac gagcaggacc caaggaacca aaattgcatc tgatggtctc aagggtcgtg     60
tgtttgaagt gagtcttgct gatttgcaga atgatgaagt tgcattagaa aattcaagct    120
gattactgaa gatgttcagg gtaaaaactg cctgactaac ttccatggca tggatcttac    180
ccgtgacaaa atgtgttcca tggtcaaaaa atggcagaca atgattgaag ctcacgttga    240
tgtcaagact accgatggtt acttgcttcg tctgttctgt gttggttta ctaaaaaacg     300 caacaatcag atacggaaga cctcttatgc tcagcaccaa caggtccgcc aaatccggaa    360
gaagatgatg gaaatcatga cccgagaggt gcagacaaat gacttgaaag aagtggtcaa    420
taaattgatt ccagacagca ttggaaaaga catagaaaag gcttgccaat ctatttatcc    480
tctccatgat gtcttcgtta gaaaagtaaa atgctgaag aagcccaagt ttgaattggg     540
aaagctcatg gagcttcatg gtgaanggca gtagttctgg aaaaagccac ttggggacga    600
aacaggtgct aaaagtttga acgactgatg gatattgaac cccagtccaa gaatctggtt    660
aaaggtcana cttcaaat                                                 678
```

<210> SEQ ID NO 3
<211> LENGTH: 670
<212> TYPE: DNA
<213> ORGANISM: Homo sapiens
<220> FEATURE:
<221> NAME/KEY: unsure
<222> LOCATION: 656
<223> OTHER INFORMATION: a or g or c or t

<400> SEQUENCE: 3

```
aattcggcac gaggatgatg accttcaaga aaatgaagac aataaacaac ataagaaag     60 cttgaaaaga gtgacctttg cttaccaga tgatgcggaa actgaagata caggtgtttt    120
aaatgtaaag aaaaattctg atgaagttaa atcctccttt gaaaaagac aggaaaagat    180 gaatgaaaaa attgcatctt tagaaaaaga gttgttagaa aaaagccgt ggcaacttca    240 gggggaagtg acagcacaga agaggccaga gaacagcctc ctggaggaga ccctacactt    300
tgaccatgct gtccggatgg cacctgtgat tacagaggaa accacccttc aactggaaga    360
tatcattaaa cagaggataa gagatcaggc ttgggatgat gtagtacgta agaaaaaacc    420
taaagaggat gcatatgaat ataaaaagcg tttaaccta gaccatgaga gagtaaatt    480 gagccttgct gaaatttatg aacaggagta catcaaactc aaccagcaaa aacagcaga    540 agaagaaaat ccagaacatg tagaaattca gaagatgatg gattccctct tcttaaattg    600
gatgcctctc aaacttccct ttatcccta accgcctgtc cagagattaa agttgnggcc    660
aaatctgcca                                                         670
```

<210> SEQ ID NO 4
<211> LENGTH: 675
<212> TYPE: DNA
<213> ORGANISM: Homo sapiens
<220> FEATURE:
<221> NAME/KEY: unsure
<222> LOCATION: 530, 534, 650, 651, 655
<223> OTHER INFORMATION: a or g or c or t

<400> SEQUENCE: 4

```
aattcggcac gagatctgct gcaagcagcc aaatgttatg agaaggaact gggccgcctg      60
ctaagggatg ccccttcagg cataggcagt attttcctgt cagcatctga gcttgaggat     120
ggtagtgagg aaatgggcca gggcgcagtc agctccagtc ccagagagct cctctctaac     180
tcagagcaac tgaactgaga cagaggagga aaacagagca tcagaagcct gcagtggtgg     240
ttgtgacggg taggaggata ggaagacagg gggccccaac ctgggattgc tgagcaggga     300
agctttgcat gttgctctaa ggtacatttt taaagagttg ttttttggcc gggcgcagtg     360
gctcatgcct gtaatcccag cactttggga ggccgaggtg ggcggatcac gaggtctgga     420
gtttgagacc atcctggcta acacagtgaa atcccgtctc tactaaaaat acaaaaaatt     480
agccaggcgt ggtggctggc acctgtagtc ccagctactt gggagctgan gcangagaat     540
ggcgtgaacc tggaaggaag aagttgcagg tgagcccaag attgcgcccc cttgcactcc     600
agctgggcaa cagagcaaga cttcatctca aaaaaaaaa aaaaaaactn ncggnggggg      660
gcccccgggc cccca                                                      675
```

<210> SEQ ID NO 5
<211> LENGTH: 460
<212> TYPE: DNA
<213> ORGANISM: Homo sapiens
<220> FEATURE:
<221> NAME/KEY: unsure
<222> LOCATION: 411, 412, 415, 416, 423, 430, 433, 439, 442, 446, 452, 454, 456, 457
<223> OTHER INFORMATION: a or g or c or t

<400> SEQUENCE: 5

```
aattcggcac gagcacctct gtgtctacca tgacccccctt cctcacactg acctgtgttc     60
cttccctgtt ctcttttcta ttaaaaataa gaacctgggc agagtgcggc agctcatgcc    120
tgtaatccca gcacttaggg aggccgagga gggcagatca cgaggtcagg agatcgaaac    180
catcctggct aacacggtga acccccgtct ctactaaaaa atacaaaaaa ttagctgggc    240
gcagaggcac gggcctgtag tcccagctac tcaggaggcg gaggcaggag aatggcgtca    300
acccgggagg cggaggttgc agtgagccag gattgtgcga ctgcactcca gcctgggtga    360
cagggtgaaa cgccatctca aaaataaaa attaaaaaaa aaaaaaaaa nntcnnggggg    420
ggncccggtn ccnatttcnc cntatnggga gncntnncaa                          460
```

<210> SEQ ID NO 6
<211> LENGTH: 445
<212> TYPE: DNA
<213> ORGANISM: Homo sapiens

<400> SEQUENCE: 6

```
aattcggcac gagttctgcc catgctgcag acagtggcca agaacaagga ccagggcacc     60
tatgaggatt atgtcgaagg acttcgggtg tttgacaagg aaggaaatgg caccgtcatg    120
ggtgctgaaa tccggcatgt tcttgtcaca ctgggtgaga agatgacaga ggaagaagta    180
```

```
gagatgctgg tggcagggca tgaggacagc aatggttgta tcaactatga agagctcgtc    240
cgcatggtgc tgaatggctg aggaccttcc cagtctcccc agagtccgtg cctttccctg    300
tgtgaatttt gtatctagcc taaagtttcc ctaggctttc ttgtctcagc aactttccca    360
tcttgtctct cttggatgat gtttgccgtc agcattcacc aaataaactt gctctctggg    420
ccctcggaaa aaaaaaaaa aaaaa                                           445
```

<210> SEQ ID NO 7
<211> LENGTH: 666
<212> TYPE: DNA
<213> ORGANISM: Homo sapiens
<220> FEATURE:
<221> NAME/KEY: unsure
<222> LOCATION: 483, 498, 527
<223> OTHER INFORMATION: a or c or g or t

<400> SEQUENCE: 7

```
aattcggcac gaggcaatgt gcttggtttt aaagaaattc tccttgggaa aaaagtatcc     60
tcttttaatt ttacttccca taagcgtaaa tgcctggaca tagctcttgt gcaacccttta   120 aataaattgt tttgagtgtt ttttgagccc cagacaaata atgttttaaa gttatcccct   180
tgctacttta ctgatacctt tatcattcct gagacagttt gctaatttaa aaatgtagca   240
ttccatttgt atttatttct ctcccttgcc aaaaagattt tctaatactg cttgtaccag   300
ccagagaaag atccaaaaca ctactcagct ctcttgcact gaggaaattt ttcccccta    360 attgactcct ggcctacatc agccaaactt aaccttggtg gggtttggat ttgatagcca   420
attagttctg tgctggttgc aaagaattga tatttagatg gttttttaata ctcagcagat   480 tgncttcctt tatattgngt ctttttttatg ttgcatgttg cttttgntat cagcctgatt   540
ttttgctcag tatatgatag ttctgctgat ggtttggtta ttgggcagac atatcttcat   600
taagagtttt tggaaaactc atcaaattcg atgaatacat tttcttcata acccattgga   660
aatatc                                                              666
```

<210> SEQ ID NO 8
<211> LENGTH: 409
<212> TYPE: DNA
<213> ORGANISM: Homo sapiens

<400> SEQUENCE: 8

```
aattcggcac gagcgactac ggcggactaa tcttcaactc ctacatactt cccccattat     60
tcctagaacc aggcgacctg cgactccttg acgttgacaa tcgagtagta ctcccgattg   120
aagcccccat tcgtataata attacatcac aagacgtctt gcactcatga gctgtcccca   180
cattaggctt aaaaacagat gcaattcccg gacgtctaaa ccaaaccact ttcaccgcta   240
cacgaccggg ggtatactac ggtcaatgct ctgaaatctg tggagcaaac cacagtttca   300
tgcccatcgt cctagaatta attcccctaa aaatctttga aatagggccc gtatttaccc   360
tatagcaccc cctctacccc ctctagagca aaaaaaaaa aaaaaaaa                 409
```

<210> SEQ ID NO 9
<211> LENGTH: 667
<212> TYPE: DNA
<213> ORGANISM: Homo sapiens
<220> FEATURE:
<221> NAME/KEY: unsure
<222> LOCATION: 436, 663
<223> OTHER INFORMATION: a or c or g or t

<400> SEQUENCE: 9

```
aattcggcac gagacaaggc acaaatgatc caaatcaagg aggctacaaa agggcagcct    60
agagggcaga acagagaaaa gctagacaaa atgataagat cagccatatt tcattttgaa   120
tctgcagtgg aaaaaaagcc cacatttgag gtggctcatc tagacctggc aagaatgtat   180
atagaagcag gcaatcacag aaaagctgaa gagaattttc aaaaattgtt atgcatgaaa   240
ccagtggtag aagaaacaat gcaagacata catttccact atggtcggtt tcaggaattt   300
caaaagaaat ctgacgtcaa tgcaattatc cattatttaa agctataaa aatagaacag    360 gcatcattaa caaggataaa agtatcaat tctttgaaga aattggtttt aaggaaactt    420
cggagaaagg cattanactg gaaagcttga gcctccttgg gttcgtctac aaattggaag   480
gaaatatgaa tgaagccctg gagtactatg agcgggccct gagactggct gctgactttg   540
agactctgtg agacaaggtc cttagcccca gatatcagcc ctttccattt catttcattt   600
tatgctaaca tttactaatc atcttttctg cttactggtt tcagaacctt ataattccct   660 ggnatga                                                            667

<210> SEQ ID NO 10
<211> LENGTH: 672
<212> TYPE: DNA
<213> ORGANISM: Homo sapiens
<220> FEATURE:
<221> NAME/KEY: unsure
<222> LOCATION: 585
<223> OTHER INFORMATION: a or c or g or t

<400> SEQUENCE: 10
aattcttcct gtacgattgg ggatataacg ggcttcacta accttcccta ggcattgaaa    60 cttccccccaa atctgatgga cctagaagtc tgcttttgta cctgctgggc cccaaagttg   120
ggcatttttc tctctgttcc ctctcttttg aaaatgtaaa ataaaaccaa aaatagacaa   180 cttttttcttc agccattcca gcatagagaa caaaccttat ggaaacagga atgtcaattg   240
tgtaatcatt gttctaatta ggtaaataga agtccttatg tatgtgttac aagaatttcc   300
cccacaacat cctttatgac tgaagttcaa tgacagtttg tgtttggtgg taaaggattt   360
tctccatggc ctgaattaag accattagaa agcaccaggc cgtgggagca gtgaccatct   420
gctgactgtt cttgtggatc ttgtgtccag ggacatgggg tgacatgcct cgtatgtgtt   480
agagggtgga atggatgtgt ttggcgctgc atgggatctg gtgcccctct tctcctggat   540
tcacatcccc acccagggcc cggttttact aagtgtctgc cctanattgg gtcaaaggag   600
gtcatccaac tgactttatc aagtggaatt gggatatatt tgatatactt ctggctaaca   660
acatgggaaa ag                                                       672

<210> SEQ ID NO 11
<211> LENGTH: 672
<212> TYPE: DNA
<213> ORGANISM: Homo sapiens
<220> FEATURE:
<221> NAME/KEY: unsure
<222> LOCATION: 585
<223> OTHER INFORMATION: a or c or g or t

<400> SEQUENCE: 11
aattcttcct gtacgattgg ggatataacg ggcttcacta accttcccta ggcattgaaa    60 cttccccccaa atctgatgga cctagaagtc tgcttttgta cctgctgggc cccaaagttg   120
ggcatttttc tctctgttcc ctctcttttg aaaatgtaaa ataaaaccaa aaatagacaa   180
```

```
cttttttcttc agccattcca gcatagagaa caaaccttat ggaaacagga atgtcaattg       240
tgtaatcatt gttctaatta ggtaaataga agtcctatg tatgtgttac aagaatttcc        300
cccacaacat cctttatgac tgaagttcaa tgacagtttg tgtttggtgg taaaggattt       360
tctccatggc ctgaattaag accattagaa agcaccaggc cgtgggagca gtgaccatct       420
gctgactgtt cttgtggatc ttgtgtccag ggacatgggg tgacatgcct cgtatgtgtt      480
agagggtgga atggatgtgt ttggcgctgc atgggatctg gtgcccctct tctcctggat       540
tcacatcccc acccagggcc cggtttact aagtgtctgc ctanattgg gtcaaaggag        600 gtcatccaac tgactttatc aagtggaatt gggatatatt tgatatactt ctggctaaca       660
acatgggaaa ag                                                            672

<210> SEQ ID NO 12
<211> LENGTH: 669
<212> TYPE: DNA
<213> ORGANISM: Homo sapiens
<220> FEATURE:
<221> NAME/KEY: unsure
<222> LOCATION: 587, 595, 600, 660, 662
<223> OTHER INFORMATION: a or c or g or t

<400> SEQUENCE: 12
aattcctaga caccaaatac agtgtgggaa tacacaacct actagcctat gtgaaacacc        60
tgaaaggcca gaatgaggaa gccctgaaga gcttaaaaga agctgaaaac ttaatgcagg       120
aagaacatga caaccaagca aatgtgagga gtctggtgac ctggggcaac tttgcctgga      180
tgtattacca catgggcaga ctggcagaag cccagactta cctggacaag gtggagaaca       240
tttgcaagaa gctttcaaat cccttccgct atagaatgga gtgtccagaa atagactgtg       300
aggaaggatg ggccttgctg aagtgtggag gaaagaatta tgaacgggcc aaggcctgct       360
ttgaaaaggt gcttgaagtg gaccctgaaa accctgaatc cagcgctggg tatgcgatct       420
ctgcctatcg cctggatggc tttaaattag ccacaaaaaa tcacaagcca ttttctttgc       480
ttcccctaag gcaggctgtc cgcttaaatc cagataatgg atatattaag ggtctccttg       540
ccctgaagct tcaggatgaa ggacaggaaa cttgaaggag aaaagtncat tgaanaactn      600
tacccaccat gtcctccaga cctatgcttt gattgcagcc aagttttacc gaaaaaagn        660 tntgggata                                                               669

<210> SEQ ID NO 13
<211> LENGTH: 702
<212> TYPE: DNA
<213> ORGANISM: Homo sapiens
<220> FEATURE:
<221> NAME/KEY: unsure
<222> LOCATION: 530, 585, 600, 616, 654, 702
<223> OTHER INFORMATION: a or c or g or t

<400> SEQUENCE: 13
aattcggcac gagtgttata ggagatcaca atcaacatc tcacttccga accggggaag         60
aagacaagaa aattaatgaa gaactggagt ctcaatatca gcaaagtatg gacagtaaat      120
tatcaggaag atatcggcga cattgtggac ttggcttcag tgaggtagaa gaccatgatg       180
gagaaggtga tgtggctgga gatgatgatg atgacgatga tgattcacct gatcctgaaa       240
gtccagatga ttctgaaagc gattcagagt cagagaaaga agaatctgct gaagaactcc       300
aagctgctga gcaccctgat gaagtggagg atccccaaaa caaaaagat gcaaaaagca       360 attataaaat gatgtttgtt aaatccagtg gttcataact cccaaacgct tagtctttgt       420
```

```
attaaaagta agccttattg ttacaatgca cagtggagga ctgcttatag agcacagacc      480
tttgtattat aatttttaaa aaggcccttt taaataatta caaagagtgn ttgctttcaa      540
atgccatggg ttacactttt atgggcatga ctataccatt tttgnaaaga gtagagttgn      600
ataaaataag aaatanttcc agtactcact tccttctatt agcatctcac cctntaattc      660
ccttatgggg aaatgcttct tttggttggg atagcttttt an                         702
```

<210> SEQ ID NO 14
<211> LENGTH: 312
<212> TYPE: DNA
<213> ORGANISM: Homo sapiens

<400> SEQUENCE: 14

```
aattcggcac gaggtaaatg ttgagccttt ttggcctggc ttgtttgcaa aggccctggc       60
caacgtcaac attgggagcc tcatctgcaa tgtaggggcc ggtggacctg ctccagcagc      120
tggtgctgca ccagcaggag gtcctgcccc ctccactgct gctgctccag ctgaggagaa      180
gaaagtggaa gcaaagaaag aagaatccga ggagtctgat gatgacatgg gctttggtct      240
ttttgactaa acctctttta taacatgttc aataaaaagc tgaactttaa aaaaaaaaa      300 aaaaaaaaaa ac                                                          312
```

<210> SEQ ID NO 15
<211> LENGTH: 391
<212> TYPE: DNA
<213> ORGANISM: Homo sapiens

<400> SEQUENCE: 15

```
aattctgagg aggaactgat gatggcatgg aagaactttt cagtcatctg aaggaggttc       60
cgctggtttt cctcaaggct ctctgatggt tctaacctgg taggatccac ttcaaagcta      120
acatgttgcc aatcagagga tgtgatcaca attcgtaata aaggatccag gagttttgt       180 agataggtag caccatatac cttgaaacag aatgtcatta ttttactggc caagctgttg      240
cctcggaaga gagtctgcat ggagtctgcc aattctactt ctttagaaaa catgttccag      300
agcagttggt agagtaaatg ccgagaatca aacagagtaa ccagaactcg aggggggcc      360 cggtacccaa ttcgccctat agtgagtcgt t                                     391
```

<210> SEQ ID NO 16
<211> LENGTH: 720
<212> TYPE: DNA
<213> ORGANISM: Homo sapiens
<220> FEATURE:
<221> NAME/KEY: unsure
<222> LOCATION: 6, 7, 359, 383, 449, 456, 459,473, 501, 504, 515, 518,
      528, 532, 535, 538, 549, 562, 567, 568,577, 579, 601, 603
<223> OTHER INFORMATION: a or c or g or t
<220> FEATURE:
<221> NAME/KEY: unsure
<222> LOCATION: 614, 618, 621, 625, 633, 636, 641, 678, 683, 691, 708
<223> OTHER INFORMATION: a or c or g or t

<400> SEQUENCE: 16

```
aattcnnatc gagnttcttt gtatgtgaac ggtcctggaa ggattctgtt gctccttggc       60
aggtgtgtgg tttgcgctat agactggctc cggtgatctg gccattatac tctgctgtct      120
ccatcttgag gatgtagggg attatgctgt ctatcgaaac attgccaatg agaccagtaa      180
aaaaaagttc ttctgttatg ttggagctca tcagcctgag tgccggcagg cgaacgagga      240
tccgggccaa tctataaaag ggagtgtcat tagaaaagga gactgtttga tgcccttcaa      300
```

```
ccacagctca gcaaaggctc ctggggtccc gtctgtattg caccagaatc aaaccaacng    360
gatccacctt ccacccacct ttnttttctg atttcaacag ttcctcttat agaaatttat    420
catgagaaaa aaccaaatga gtccaaaang tatgtncana tgggttccct tcnctctggt    480
aatccaactt tcctaacccc nccnccaaaa aaaanctngg aattcttnac cnggnggnca    540
ccttaaggng gaagccttca tnggaannac ttgctanana ctcatttaaa aaaccgatta    600
ntnccaaccc tgtntttnct gncccnggaa aanacntccc ntgacatatg gctcaaataa    660 aaggtttttaa agggggaantt ttnaaaaaaa anaaaaaaaa aaaccctngg ggggggccc    720
```

<210> SEQ ID NO 17
<211> LENGTH: 205
<212> TYPE: DNA
<213> ORGANISM: Homo sapiens
<220> FEATURE:
<221> NAME/KEY: unsure
<222> LOCATION: 158, 159, 161, 163, 176, 182, 186, 189, 191, 193, 197,
      1699, 200, 202, 203
<223> OTHER INFORMATION: a or c or g or t

<400> SEQUENCE: 17

```
aattcgaaca gcatacccc gattccgcta cgaccaactc atacacctcc tatgaaaaaa      60
cttcctacca ctcaccctag cattacttat atgatatgtc tccatacccca ttacaatctc    120 cagcattccc cctcaaacct aaaaaaaaaa aaaaaaannt ngnggggggg cccggnccccc   180 anttcnccnt ntgggngnn gnntt                                             205
```

<210> SEQ ID NO 18
<211> LENGTH: 691
<212> TYPE: DNA
<213> ORGANISM: Homo sapiens
<220> FEATURE:
<221> NAME/KEY: unsure
<222> LOCATION: 479
<223> OTHER INFORMATION: a or c or g or t

<400> SEQUENCE: 18

```
aattcttaca tgttttcttt gctttaagtg taactggcag ttttccattg gtttacctgt     60
gaaatagttc aaagccaagt ttatatacaa ttatatcagt cctctttcaa aggtagccat    120
catggatctg gtaggggaa aatgtgtatt ttattacatc tttcacattg gctatttaaa    180
gacaaagaca aattctgttt cttgagaaga gaatattagc tttactgttt gttatggctt    240
aatgacacta gctaatatca atagaaggat gtacatttcc aaattcacaa gttgtgtttg    300
atatccaaag ctgaatacat tctgctttca tcttggtcac atacaattat ttttacagtt    360
ctcccaaggg agttaggcta ttcacaacca ctcattcaaa agttgaaatt aaccatagat    420
gtagataaac tcagaaattt aattcatgtt tcttaaatgg gctactttgt cctttttgnt    480
attagggtgg tatttagtct attagccaca aaattgggaa aggagtagaa aaagcagtaa    540
ctgacaactt gaataataca ccagagataa tatgagaatc agatcatttc aaaactcatt    600
tcctatgtaa ctgcattgag aactgcatat gtttcgctga tatatggggt tttccatttg    660
cgaatgggtc cattctctct ccggacttt t                                   691
```

<210> SEQ ID NO 19
<211> LENGTH: 483
<212> TYPE: DNA
<213> ORGANISM: Homo sapiens

<400> SEQUENCE: 19

-continued

```
tctagaacta gtggatcccc cgggctgcag gaattcggca cgaggtttta agtactctga      60
aattgatctg tgatcaataa tactaatatg ttatctttta ccgtattctg cctctcacta     120 ttgatttaa ttagttagga gtatttgagc tgttatttct tgagcttaat attttttag       180 agttaactct ttaaggagat aatcatggct gtagacaagg ccagggctgg ctgacgtgcc     240
ttagaaagtt tgaatgcaat aaagcggtgt tggcgttct cctgcattgt agtgcgggtt      300
acaaatgcta attgttccgt caactggtgt cagcagatga gccgcccact acagacggct     360
actgcccagg gacctgccca ggccccaccc aagggctccc aagggttgag atttctgcag     420
acctatagcc agcacactta gtcctgccct atatagagtt cctcttcggg aagcttttga    480
taa                                                                   483
```

<210> SEQ ID NO 20
<211> LENGTH: 589
<212> TYPE: DNA
<213> ORGANISM: Homo sapiens
<220> FEATURE:
<221> NAME/KEY: unsure
<222> LOCATION: 556, 558, 587
<223> OTHER INFORMATION: a or c or g or t

<400> SEQUENCE: 20

```
gcacgagtcg aaatgtacat tggtgattct gaagcttata tcggagcaga cattaaagac      60
aaattaaaat gttatgactt tgatgtgcat acaatgaaga cactaaaaaa cattatttca    120
cctccgtggg atttcaggga atttgaagta gaaaaacaga ctgcagaaga aacgggcttt    180
acgccattgg aaacctcaag gaaaactcca gattccagac cttccttgga agaaaccttt     240
gaaattgaaa tgaatgaaag tgacatgatg ttagagacat ctatgtcaga ccacagcacg    300
tgactccagt cagtggtcct ggtcccactg tcccagtgta ggttagtatt ccttcacatc     360
ctctccatgg cttaagaatg tcccacttcc taacgtgact ccaaactgca tctctacatt    420
taggaacaga gacccgcctt aagagactgg atcgcacacc tttgcaacag atgtgttctg    480
attctctgaa cctacaaaat agttatacat agtggaataa agaaggtaaa ccatcaaaaa    540
aaaaaaaaaa aaaccncngg gggggcccgg gcccaatttg cccttnagg                589
```

<210> SEQ ID NO 21
<211> LENGTH: 713
<212> TYPE: DNA
<213> ORGANISM: Homo sapiens
<220> FEATURE:
<221> NAME/KEY: unsure
<222> LOCATION: 389, 396, 400, 409, 418, 429, 463, 468, 520, 556, 575,
      591, 594, 613, 635, 641, 650, 666, 680, 682, 700, 704
<223> OTHER INFORMATION: a or c or g or t

<400> SEQUENCE: 21

```
aattcaagtg cctgattaat tgaggtggca acatagtttg agacgagggc agagaacagg      60
aagatacata gctagaagcg acgggtacaa aaagcaatgt gtacaagaag actttcagca    120
agtatacaga gagttcacct ctactctgcc ctcctcatag tcataatgta gcaagtaaag     180
aatgagaatg gattctgtac aatacactag aaaccaacat aatgtatttc tttaaaacct    240
gtgtgaaaaa ataaatgttc caccagtagg gatagggaa aagtaaccaa aagagagaaa     300
gagaaaggaa tgctggttta tctttgtaga ttgtaatcga atggagaaat ttgcagtatt    360
ttagccacta ttaggaattt tttttttng taaaangaan actgaactnt gttcaaangc     420
tttcatganc ctggtttgaa acggtaggaa agcaccaaaa cgngggancc tggggactaa    480
```

```
gggcctggtg caaggacttg ggaaatggca ttgataatan atgggggggt tttccccct    540
ttaaaaatgt tggatnttaa gggatataac ccttnttta ctccgaaaat nttntgagaa    600
atcccaaaat tcncggtatg cttggaacca ttganatttt ntagggaaan gccttgaata   660
gcctanacct caaagttggn gngaaccaaa attggagccn ttgncccacc tcc          713
```

```
<210> SEQ ID NO 22
<211> LENGTH: 480
<212> TYPE: DNA
<213> ORGANISM: Homo sapiens

<400> SEQUENCE: 22
```

```
cggcacgaga agaagtggta caggaggaat ttgtgatgat gagctgatct taatcaaaaa    60
tactaaggct cgtacgtctg catcgattat cttacgtggg gcaaatgatt tcatgtgtga   120
tgagatggag cgctctttac atgatgcact ttgtgtagtg aagagagttt tggagtcaaa   180
atctgtggtt cccggtgggg gtgctgtaga agcagcccct tccatatacc ttgaaaacta   240
tgcaaccagc atgggtctc gggaacagct tgcgattgca gagtttgcaa gatcacttct    300
tgttattccc aatacactag cagttaatgc tgcccaggac tccacagatc tggttgcaaa   360
attaagagct tttcataatg aggcccaggt taacccagaa cgtaaaaatc taaaatgatt   420
ggtcttgatt tgagcaatgg taaacctcga ggggggggccc ggtacccaat tcgccctata  480
```

```
<210> SEQ ID NO 23
<211> LENGTH: 198
<212> TYPE: DNA
<213> ORGANISM: Homo sapiens
<220> FEATURE:
<221> NAME/KEY: unsure
<222> LOCATION: 21
<223> OTHER INFORMATION: a or c or g or t

<400> SEQUENCE: 23
```

```
cctgttaaaa gctgttcttg ngtgttacat gtaacagaca tggtaaatat ttgtttacag    60
tctttgttta acaaaccatg catttaagtt taagtgaagt caacaaaaag gaaataggtg   120
tatggatatg tgattttgag attaaagtta gtcttaaaat gtaaaaaaaa aaaaaaaaa    180
aaaaaaaaaa aaaaaaaa                                                  198
```

```
<210> SEQ ID NO 24
<211> LENGTH: 414
<212> TYPE: DNA
<213> ORGANISM: Homo sapiens
<220> FEATURE:
<221> NAME/KEY: unsure
<222> LOCATION: 368, 370, 372, 374, 375, 376, 377 383, 386, 389
<223> OTHER INFORMATION: a or c or g or t

<400> SEQUENCE: 24
```

```
aattcggcac gagaaaagca gtataactgc ctgacacagc gggattgaac gagagaagaa    60
attgttcgtt attgctcaga aaattcaaac acgcaaagat cttatggata aaactcagaa   120
agtgaaggtg aagaaagaaa cggtgaactc cccagctatt tataaatttc agagtcgtcg   180
aaaacgttga cgtgttatag ataagccttg tcattctgta tcaaaatct gttgtcgttt    240
tctagtaact tcaaattcca ttactccaaa tggcatggtt ttccggtttg taaccataac   300
taaattgtca gtctgacatt taatgtcttt ctatggacaa cattaaatct ccctcccttc   360
tgtagaanan anannnnaaa aanccncccg ggggggggccg ggtccccatt cccc         414
```

<210> SEQ ID NO 25
<211> LENGTH: 367
<212> TYPE: DNA
<213> ORGANISM: Homo sapiens

<400> SEQUENCE: 25

```
aattcggcac gagaaaagca gtataactgc ctgacacagc gggattgaac gagagaagaa      60
attgttcgtt attgctcaga aaattcaaac acgcaaagat cttatggata aaactcagaa     120
agtgaaggtg aagaaagaaa cggtgaactc cccagctatt tataaatttc agagtcgtcg     180
aaaacgttga cgtgttatag ataagccttg tcattctgta tcaaaaatct gttgtcgttt     240
tctagtaact tcaaattcca ttactccaaa tggcatggtt ttccggtttg taaccataac     300
taaattgtca gtctgacatt taatgtcttt ctatgggaca acattaaatc tccctcccctt    360
ctgtaaa                                                              367
```

<210> SEQ ID NO 26
<211> LENGTH: 432
<212> TYPE: DNA
<213> ORGANISM: Homo sapiens
<220> FEATURE:
<221> NAME/KEY: unsure
<222> LOCATION: 386, 389, 390, 397, 404, 409, 413, 416, 424, 426, 430
<223> OTHER INFORMATION: a or c or g or t

<400> SEQUENCE: 26

```
aattcggcac gaggcagact tgaaacagtt ctgtctgcag aatgctcaac atgaccctct      60
gctgactgga gtatcttcaa gtacaaatcc cttcagaccc cagaaagtct gttcctttt     120
gtagtaaaat gaatctttca aaggtttccc aaaccactcc ttatgatcca gtgaatattc    180
aagagagcta catttgaagc ctgtacaaaa gcttatccct gtaacacatg tgccataata    240
tacaaacttc tactttcgtc agtccttaac atctacctct ctgaatttc atgaatttct    300
atttcacaag ggtaattgtt ttatatacac tggcagcagc atacaataaa acttagtatg    360
aaactttaaa aaaaaaaaaa aaaacntcnn ggggggnccc ggancccant tcnccntata    420
gggngnccgn tt                                                        432
```

<210> SEQ ID NO 27
<211> LENGTH: 398
<212> TYPE: DNA
<213> ORGANISM: Homo sapiens
<220> FEATURE:
<221> NAME/KEY: unsure
<222> LOCATION: 288, 298, 345, 348, 352, 357, 358, 368
<223> OTHER INFORMATION: a or c or g or t

<400> SEQUENCE: 27

```
aattcggcac gagtacaaaa ccagttggtg gtgacaagaa cggcggtacc cgggtggtta     60
aacttcgcaa aatgcctaga tattatccta ctgaagatgt gcctcgaaag ctgttgagcc    120
acggcaaaaa acccttcagt cagcacgtga gaaaactgcg agccagcatt accccggga     180
ccattctgat catcctcact ggacgccaca ggggcaagag ggtggttttc ctgaagcagc    240
tggctagtgg cttattactt gtgactggac ctctggtcct caatcgantt cctctacnaa    300
gaacacacca gaaatttgtc attgccactt caaccaaaat cgatntcngc antgtannaa    360
atcccaanac atcttactga tgcttacttc aagatgaa                            398
```

<210> SEQ ID NO 28
<211> LENGTH: 232

```
<212> TYPE: DNA
<213> ORGANISM: Homo sapiens

<400> SEQUENCE: 28
aattcggcac gagattgtat cggtttata ttacctgttc tgcttcacca ggagatcatg      60
ctgctgtgat actgagtttt ctaaacagca taaggaagac ttgctcccct gtcctatgaa    120
agagaatagt tttggagggg agaagtggga caaaaaagat gcagttttcc tttgtattgg    180
gaaatgtgaa aataaaattg tcaactcttt caaaaaaaaa aaaaaaaaa aa              232

<210> SEQ ID NO 29
<211> LENGTH: 539
<212> TYPE: DNA
<213> ORGANISM: Homo sapiens
<220> FEATURE:
<221> NAME/KEY: unsure
<222> LOCATION: 495, 508, 511, 526, 529
<223> OTHER INFORMATION: a or c or g or t

<400> SEQUENCE: 29
aattcggcac gagcacaacc agaaagtaag gtgttctact tgaaaatgaa aggagattat      60
tttaggtatc tttctgaagt ggcatctgga gacaacaaac aaaccactgt gtcgaactcc    120
cagcaggctt accaggaagc atttgaaatt agtaagaaag aaatgcagcc tacacaccca    180
attcgtcttg gtctggcact aaatttctca gtcttttact atgagattct aaactctcct    240
gaaaaggcct gtagcctggc aaaaacggca tttgatgaag caattgctga attggatacg    300
ctgaatgaag agtcttataa agacagcact ctgatcatgc agttacttag ggacaattca    360
ctctgtggac atcggaaaac cagggagacg aaggagacgc tggggaggga gagaactaat    420
gtttctcgtg ctttgtgatc tgttcagtgt cactctgtac cctcaacata tatcccttgt    480
gcgataaaaa aaanaaaaa aaaaaccntc nggggggggcc ccggancccn attccccct    539

<210> SEQ ID NO 30
<211> LENGTH: 568
<212> TYPE: DNA
<213> ORGANISM: Homo sapiens
<220> FEATURE:
<221> NAME/KEY: unsure
<222> LOCATION: 274, 278, 283, 291, 308, 314, 324, 326, 327, 331, 341,
      355, 371, 419, 461, 531, 534, 545, 558
<223> OTHER INFORMATION: a or c or g or t

<400> SEQUENCE: 30
attccaaacc aagtagtgtc tgtcagccct cttaactctg tgcacgccct atttcagtct      60
tttacatttg ttcttctagg gaatgtatgc atctctatat atattttccc tctcaaaacc    120
agaacatcaa cagtgctgtt tctgacactt cagacatccc acgcaaagcc acattgaatt    180
tttgccaaat gaaaacaca tccacaatca agttctaaga gggtgtcaag tgggaatat     240
taatattgtt tattattcaa aaatttagtt tatnaaangg aancaaaacc nttgaacctt    300
ttttcccnaa aaanaaggaa aatntnntgt ngaccaaggg ncgaacctga atccnccttg    360
aaaaattgtt ntctcagaaa ggaaaagcgc cctccagttc ttttaccccca agaatttana    420
aaaatttggt ccaagatttt atatgttcag ttgtttatgt ntaaaaataa ctttctggat    480
tttgtgggg aggaccggaa aaggaaggga gtttattcct atgttataca ntanaaactt    540
ccccnataaa atgccatnga tgggttga                                        568

<210> SEQ ID NO 31
<211> LENGTH: 315
```

<212> TYPE: DNA
<213> ORGANISM: Homo sapiens

<400> SEQUENCE: 31

```
aattcggcac gagcagggag ccgctagtga aaatctggca tgaaataagg actaatggcc    60
ccaaaaaagg aggtggctct aagtaaaact gggattggac agtagtggtg catctggtcc   120
ttgccgcctg agagcccag gagacatcgg ctagagtgac catggctatg ctcccgtctg   180
gaagatgcca gcatctggcc tcccactgtt ttcagctgtg tccccagtc cgtgtctttt   240
tagaatgtga atgatgataa agttgtgaaa taaggtttc tatctagttt gtaaaaaaaa   300
aaaaaaaaaa aaaaa                                                    315
```

<210> SEQ ID NO 32
<211> LENGTH: 458
<212> TYPE: DNA
<213> ORGANISM: Homo sapiens
<220> FEATURE:
<221> NAME/KEY: unsure
<222> LOCATION: 342, 355, 365, 368, 375, 381, 385, 414, 445
<223> OTHER INFORMATION: a or c or g or t

<400> SEQUENCE: 32

```
aattcaagga actttacatt gtaagagaaa acaaaacact gcaaaagaag tgtgccgact    60
atcaaataaa tggtgaaatc atctgcaaat gtggccaggc ttggggaaca atgatggtgc   120
acaaaggctt agatttgcct tgtctcaaaa taaggaattt tgtagtggtt ttcaaaaata   180
attcaacaaa gaaacaatac aaaaagtggg tagaattacc tatcacatt cccaatcttg   240
actattcaga atgctgttta tttagtgatg aggattagca cttgattgaa gattctttta   300
aaatactatc agttaaacat ttaatatgat tatgattaat gnattcatta tgctncagac   360
tgacntanga atcantaaaa ngatngtttt actctgcaaa aaaaaaaaaa aacncggggg   420
ggggcccggc cccaatttcc ccttntgggg gggggtttt                          458
```

<210> SEQ ID NO 33
<211> LENGTH: 470
<212> TYPE: DNA
<213> ORGANISM: Homo sapiens
<220> FEATURE:
<221> NAME/KEY: unsure
<222> LOCATION: 434, 459, 460
<223> OTHER INFORMATION: a or c or g or t

<400> SEQUENCE: 33

```
aattcttatc ttccagaggc tacaattatt ataatggaca atacttttac ctttgtctct    60
aaagatcaga ttagttttat ttgttcactt acgtgctttg attatcccct ctgaattata   120
gaccgagtct tgttgtttag cctaagagaa gatttatgta gtaatttctt ctcaggtatg   180
gaaccacggt cataactaac atgttggcca gaatagaacc actggttaaa catattttat   240
tcaccattaa gtgatcttta tcaatattct ggattagaca acaaattacc tttctgggtg   300
tttcttgtaa actatactcc tgtttgaatg ttaaactttg ttgctaaagt ttaattttaa   360
gatgtttgaa tgttcagttt atgtatttga actacaataa accaacccctt tttatataaa   420
aaaaaaaaaa aacntcgagg gggggcccgg ccccaattnn ccctataggg               470
```

<210> SEQ ID NO 34
<211> LENGTH: 261
<212> TYPE: DNA
<213> ORGANISM: Homo sapiens

```
<400> SEQUENCE: 34
aattcgaact gtgtgtatgt cagtggaatc aaatcaaaag ccactaacat ggctgtctgt      60
ttcactggac tgtcccattt gctggttaaa aggattgggg cccaaatcct ctggcctagc    120
atttctcagt gtttgctatt cagactgtct aaatacagca tgtgacaagc tgaagaagcc    180
aaatctagca gtcatttctg atttcattat attctccccc tcttcctgct aaaaagacaa    240
aaaacaaaaa aaaaaaaaaa a                                              261

<210> SEQ ID NO 35
<211> LENGTH: 309
<212> TYPE: DNA
<213> ORGANISM: Homo sapiens

<400> SEQUENCE: 35
aattcggcac gagctggaca ccaacagtga tggtcagcta gatttctcag aatttcttaa     60
tctgattggt ggcctagcta tggcttgcca tgactccttc ctcaaggctg tcccttccca    120
gaagcggacc tgaggacccc ttggccctgg ccttcaaacc caccccctt ccttccagcc     180 tttctgtcat catctccaca gcccacccat cccctgagca cactaaccac ctcatgcagg    240
ccccacctgc caatagtaat aaagcaatgt cacttttta aaacatgaaa aaaaaaaaa     300 aaaaaaaaa                                                            309

<210> SEQ ID NO 36
<211> LENGTH: 243
<212> TYPE: DNA
<213> ORGANISM: Homo sapiens
<220> FEATURE:
<221> NAME/KEY: unsure
<222> LOCATION: 8
<223> OTHER INFORMATION: a or c or g or t

<400> SEQUENCE: 36
aattcggntc gagctcgaat aagtttgact tgtgttttat cttaaccacc agatcattcc     60
ttctgtagct caggagagca cccctccacc ccatttgctc gcagtatcct agaatctttg    120
tgctctcgct gcagttccct tgggttcca tgttttcctt gttccctccc atgcctagct     180
ggattgcaga gttaagttta tgattatgaa ataaaaacta ataacaaaa aaaaaaaaa     240 aaa                                                                  243

<210> SEQ ID NO 37
<211> LENGTH: 650
<212> TYPE: DNA
<213> ORGANISM: Homo sapiens
<220> FEATURE:
<221> NAME/KEY: unsure
<222> LOCATION: 546, 553, 573
<223> OTHER INFORMATION: a or c or g or t

<400> SEQUENCE: 37
aattcggcac gagtaccatt cagcctgaat ttgctagtgt aggctctaaa tcaagtgtag     60
ttccgtgtga acttgcctgc agaacccagt gtgctttgaa gcaatgttgt gggacactac    120
cacaagcccc ttctggaaag gatgcagaaa agaccccagc agttagcatt tcttgtttag    180
aacttagtaa caatctagag aagaagccca ggaggactaa agctgaaaac atccctgctg    240
ttgtgataga gattaaaaac atgccaaaca acaacctga atcatctttg tgagtcttga     300 aaagatgtg atatttgact tttgctttaa actgcaagag gaaaagact ccactgaaat     360 tctaagtttg ccaagtagtg taattgaagt ccttgtctgg tcacacagtt taattctatt    420
```

-continued

```
tttgtaagaa cataatggga ctgcataaca gagttctata ttacaatttt gtgattatta      480
gtacagagta cagctatgct gtgactgttt tggaaagcca gttttaacac tatgttacat      540
ttttgnttaa agnaagttaa accttatata acntaatgac atttgatttc tggattttcc      600
catgataaaa aattaggggg gataaataaa aatggttact ggaatttcaa                 650
```

<210> SEQ ID NO 38
<211> LENGTH: 687
<212> TYPE: DNA
<213> ORGANISM: Homo sapiens
<220> FEATURE:
<221> NAME/KEY: unsure
<222> LOCATION: 444, 448, 451, 460, 461, 462, 468, 471, 476, 490, 506,
      510, 514, 522, 524, 535, 550, 563, 567, 568, 573, 579, 587, 590
<223> OTHER INFORMATION: a or c or g or t
<220> FEATURE:
<221> NAME/KEY: unsure
<222> LOCATION: 592, 593, 596, 608, 615
<223> OTHER INFORMATION: a or c or g or t

<400> SEQUENCE: 38

```
gaattcggca cgagattttt ttatttttca ttttcccctt aggcatattt agtatttttc      60
cctcaggcag atcattctga gtgtgcgagt gtgtgtgcac atgttacaaa ggcaactacc     120
atgttaataa aatattcaat ttgaaatcct tttcggtatt tgaattgctt ttgaataatg     180
ttttttatct ggatgtaaca ttgttgcatt agcttttaa ctttcccaag taattgaata      240 catttttatta cttggacttt tataaactct ttccctaccc actataaatg agacattcac    300
agcgttcaag tttgtattaa aggaaaggat tagtttgacc ccttctttg atggttaatg      360 catacatgca gttaaatccc tttatgcaaa tgtgacactg ctttactagg tcttttagtt     420
atttatttat tttttttttt ttgnccantt nattttttan nntaattnct naaacncatt     480 atttttttn aaaataaaaa aacacnatcn tttntttttta ananttaaac cttantaaat     540 ttttccccn aaaaaaaatc cntaannttt ttnaattttnt tgaattnaan annaantaaa     600 ccttttttnaa aaccnggcaa aaaaaaaaaa aaaaaaaaa aaaaaaaaaa aaaaaaaaa      660 aaaaaaaaaa aaaaaaaaa aaaaaaa                                          687
```

<210> SEQ ID NO 39
<211> LENGTH: 2549
<212> TYPE: DNA
<213> ORGANISM: Homo sapiens

<400> SEQUENCE: 39

```
gatggtcctt tccttctgcc acggcgggat cgggcactca cccagttgca agtgcgagca      60
ctatggagta gcgcagggtc tcgagctgtg gccgtggact taggcaacag gaaattagaa     120
atatcttctg gaaagctggc cagatttgca gatggctctg ctgtagtaca gtcaggtgac     180
actgcagtaa tggtcacagc ggtcagtaaa acaaaacctt cccctttccca gtttatgcct    240 ttggtggttg actacagaca aaaagctgct gcagcaggta gaattcccac aaactatctg     300
agaagagagg ttggtacttc tgataaagaa attctaacaa gtcgaataat agatcgttca     360
attagaccgc tctttccagc tggctacttc tatgatacac aggttctgtg taatctgtta     420
gcagtagatg tgtaaatga gcctgatgtc ctagcaatta atggcgcttc cgtagccctc      480
tcattatcag atattccttg gaatggacct gttggggcag tacgaatagg aataattgat     540
ggagaatatg ttgttaaccc aacaagaaaa gaaatgtctt ctagtacttt aaatttagtg     600
gttgctggag cacctaaaag tcagattgtc atgttggaag cctctgcaga gaacatttta     660
```

-continued

```
cagcaggact tttgccatgc tatcaaagtg ggagtgaaat atacccaaca aataattcag      720
ggcattcagc agttggtaaa agaaactggt gttaccaaga ggacacctca gaagttattt      780
accccttcgc cagagattgt gaaatatact cataaacttg ctatggagag actctatgca      840
gtttttacag attacgagca tgacaaagtt tccagagatg aagctgttaa caaaataaga      900
ttagatacgg aggaacaact aaaagaaaaa tttccagaag ccgatccata tgaaataata      960
gaatccttca atgttgttgc aaaggaagtt tttagaagta ttgttttgaa tgaatacaaa     1020
aggtgcgatg gtcgggattt gacttcactt aggaatgtaa gttgtgaggt agatatgttt     1080 aaaaccttc atggatcagc attatttcaa agaggacaaa cacaggtgct tgtaccgtt       1140 acatttgatt cattagaatc tggtattaag tcagatcaag ttataacagc tataaatggg     1200
ataaaagata aaaatttcat gctgcactac gagtttcctc cttatgcaac taatgaaatt     1260
ggcaaagtca ctggttttaaa tagaagagaa cttgggcatg gtgctcttgc tgagaaagct    1320
ttgtatcctg ttattcccag agattttcct ttcaccataa gagttacatc tgaagtccta     1380
gagtcaaatg ggtcatcttc tatggcatct gcatgtggcg gaagtttagc attaatggat    1440
tcaggggttc caatttcatc tgctgttgca ggcgtagcaa taggattggt caccaaaacc    1500
gatcctgaga agggtgaaat agaagattat cgtttgctga cagatatttt gggaattgaa    1560
gattacaatg gtgacatgga cttcaaaata gctggcacta taaaggaat aactgcatta      1620 caggctgata ttaaattacc tggaatacca ataaaaattg tgatggaggc tattcaacaa    1680
gcttcagtgg caaaaaagga gatattacag atcatgaaca aaactatttc aaaacctcga    1740
gcatctagaa aagaaatgg acctgttgta gaaactgttc aggttccatt atcaaaacga     1800
gcaaaatttg ttggacctgg tggctataac ttaaaaaaac ttcaggctga aacaggtgta    1860
actattagtc aggtggatga agaaacgttt tctgtatttg caccaacacc cagtgttatg    1920
catgaggcaa gagacttcat tactgaaatc tgcaaggatg atcaggagca gcaattagaa    1980
tttggagcag tataccgc cacaataact gaaatcagag atactggtgt aatggtaaaa      2040
ttatatccaa atatgactgc ggtactgctt cataacacac aacttgataa cgaaagatta    2100
aacatcctac tgccctagga ttagaagttg gccaagaaat tcaggtgaaa tactttggac    2160
gtgacccagc cgatggaaga atgaggcttt ctcgaaaagt gcttcagtcg ccagctacaa    2220
ccgtggtcag aactttgaat gacagaagta gtattgtaat gggagaacct atttcacagt    2280
catcatctaa ttctcagtga tttttttttt taaagagaa ttctagaatt ctattttgtc     2340
tagggtgatg tgctgtagag caacatttta gtagatcttc cattgtgtag atttctatat   2400
aatataaata catttaaatt atttgtacta aaatgctcat ttacatgtgc cattttttta    2460
attcgagtaa cccatatttg tttaattgta tttacattat aaatcaagaa atatttatta    2520
ttaaaagtaa gtcatttata catcttaga                                       2549
```

<210> SEQ ID NO 40
<211> LENGTH: 650
<212> TYPE: DNA
<213> ORGANISM: Homo sapiens

<400> SEQUENCE: 40

```
ttgaagatta caatggtgac atggacttca aaatagctgg cactaataaa ggaataactg       60
cattacaggc tgatattaaa ttacctggaa taccaataaa aattgtgatg gaggctattc     120
aacaagcttc agtggcaaaa aaggagatat tacagatcat gaacaaaact atttcaaaac    180
```

-continued

```
ctcgagcatc tagaaaagaa aatggacctg ttgtagaaac tgttcaggtt ccattatcaa      240
aacgagcaaa atttgttgga cctggtggct ataacttaaa aaaacttcag ctgaaacag       300 gtgtaactat tagtcaggtg gatgaagaaa cgtttctgt atttgcacca acacccagtg       360
ttatgcatga ggcaagaaga cttcattact gaatctgcaa ggatgatcag gagcagcaat     420
tagaatttgg agcagtatat accgccacaa taactgaaat cagagatact ggtgtaatgg     480
taaaattata tccaaatatg actgcggtac tgcttcataa cacacaactt gataacgaaa     540
gattaaacat cctactgccc taggattaga agttggccaa gaaattcagg tgaaatactt     600
tggacgtgac ccagccgatg gaagaatgag gctttctcga aaagtgcttc                650
```

<210> SEQ ID NO 41
<211> LENGTH: 640
<212> TYPE: DNA
<213> ORGANISM: Mus musculus

<400> SEQUENCE: 41

```
aatggtgaca tggatttcaa aatagccggt acaaataaag gaataactgc attacaggct      60
gatattaagt tacctggagt accaattaaa attataatgg aagccatcca acaagcgtca     120
gtggcaaaga aggagatact gcagataatg aacaaaacga tttcaaaacc tcgagcatca     180
agaaaagaaa atggaccagt gtagaaaaca gtaaaggttc cattatcaaa acgagcaaaa     240
ttcgttgggc ctggtggata tcacttaaaa aaactccagg ctgagacagg tgtaacaatt     300
agtcaggttg atgaagaaac cttctccata tttgcaccaa cacctactgc aatgcatgaa     360
gcaagagatt tcattacaga aatttgcaga gatgatcaag agcaacaatt agaatttgga     420 gcagttttata ccgcgacaat aactgaaatc agagacactg gagtgatggt aaaactgtat    480
ccaaacatga ctgcagtgct gcttcataat tcacaacttg accaacgaaa gattaaacat     540
cccactgccc taggactaga ggttggccaa gaaattcagg tcaaatactt tggccgtgat     600
ccagctgatg gaagaatgag gctttctcgt aaagtacttc                           640
```

<210> SEQ ID NO 42
<211> LENGTH: 705
<212> TYPE: PRT
<213> ORGANISM: Homo sapiens

<400> SEQUENCE: 42

```
Asp Gly Pro Phe Leu Leu Pro Arg Arg Asp Arg Ala Leu Thr Gln Leu
1               5                   10                  15

Gln Val Arg Ala Leu Trp Ser Ser Ala Gly Ser Arg Ala Val Ala Val
                20                  25                  30

Asp Leu Gly Asn Arg Lys Leu Glu Ile Ser Ser Gly Lys Leu Ala Arg
            35                  40                  45

Phe Ala Asp Gly Ser Ala Val Val Gln Ser Gly Asp Thr Ala Val Met
        50                  55                  60

Val Thr Ala Val Ser Lys Thr Lys Pro Ser Pro Ser Gln Phe Met Pro
65                  70                  75                  80

Leu Val Val Asp Tyr Arg Gln Lys Ala Ala Ala Gly Arg Ile Pro
                85                  90                  95

Thr Asn Tyr Leu Arg Arg Glu Val Gly Thr Ser Asp Lys Glu Ile Leu
                100                 105                 110

Thr Ser Arg Ile Ile Asp Arg Ser Ile Arg Pro Leu Phe Pro Ala Gly
            115                 120                 125

Tyr Phe Tyr Asp Thr Gln Val Leu Cys Asn Leu Leu Ala Val Asp Gly
```

-continued

```
            130                 135                 140
Val Asn Glu Pro Asp Val Leu Ala Ile Asn Gly Ala Ser Val Ala Leu
145                 150                 155                 160

Ser Leu Ser Asp Ile Pro Trp Asn Gly Pro Val Gly Ala Val Arg Ile
                165                 170                 175

Gly Ile Ile Asp Gly Glu Tyr Val Val Asn Pro Thr Arg Lys Glu Met
                180                 185                 190

Ser Ser Ser Thr Leu Asn Leu Val Ala Gly Ala Pro Lys Ser Gln
                195                 200                 205

Ile Val Met Leu Glu Ala Ser Ala Glu Asn Ile Leu Gln Gln Asp Phe
210                 215                 220

Cys His Ala Ile Lys Val Gly Val Lys Tyr Thr Gln Gln Ile Ile Gln
225                 230                 235                 240

Gly Ile Gln Gln Leu Val Lys Glu Thr Gly Val Thr Lys Arg Thr Pro
                245                 250                 255

Gln Lys Leu Phe Thr Pro Ser Pro Glu Ile Val Lys Tyr Thr His Lys
                260                 265                 270

Leu Ala Met Glu Arg Leu Tyr Ala Val Phe Thr Asp Tyr Glu His Asp
                275                 280                 285

Lys Val Ser Arg Asp Glu Ala Val Asn Lys Ile Arg Leu Asp Thr Glu
290                 295                 300

Glu Gln Leu Lys Glu Lys Phe Pro Glu Ala Asp Pro Tyr Glu Ile Ile
305                 310                 315                 320

Glu Ser Phe Asn Val Val Ala Lys Glu Val Phe Arg Ser Ile Val Leu
                325                 330                 335

Asn Glu Tyr Lys Arg Cys Asp Gly Arg Asp Leu Thr Ser Leu Arg Asn
                340                 345                 350

Val Ser Cys Glu Val Asp Met Phe Lys Thr Leu His Gly Ser Ala Leu
                355                 360                 365

Phe Gln Arg Gly Gln Thr Gln Val Leu Cys Thr Val Thr Phe Asp Ser
                370                 375                 380

Leu Glu Ser Gly Ile Lys Ser Asp Gln Val Ile Thr Ala Ile Asn Gly
385                 390                 395                 400

Ile Lys Asp Lys Asn Phe Met Leu His Tyr Glu Phe Pro Pro Tyr Ala
                405                 410                 415

Thr Asn Glu Ile Gly Lys Val Thr Gly Leu Asn Arg Arg Glu Leu Gly
                420                 425                 430

His Gly Ala Leu Ala Glu Lys Ala Leu Tyr Pro Val Ile Pro Arg Asp
                435                 440                 445

Phe Pro Phe Thr Ile Arg Val Thr Ser Glu Val Leu Glu Ser Asn Gly
450                 455                 460

Ser Ser Ser Met Ala Ser Ala Cys Gly Gly Ser Leu Ala Leu Met Asp
465                 470                 475                 480

Ser Gly Val Pro Ile Ser Ser Ala Val Ala Gly Val Ala Ile Gly Leu
                485                 490                 495

Val Thr Lys Thr Asp Pro Glu Lys Gly Glu Ile Glu Asp Tyr Arg Leu
                500                 505                 510

Leu Thr Asp Ile Leu Gly Ile Glu Asp Tyr Asn Gly Asp Met Asp Phe
                515                 520                 525

Lys Ile Ala Gly Thr Asn Lys Gly Ile Thr Ala Leu Gln Ala Asp Ile
                530                 535                 540

Lys Leu Pro Gly Ile Pro Ile Lys Ile Val Met Glu Ala Ile Gln Gln
545                 550                 555                 560
```

-continued

Ala Ser Val Ala Lys Lys Glu Ile Leu Gln Ile Met Asn Lys Thr Ile
            565                 570                 575

Ser Lys Pro Arg Ala Ser Arg Lys Glu Asn Gly Pro Val Val Glu Thr
            580                 585                 590

Val Gln Val Pro Leu Ser Lys Arg Ala Lys Phe Val Gly Pro Gly Gly
            595                 600                 605

Tyr Asn Leu Lys Lys Leu Gln Ala Glu Thr Gly Val Thr Ile Ser Gln
            610                 615                 620

Val Asp Glu Glu Thr Phe Ser Val Phe Ala Pro Thr Pro Ser Val Met
625                 630                 635                 640

His Glu Ala Arg Asp Phe Ile Thr Glu Ile Cys Lys Asp Asp Gln Glu
            645                 650                 655

Gln Gln Leu Glu Phe Gly Ala Val Tyr Thr Ala Thr Ile Thr Glu Ile
            660                 665                 670

Arg Asp Thr Gly Val Met Val Lys Leu Tyr Pro Asn Met Thr Ala Val
            675                 680                 685

Leu Leu His Asn Thr Gln Leu Asp Asn Glu Arg Leu Asn Ile Leu Leu
            690                 695                 700

Pro
705

<210> SEQ ID NO 43
<211> LENGTH: 705
<212> TYPE: PRT
<213> ORGANISM: Bacillus subtilis

<400> SEQUENCE: 43

Met Gly Gln Glu Lys His Val Phe Thr Ile Asp Trp Ala Gly Arg Thr
1               5                   10                  15

Leu Thr Val Glu Thr Gly Gln Leu Ala Lys Gln Ala Asn Gly Ala Val
            20                  25                  30

Met Ile Arg Tyr Gly Asp Thr Ala Val Leu Ser Thr Ala Thr Ala Ser
        35                  40                  45

Lys Glu Pro Lys Pro Leu Asp Phe Phe Pro Leu Thr Val Asn Tyr Glu
50                  55                  60

Glu Arg Leu Tyr Ala Val Gly Lys Ile Pro Gly Gly Phe Ile Lys Arg
65                  70                  75                  80

Glu Gly Arg Pro Ser Glu Lys Ala Val Leu Ala Ser Arg Leu Ile Asp
            85                  90                  95

Arg Pro Ile Arg Pro Leu Phe Ala Asp Gly Phe Arg Asn Glu Val Gln
            100                 105                 110

Val Ile Ser Ile Val Met Ser Val Asp Gln Asn Cys Ser Ser Glu Met
        115                 120                 125

Ala Ala Met Phe Gly Ser Ser Leu Ala Leu Ser Val Ser Asp Ile Pro
    130                 135                 140

Phe Glu Gly Pro Ile Ala Gly Val Thr Val Gly Arg Ile Asp Asp Gln
145                 150                 155                 160

Phe Ile Ile Asn Pro Thr Val Asp Gln Leu Glu Lys Ser Asp Ile Asn
                165                 170                 175

Leu Val Val Ala Gly Thr Lys Asp Ala Ile Asn Met Val Glu Ala Gly
            180                 185                 190

Ala Asp Glu Val Pro Glu Glu Ile Met Leu Glu Ala Ile Met Phe Gly
        195                 200                 205

His Glu Glu Ile Lys Arg Leu Ile Ala Phe Gln Glu Glu Ile Val Ala

-continued

```
                210                 215                 220
Ala Val Gly Lys Glu Lys Ser Glu Ile Lys Leu Phe Glu Ile Asp Glu
225                 230                 235                 240

Glu Leu Asn Glu Lys Val Lys Ala Leu Ala Glu Glu Asp Leu Leu Lys
                245                 250                 255

Ala Ile Gln Val His Glu Lys His Ala Arg Glu Asp Ala Ile Asn Glu
                260                 265                 270

Val Lys Asn Ala Val Ala Lys Phe Glu Asp Glu Glu His Asp Glu
                275                 280                 285

Asp Thr Ile Lys Gln Val Lys Gln Ile Leu Ser Lys Leu Val Lys Asn
290                 295                 300

Glu Val Arg Arg Leu Ile Thr Glu Glu Lys Val Arg Pro Asp Gly Arg
305                 310                 315                 320

Gly Val Asp Gln Ile Arg Pro Leu Ser Ser Glu Val Gly Leu Leu Pro
                325                 330                 335

Arg Thr His Gly Ser Gly Leu Phe Thr Arg Gly Gln Thr Gln Ala Leu
                340                 345                 350

Ser Val Cys Thr Leu Gly Ala Leu Gly Asp Val Gln Ile Leu Asp Gly
                355                 360                 365

Leu Gly Val Glu Glu Ser Lys Arg Phe Met His His Tyr Asn Phe Pro
370                 375                 380

Gln Phe Ser Val Gly Glu Thr Gly Pro Met Arg Gly Pro Gly Arg Arg
385                 390                 395                 400

Glu Ile Gly His Gly Ala Leu Gly Glu Arg Ala Leu Glu Pro Val Ile
                405                 410                 415

Pro Ser Glu Lys Asp Phe Pro Tyr Thr Val Arg Leu Val Ser Glu Val
                420                 425                 430

Leu Glu Ser Asn Gly Ser Thr Ser Gln Ala Ser Ile Cys Ala Ser Thr
                435                 440                 445

Leu Ala Met Met Asp Ala Gly Val Pro Ile Lys Ala Pro Val Ala Gly
                450                 455                 460

Ile Ala Met Gly Leu Val Lys Ser Gly Glu His Tyr Thr Val Leu Thr
465                 470                 475                 480

Asp Ile Gln Gly Met Glu Asp Ala Leu Gly Asp Met Asp Phe Lys Val
                485                 490                 495

Ala Gly Thr Glu Lys Gly Val Thr Ala Leu Gln Met Asp Ile Lys Ile
                500                 505                 510

Glu Gly Leu Ser Arg Glu Ile Leu Glu Glu Ala Leu Gln Gln Ala Lys
                515                 520                 525

Lys Gly Arg Met Glu Ile Leu Asn Ser Met Leu Ala Thr Leu Ser Glu
530                 535                 540

Ser Arg Lys Glu Leu Ser Arg Tyr Ala Pro Lys Ile Leu Thr Met Thr
545                 550                 555                 560

Ile Asn Pro Asp Lys Ile Arg Asp Val Ile Gly Pro Ser Gly Lys Gln
                565                 570                 575

Ile Asn Lys Ile Ile Glu Glu Thr Gly Val Lys Ile Asp Ile Glu Gln
                580                 585                 590

Asp Gly Thr Ile Phe Ile Ser Ser Thr Asp Glu Ser Gly Asn Gln Lys
                595                 600                 605

Ala Lys Lys Ile Ile Glu Asp Leu Val Arg Glu Val Glu Val Gly Gln
                610                 615                 620

Leu Tyr Leu Gly Lys Val Lys Arg Ile Glu Lys Phe Gly Ala Phe Val
625                 630                 635                 640
```

```
Glu Ile Phe Ser Gly Lys Asp Gly Leu Val His Ile Ser Glu Leu Ala
                645                 650                 655

Leu Glu Arg Val Gly Lys Val Glu Asp Val Val Lys Ile Gly Asp Glu
            660                 665                 670

Ile Leu Val Lys Val Thr Glu Ile Asp Lys Gln Gly Arg Val Asn Leu
        675                 680                 685

Ser Arg Lys Ala Val Leu Arg Glu Glu Lys Glu Lys Glu Glu Gln Gln
    690                 695                 700

Ser
705

<210> SEQ ID NO 44
<211> LENGTH: 705
<212> TYPE: PRT
<213> ORGANISM: Homo sapiens

<400> SEQUENCE: 44

Asp Gly Pro Phe Leu Leu Pro Arg Arg Asp Arg Ala Leu Thr Gln Leu
1               5                   10                  15

Gln Val Arg Ala Leu Trp Ser Ser Ala Gly Ser Arg Ala Val Ala Val
            20                  25                  30

Asp Leu Gly Asn Arg Lys Leu Glu Ile Ser Ser Gly Lys Leu Ala Arg
        35                  40                  45

Phe Ala Asp Gly Ser Ala Val Val Gln Ser Gly Asp Thr Ala Val Met
    50                  55                  60

Val Thr Ala Val Ser Lys Thr Lys Pro Ser Pro Ser Gln Phe Met Pro
65                  70                  75                  80

Leu Val Val Asp Tyr Arg Gln Lys Ala Ala Ala Gly Arg Ile Pro
            85                  90                  95

Thr Asn Tyr Leu Arg Arg Glu Val Gly Thr Ser Asp Lys Glu Ile Leu
            100                 105                 110

Thr Ser Arg Ile Ile Asp Arg Ser Ile Arg Pro Leu Phe Pro Ala Gly
        115                 120                 125

Tyr Phe Tyr Asp Thr Gln Val Leu Cys Asn Leu Leu Ala Val Asp Gly
    130                 135                 140

Val Asn Glu Pro Asp Val Leu Ala Ile Asn Gly Ala Ser Val Ala Leu
145                 150                 155                 160

Ser Leu Ser Asp Ile Pro Trp Asn Gly Pro Val Gly Ala Val Arg Ile
            165                 170                 175

Gly Ile Ile Asp Gly Glu Tyr Val Val Asn Pro Thr Arg Lys Glu Met
            180                 185                 190

Ser Ser Ser Thr Leu Asn Leu Val Val Ala Gly Ala Pro Lys Ser Gln
        195                 200                 205

Ile Val Met Leu Glu Ala Ser Ala Glu Asn Ile Leu Gln Gln Asp Phe
    210                 215                 220

Cys His Ala Ile Lys Val Gly Val Lys Tyr Thr Gln Gln Ile Ile Gln
225                 230                 235                 240

Gly Ile Gln Gln Leu Val Lys Glu Thr Gly Val Thr Lys Arg Thr Pro
            245                 250                 255

Gln Lys Leu Phe Thr Pro Ser Pro Glu Ile Val Lys Tyr Thr His Lys
        260                 265                 270

Leu Ala Met Glu Arg Leu Tyr Ala Val Phe Thr Asp Tyr Glu His Asp
    275                 280                 285

Lys Val Ser Arg Asp Glu Ala Val Asn Lys Ile Arg Leu Asp Thr Glu
```

```
                290                 295                 300
Glu Gln Leu Lys Glu Lys Phe Pro Glu Ala Asp Pro Tyr Glu Ile Ile
305                 310                 315                 320

Glu Ser Phe Asn Val Val Ala Lys Glu Val Phe Arg Ser Ile Val Leu
                325                 330                 335

Asn Glu Tyr Lys Arg Cys Asp Gly Arg Asp Leu Thr Ser Leu Arg Asn
                340                 345                 350

Val Ser Cys Glu Val Asp Met Phe Lys Thr Leu His Gly Ser Ala Leu
                355                 360                 365

Phe Gln Arg Gly Gln Thr Gln Val Leu Cys Thr Val Thr Phe Asp Ser
370                 375                 380

Leu Glu Ser Gly Ile Lys Ser Asp Gln Val Ile Thr Ala Ile Asn Gly
385                 390                 395                 400

Ile Lys Asp Lys Asn Phe Met Leu His Tyr Glu Phe Pro Pro Tyr Ala
                405                 410                 415

Thr Asn Glu Ile Gly Lys Val Thr Gly Leu Asn Arg Arg Glu Leu Gly
                420                 425                 430

His Gly Ala Leu Ala Glu Lys Ala Leu Tyr Pro Val Ile Pro Arg Asp
                435                 440                 445

Phe Pro Phe Thr Ile Arg Val Thr Ser Glu Val Leu Glu Ser Asn Gly
                450                 455                 460

Ser Ser Ser Met Ala Ser Ala Cys Gly Gly Ser Leu Ala Leu Met Asp
465                 470                 475                 480

Ser Gly Val Pro Ile Ser Ser Ala Val Ala Gly Val Ala Ile Gly Leu
                485                 490                 495

Val Thr Lys Thr Asp Pro Glu Lys Gly Glu Ile Glu Asp Tyr Arg Leu
                500                 505                 510

Leu Thr Asp Ile Leu Gly Ile Glu Asp Tyr Asn Gly Asp Met Asp Phe
                515                 520                 525

Lys Ile Ala Gly Thr Asn Lys Gly Ile Thr Ala Leu Gln Ala Asp Ile
                530                 535                 540

Lys Leu Pro Gly Ile Pro Ile Lys Ile Val Met Glu Ala Ile Gln Gln
545                 550                 555                 560

Ala Ser Val Ala Lys Lys Glu Ile Leu Gln Ile Met Asn Lys Thr Ile
                565                 570                 575

Ser Lys Pro Arg Ala Ser Arg Lys Glu Asn Gly Pro Val Val Glu Thr
                580                 585                 590

Val Gln Val Pro Leu Ser Lys Arg Ala Lys Phe Val Gly Pro Gly Gly
                595                 600                 605

Tyr Asn Leu Lys Lys Leu Gln Ala Glu Thr Gly Val Thr Ile Ser Gln
                610                 615                 620

Val Asp Glu Glu Thr Phe Ser Val Phe Ala Pro Thr Pro Ser Val Met
625                 630                 635                 640

His Glu Ala Arg Asp Phe Ile Thr Glu Ile Cys Lys Asp Asp Gln Glu
                645                 650                 655

Gln Gln Leu Glu Phe Gly Ala Val Tyr Thr Ala Thr Ile Thr Glu Ile
                660                 665                 670

Arg Asp Thr Gly Val Met Val Lys Leu Tyr Pro Asn Met Thr Ala Val
                675                 680                 685

Leu Leu His Asn Thr Gln Leu Asp Asn Glu Arg Leu Asn Ile Leu Leu
                690                 695                 700

Pro
705
```

```
<210> SEQ ID NO 45
<211> LENGTH: 245
<212> TYPE: PRT
<213> ORGANISM: Artificial Sequence
<220> FEATURE:
<223> OTHER INFORMATION: Consensus sequence between Homo sapiens OLD-35
      and Bacillus subtilis PNPase

<400> SEQUENCE: 45

Asp Arg Leu Gly Leu Ala Ala Gly Gly Asp Thr Ala Val Thr Ala Pro
 1               5                  10                  15

Pro Phe Pro Leu Val Tyr Ala Gly Ile Pro Arg Glu Ser Lys Leu Ser
                20                  25                  30

Arg Ile Asp Arg Ile Arg Pro Leu Phe Gly Gln Val Val Asp Ala Gly
            35                  40                  45

Ser Ala Leu Ser Ser Asp Ile Gly Pro Val Gly Ile Asp Asn Pro Thr
 50                  55                  60

Ser Asn Leu Val Val Ala Gly Lys Ile Met Glu Ala Ala Ile Gly
 65                  70                  75                  80

Ile Val Gly Lys Lys Leu Phe Glu Leu Ala Glu Leu Glu Lys Glu Val
                85                  90                  95

Glu Val Arg Ile Glu Arg Asp Gly Arg Arg Ser Glu Val His Gly Ser
            100                 105                 110

Leu Phe Arg Gly Gln Thr Gln Leu Thr Leu Asp Lys Phe Met His Tyr
        115                 120                 125

Phe Pro Glu Gly Gly Arg Arg Glu Gly His Gly Ala Leu Glu Ala Leu
    130                 135                 140

Pro Val Ile Pro Asp Phe Pro Thr Arg Ser Glu Val Leu Glu Ser Asn
145                 150                 155                 160

Gly Ser Ser Ala Ser Cys Leu Ala Met Asp Gly Val Pro Ile Val Ala
                165                 170                 175

Gly Ala Gly Leu Val Glu Tyr Leu Thr Asp Ile Gly Glu Asp Gly Asp
            180                 185                 190

Met Asp Phe Lys Ala Gly Thr Lys Gly Thr Ala Leu Gln Asp Ile Lys
        195                 200                 205

Gly Ile Glu Ala Gln Gln Ala Glu Ile Leu Met Thr Ser Arg Pro Thr
    210                 215                 220

Lys Gly Pro Gly Lys Glu Thr Gly Val Ile Thr Ser Ala Ile Gln Leu
225                 230                 235                 240

Gly Val Lys Leu Glu
                245

<210> SEQ ID NO 46
<211> LENGTH: 47
<212> TYPE: RNA
<213> ORGANISM: Homo sapiens

<400> SEQUENCE: 46
uaauauuuau auauuuauau uuuuaaaaua uuuauuuauu uauuuaa              47

<210> SEQ ID NO 47
<211> LENGTH: 11
<212> TYPE: RNA
<213> ORGANISM: Homo sapiens

<400> SEQUENCE: 47
uauuuauuua a                                                     11
```

```
<210> SEQ ID NO 48
<211> LENGTH: 33
<212> TYPE: RNA
<213> ORGANISM: Homo sapiens

<400> SEQUENCE: 48
uauuuauuua aauauuuaaa uuuuauauuu aau                          33

<210> SEQ ID NO 49
<211> LENGTH: 62
<212> TYPE: RNA
<213> ORGANISM: Homo sapiens

<400> SEQUENCE: 49
guuuuuaauu uauuuauuaa gauggauucu cagauauuua uauuuuuau uuuauuuuuu   60 uu                                                            62

<210> SEQ ID NO 50
<211> LENGTH: 111
<212> TYPE: RNA
<213> ORGANISM: Homo sapiens

<400> SEQUENCE: 50
auuuacaugu gccauuuuuu uaauucgagu aacccauauu uguuuaauug uauuuacauu   60
auaaaucaag aaauauuuau uauuaaaagu aagucauuua uacaucuuag a          111

<210> SEQ ID NO 51
<211> LENGTH: 34
<212> TYPE: RNA
<213> ORGANISM: Homo sapiens

<400> SEQUENCE: 51
aauuaauuua uuauuuauuu auuauuuauu uauu                         34
```